(12) United States Patent
Selten et al.

(10) Patent No.: US 6,432,672 B1
(45) Date of Patent: Aug. 13, 2002

(54) GENE CONVERSION AS A TOOL FOR THE CONSTRUCTION OF RECOMBINANT INDUSTRIAL FILAMENTOUS FUNGI

(76) Inventors: Gerardus Cornelis Maria Selten, Sterrenweg 81, 2651 HZ Berkel EN Rodenrijs; Bart Willem Swinkels, Schutterstraat 5, 2611 MX Delft; Roelof Ary Lans Bovenberg, 's-Gravenweg 121, 3062 ZD Rotterdam, all of (NL)

(*) Notice: Subject to any disclaimer, the term of this patent is extended or adjusted under 35 U.S.C. 154(b) by 0 days.

(21) Appl. No.: 09/402,631

(22) PCT Filed: Apr. 9, 1998

(86) PCT No.: PCT/EP98/02070
§ 371 (c)(1),
(2), (4) Date: Jan. 24, 2000

(87) PCT Pub. No.: WO98/46772
PCT Pub. Date: Oct. 22, 1998

(30) Foreign Application Priority Data

Apr. 11, 1997 (EP) ............................................. 97201091

(51) Int. Cl.$^7$ ............................ C12P 21/02; C12N 1/15; C12N 15/80
(52) U.S. Cl. .................................. 435/69.1; 435/254.11; 435/254.3; 435/254.4; 435/254.5; 435/254.6; 435/254.7; 435/254.8; 435/254.9; 435/477
(58) Field of Search .............................. 435/483, 254.1, 435/254.3–254.9, 471, 69.1, 254.11, 477

(56) References Cited

FOREIGN PATENT DOCUMENTS

| EP | 0 357 127 A | 3/1990 |
| EP | 0 635 574 A | 1/1995 |
| EP | 0 758 020 A | 2/1997 |
| WO | WO 91 00920 A | 1/1991 |
| WO | WO 95 17513 A | 6/1995 |

OTHER PUBLICATIONS

Verdoes, Journal of Biotechnology, vol. 36 (1994), "Evaluation of molecular and genetic approaches to generate glucoamylase overproducing strains of Aspergillus niger", pp. 165–175.

Farman, Molecular and General Genetics, vol. 231 (1992), "Transformation frequencies are enhanced and vector DNA is target during retransformation of Leptosphaeria maculans, a fungal plant pathogen", pp. 243–247.

Verdoes et al., Transgenic Research, vol. 2 (1993), "Glucoamylase overexpression in Aspergillus niger: molecular genetic analysis of strains containing multiple copies of the glaA gene", pp. 84–92.

*Primary Examiner*—Robert A. Schwartzman

(57) ABSTRACT

The present invention relates to filamentous fungi that comprise in their genomes at least two substantially homologous DNA domains which are suitable for integration of one or more copies of a recombinant DNA molecule and wherein at least two of these DNA domains comprise an integrated copy of a recombinant DNA molecule. The invention also relates to methods for preparing such filamentous fungi and for further multiplying the DNA domains with integrated recombinant DNA molecules through gene conversion or amplification.

29 Claims, 69 Drawing Sheets

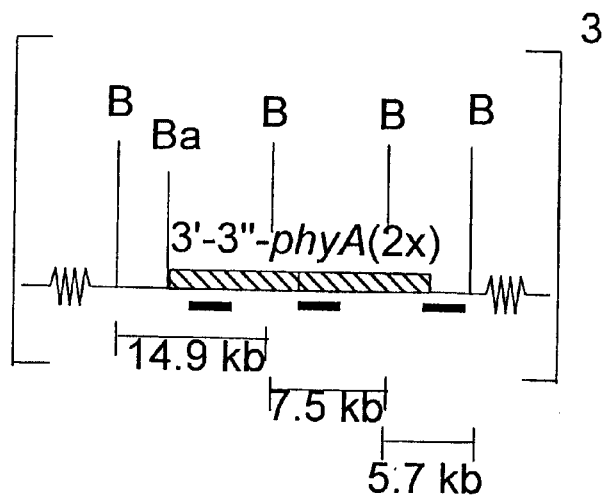
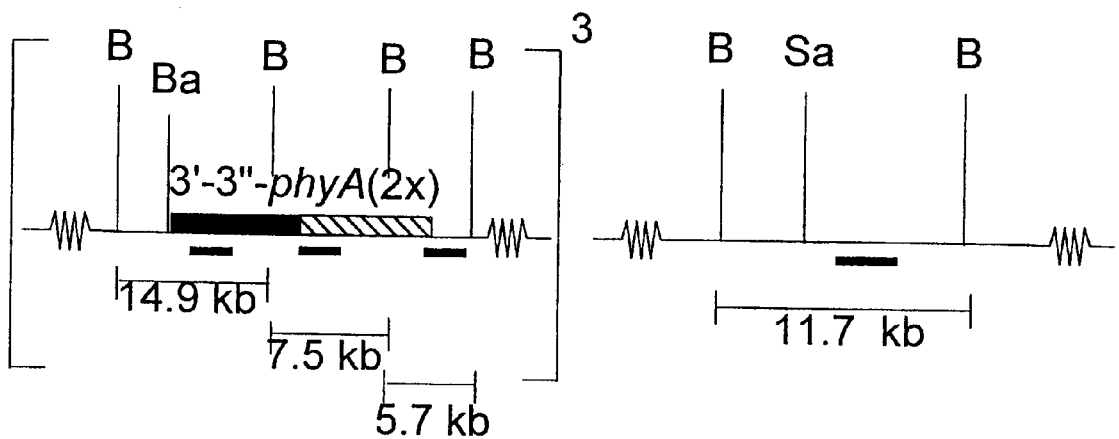
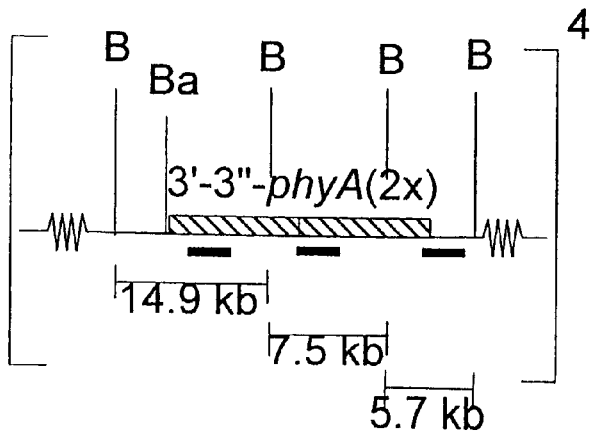
Figure 28        — probe

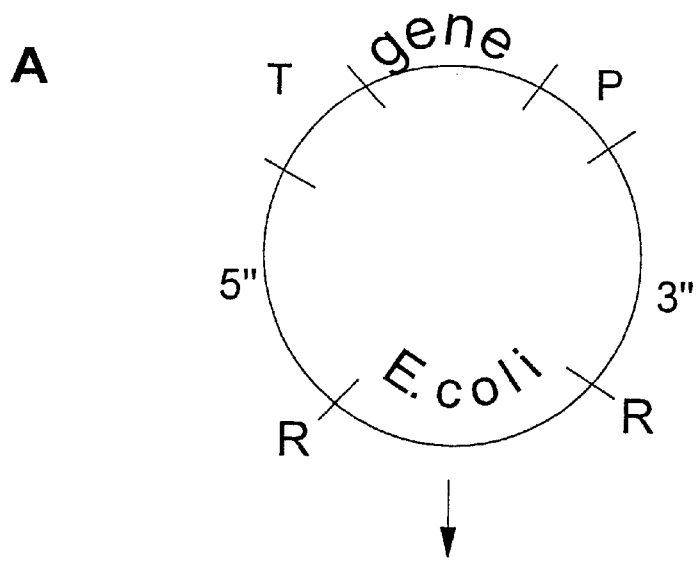
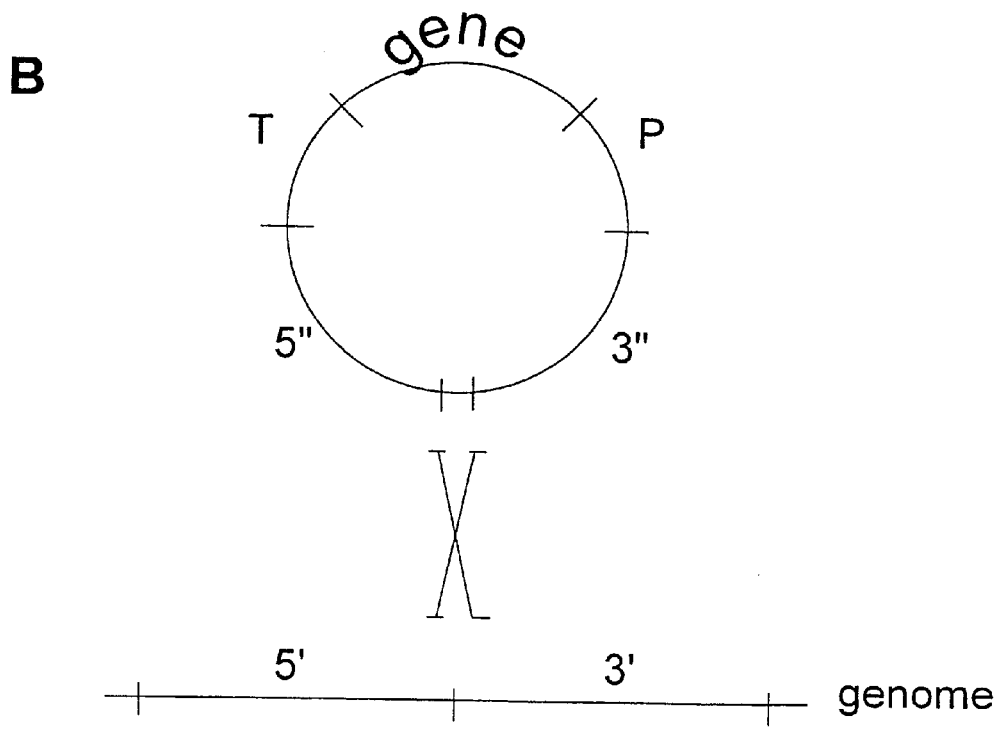
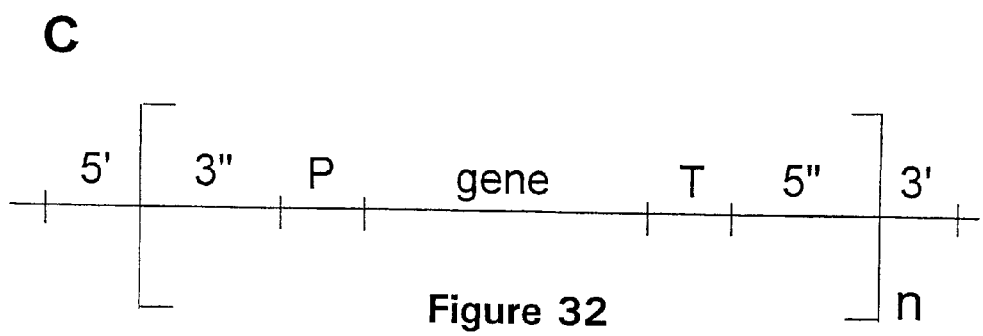
Figure 32

A
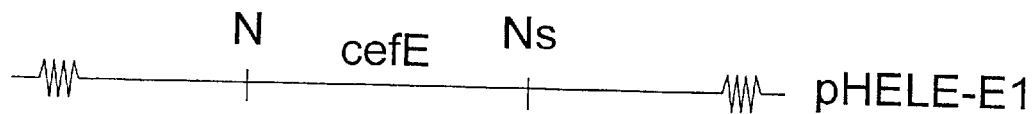
B
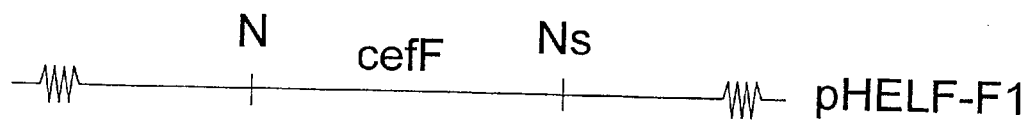
C
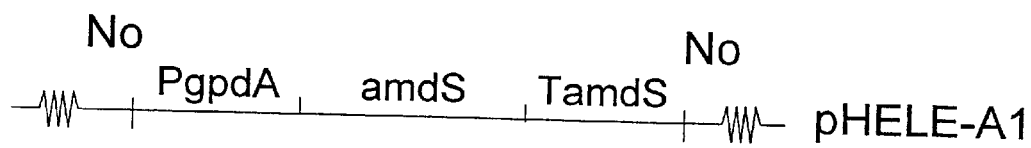
D
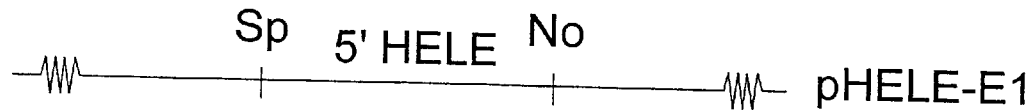
E
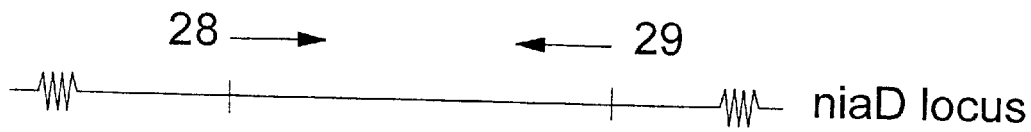
Figure 42

GENE CONVERSION AS A TOOL FOR THE CONSTRUCTION OF RECOMBINANT INDUSTRIAL FILAMENTOUS FUNGI

FIELD OF THE INVENTION

The present invention relates to genetic engineering of microorganisms used in industrial fermentation processes.

BACKGROUND OF THE INVENTION

An ever increasing number of products is produced by microbial fermentation at industrial scale. Such products range from primary and secondary metabolites, such as e.g. citric acid and antibiotics, respectively, to proteins, enzymes and even complete microorganisms, e.g. in the form of baker's yeast or biomass. Traditionally, the microorganisms in question have been subjected to classical strain improvement programs which consist of successive rounds of mutagenesis and subsequent selection of mutants with improved performance. More recently, also genetic engineering, i.e. recombinant DNA technology, has been applied to industrial microorganisms. This technology has not only allowed further improvement of production levels of products naturally produced by the microorganism in question, but has also allowed the development of totally new products and/or production processes, such as e.g. the production of heterologous proteins or metabolic pathway engineering.

Genetic engineering requires the introduction and usually also the expression of a recombinant DNA molecule into the organism in question. This process is referred to as transformation. Stable transformation of a microorganism requires that the introduced recombinant DNA molecule is maintained in the cells from generation to generation, i.e. stable inheritance. There are basically two ways of maintaining the introduced recombinant DNA molecule. First, the recombinant DNA can integrate into the host cell's genome, e.g. into one of its chromosomes. Once integrated the recombinant DNA is part of this chromosome and will thus be maintained by replication together with this chromosome. Second, the recombinant DNA can be introduced into the cell as part of a DNA molecule capable of autonomous replication, i.e. replication independent of the host's genome. Such autonomously replicating vectors are often derived from naturally occurring plasmids or viruses which have been adapted to accommodate the incorporation of the recombinant DNA.

With respect to industrial microbial production organisms the autonomous and the integrative vector systems each have their specific advantages and disadvantages. The autonomously replicating vector systems e.g. pose restrictions on the number and/or lengths of the DNA sequences to be introduced, are generally considered to be less stable and usually provide lower expression levels per gene copy as compared to the integrative systems. Most importantly, however, for some very important industrial microorganisms, notably the filamentous fungi such as Aspergillus, Penicillium or Trichoderma, stable autonomously replicating vector systems are simply not available.

With the integrative vector systems the disadvantages depend to some extent on the approach used for integration. Integration into a predetermined genomic sequence through homologous recombination is difficult to combine with high copy numbers of the recombinant DNA molecule. Whereas random integration of multiple copies of the recombinant DNA molecule, as frequently applied in filamentous fungi, will result in unpredictable genotypes of the transformants. Not only can this lead to a loss of advantageous properties of the transformed production strain, also the unpredictable and undefined nature of such strains is less easily accepted by the registration authorities.

WO 91/00920 discloses yeast strains in which multiple copies of recombinant DNA molecules are integrated in the ribosomal DNA repeat cluster. The recombinant DNA molecules, in this case expression vectors for heterologous genes, additionally comprise both a deficient selectable marker gene as well as yeast ribosomal DNA sequences, the latter of which enable integration of the vectors in the ribosomal DNA repeat cluster through homologous recombination. The deficient selectable marker gene is required for selection and stable maintenance of strains containing multiple copies of the vectors integrated in the ribosomal DNA repeat cluster. In addition, WO 91/000920 suggests that multicopy integration in ribosomal DNA repeats might also be applied in fungi in general, including filamentous fungi such as Aspergillus species. However, the multicopy integration system disclosed in WO 91/00920 is dependent on the use of a deficient selectable marker gene. Moreover, WO 91/00920 does not provide for integration into a genomic environment which is by nature adapted to support high level RNA polymerase II transcription of protein coding genes.

Recently, ES 2 094 088 described a DNA region which is amplified in penicilin overproducing strains of penicilium chrysogenum E-1 and penicilium chrysogenum AS-P-78. The size of the amplified DNA region is described to be 75 and 106 kb, respectively, and contains the genes pcbAB, pcbC and penDE within a 16.5 kb fragment in the amplified region. It is proposed that the DNA sequences present at the left hand and right hand ends of the amplified region can be used for the construction of vectors into which marker genes have been introduced in order to promote the amplification of genetic material situated between them, in particular for obtaining strains with greater production of penicilin by random mutagenesis with nitrosoguanidine in order to increase the copy number of the vector once it has been integrated into the genome of the microorganism. However, ES 2 094 088 fails to describe whether the approach outlined above could successfully be employed. Indeed, the method described in ES 2 094 088 suffers from several drawbacks. For example, amplification of complex DNA structures occur only at low frequency. Furthermore, the use of the mutagen nitrosoguanidine results in undesired spontaneous mutations in the genome of the microorganism. Moreover, mutagenic treatment can result in the deletion of the sequences of the amplified region present in the vector and, therefore, the deletion of the gene of interest situated between them; see also Fierro, Proc. Natl. Acad. Sci. USA (1995), 6200–6204. Also, as described above the random integration of the vector into the genome of the microorganism will result in unpredictable genotypes of the transformance.

Thus, the technical problem underlying the present invention is to provide a generally applicable approach for the construction of recombinant production strains of filamentous fungi that contain multiple copies of a recombinant DNA molecule integrated in defined predetermined target loci in its genome and which system is not dependent on the use of a particular type of selectable marker for transformation.

BRIEF DESCRIPTION OF THE DRAWINGS

Abbreviations Used in the Figures
Ryestriction Enzymes and Restriction Sites:
A=ApaI; Ba=BamHI; B=BglII; Bs=BssHII; E=EcoRI; H=HindIII; K=KpnI; N=NdeI; No=NotI; Ps=PstI; P=PvuII;

Sa=SalI; Sc=ScaI; S=SmaI; Sn=SnaBI; Spe=SpeI; Sp=SphI; Ss=SstII; Xb=XbaI; X=XhoI; Nr=NruI; Hp=HpaI; Sf=SfiI; Ns=NsiI; Bst=BstXI.

FIGURE LEGENDS

Figure 1:
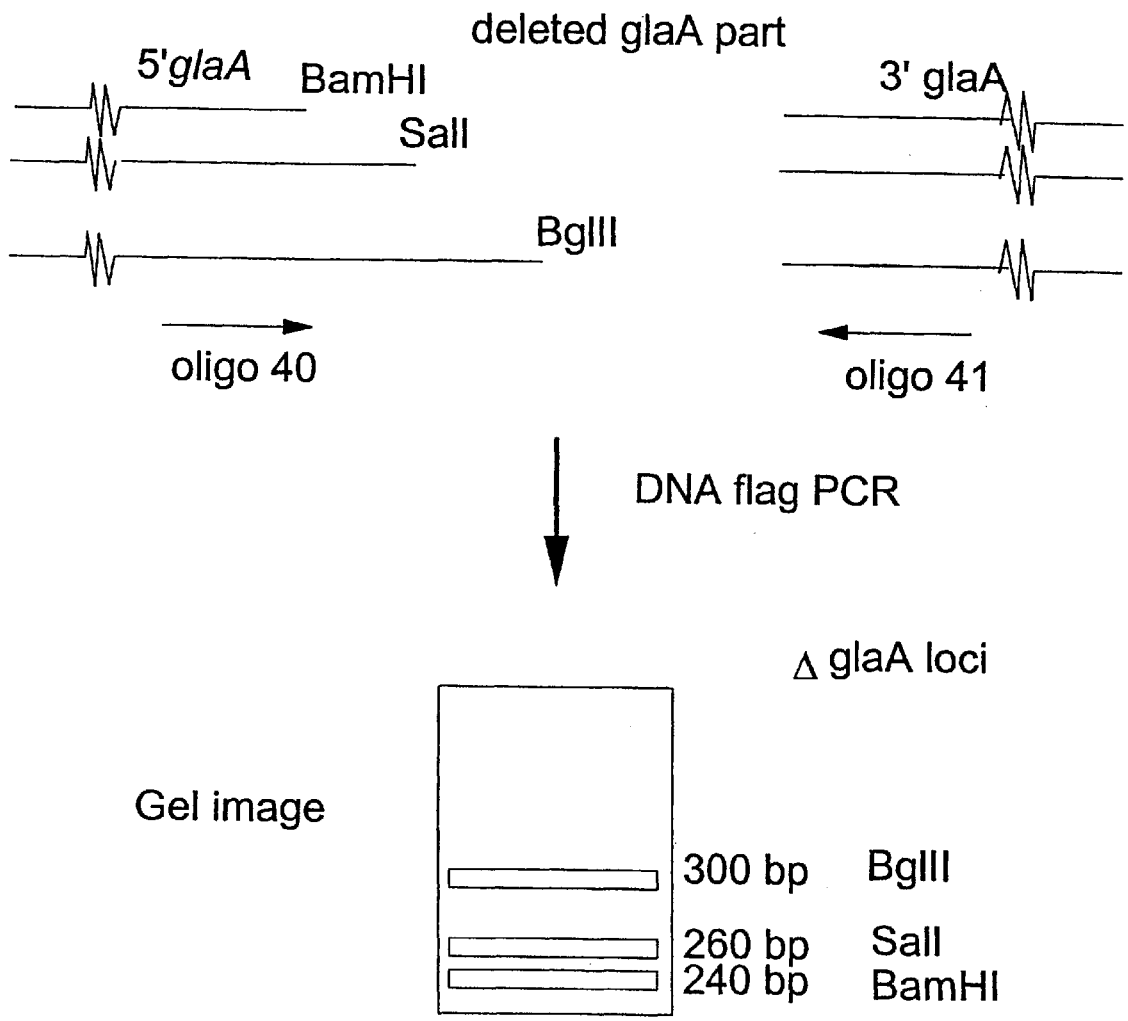

FIG. 1: Schematic view of the three ΔglaA loci in the glaA DNA amplicons of an *A. niger* CBS 646.97 (deposited on Apr. 11, 1997 at the Centraal Bureau voor Schimmelcultures, Baarn, The Netherlands) transformant (ISO-505), each marked by a different restriction site (BamHI, SalI or BglII). Truncation of each glaA locus differs by approximately 20 or 60 bp, to visualize each truncated glaA locus by the PCR-based DNA-flag test.

Figure 2:
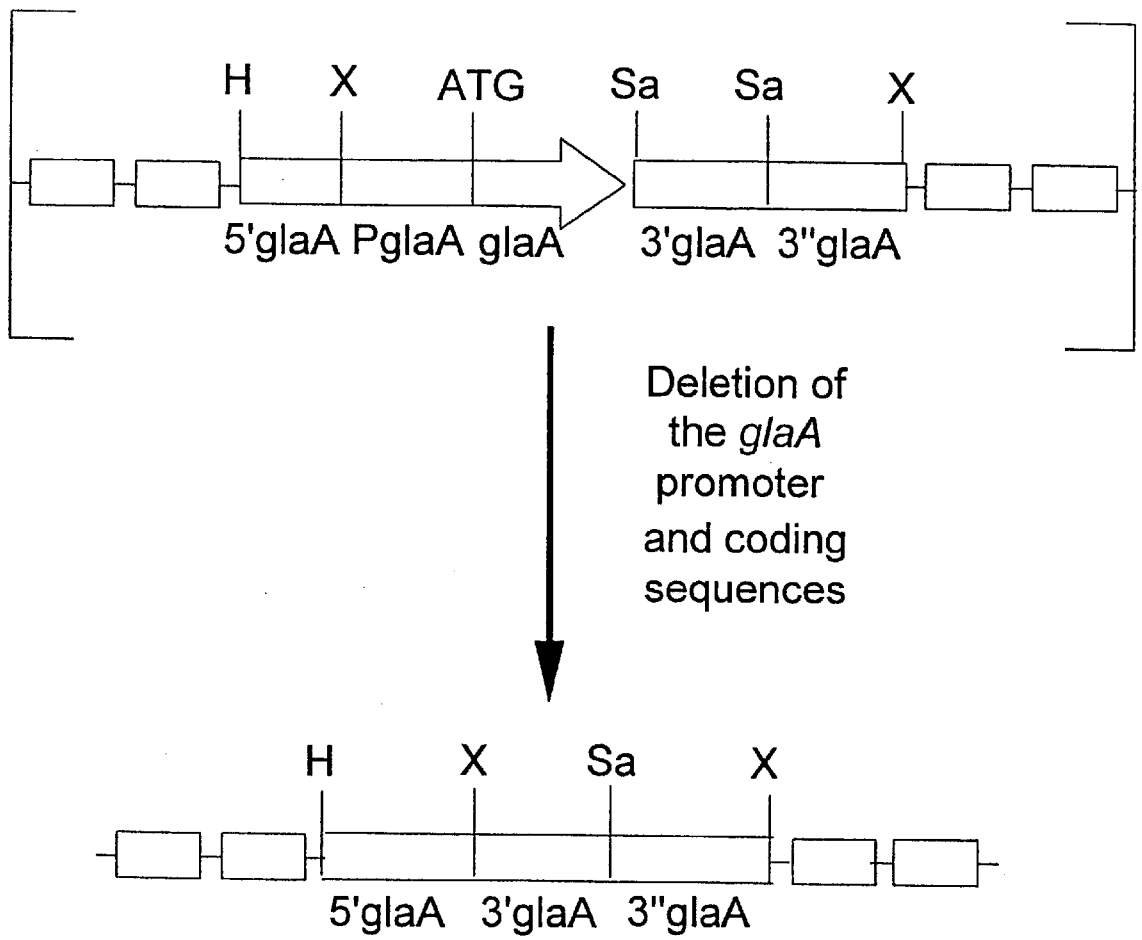

FIG. 2: Physical maps of the glaA loci in parental strain *A. niger* CBS 646.97 (upper part) and the three truncated "X-marked" glaA loci in recombinant strain *A. niger* ISO-505 (X stands for a BamHI, SalI or BglII restriction site).

Figure 3:
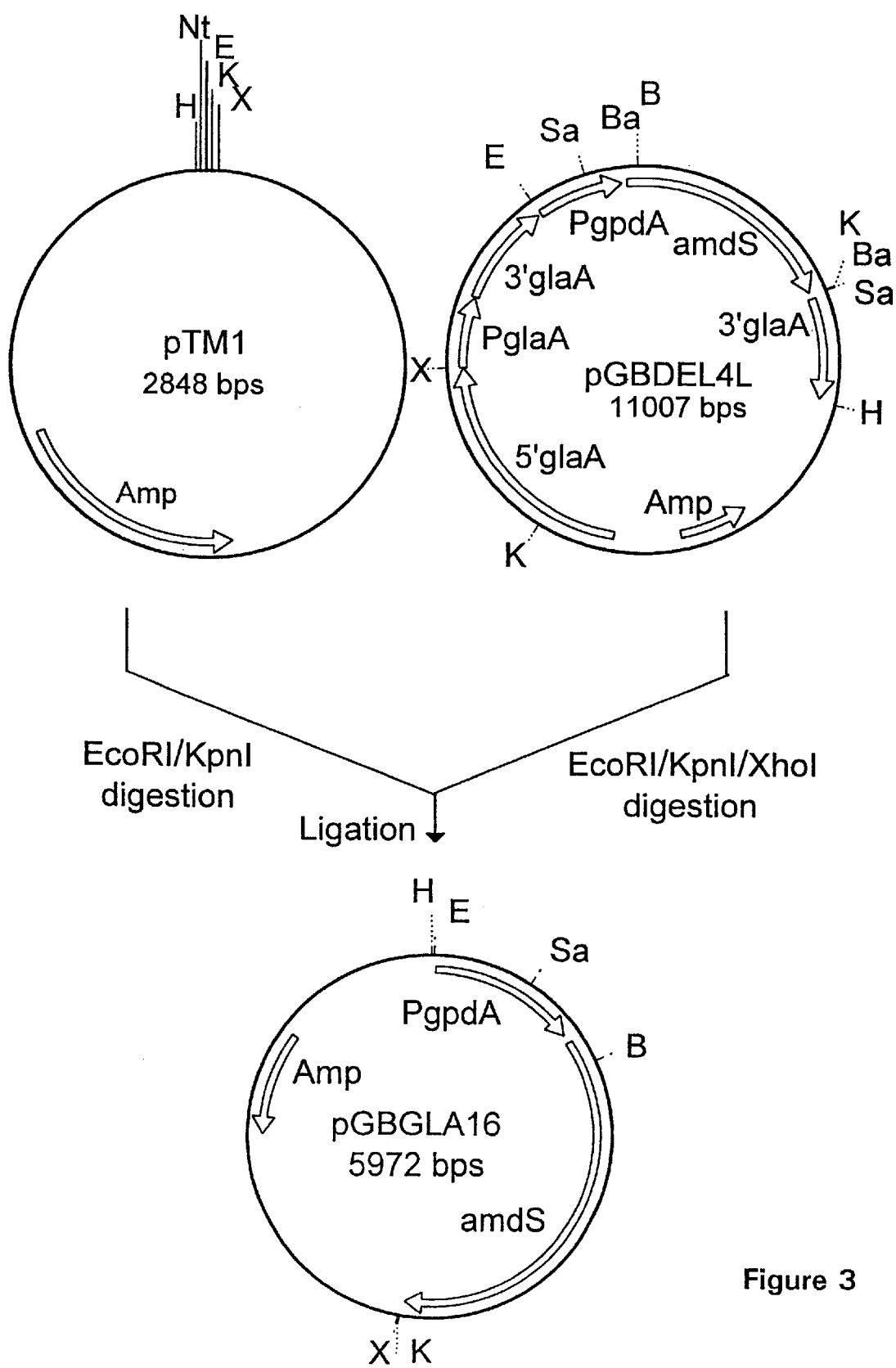

FIGS. 3A–3B: Construction pathway of the intermediate vector pGBGLA16.

Figure 4:
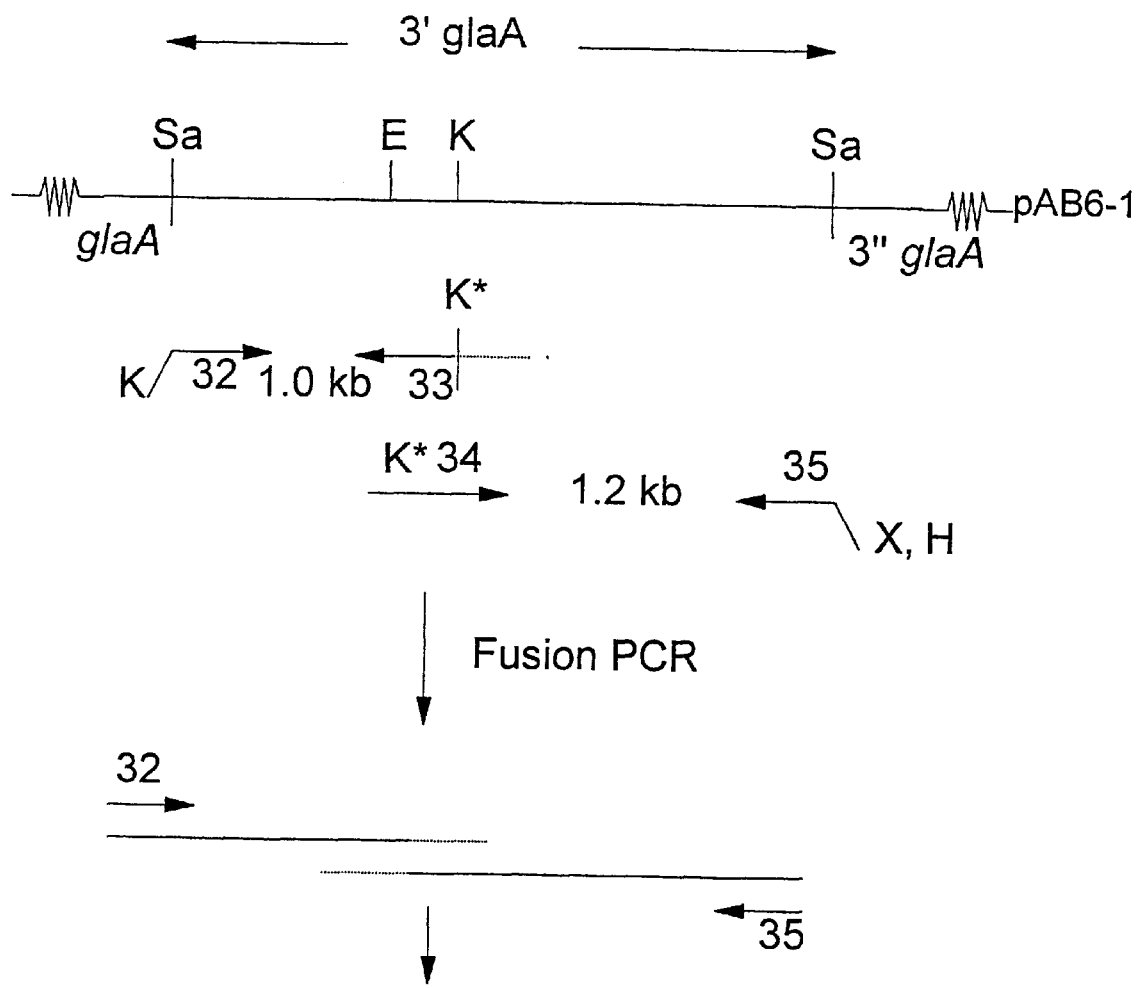
Figure 4:
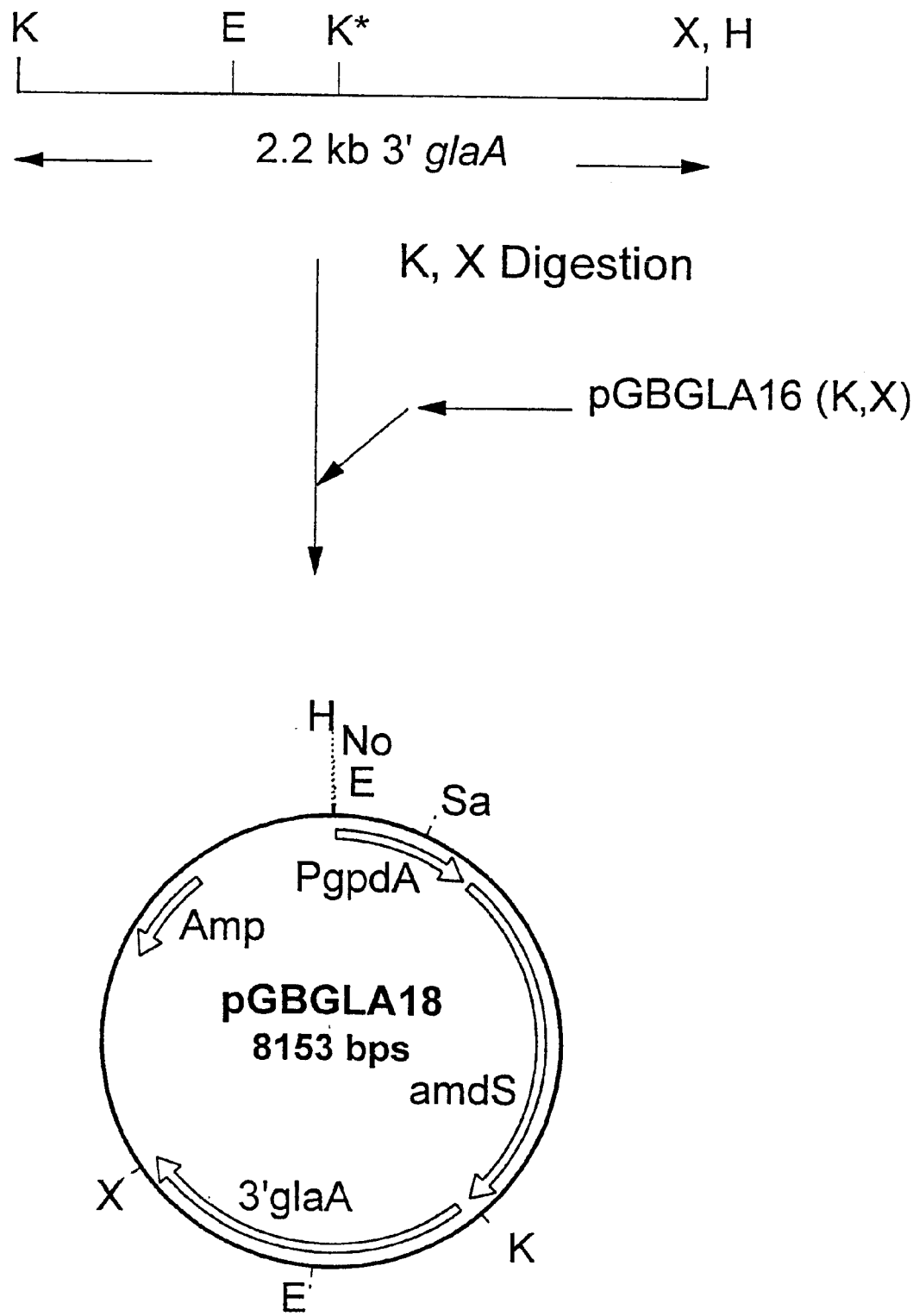

FIGS. 4A–4B: Schematic presentation of a fusion PCR to destroy the KpnI* in the 3'-glaA DNA sequence and to add cloning sites at the border for appropriate cloning into pGBGLA16 resulting in the intermediate vector pGBGLA18.

Figure 5:
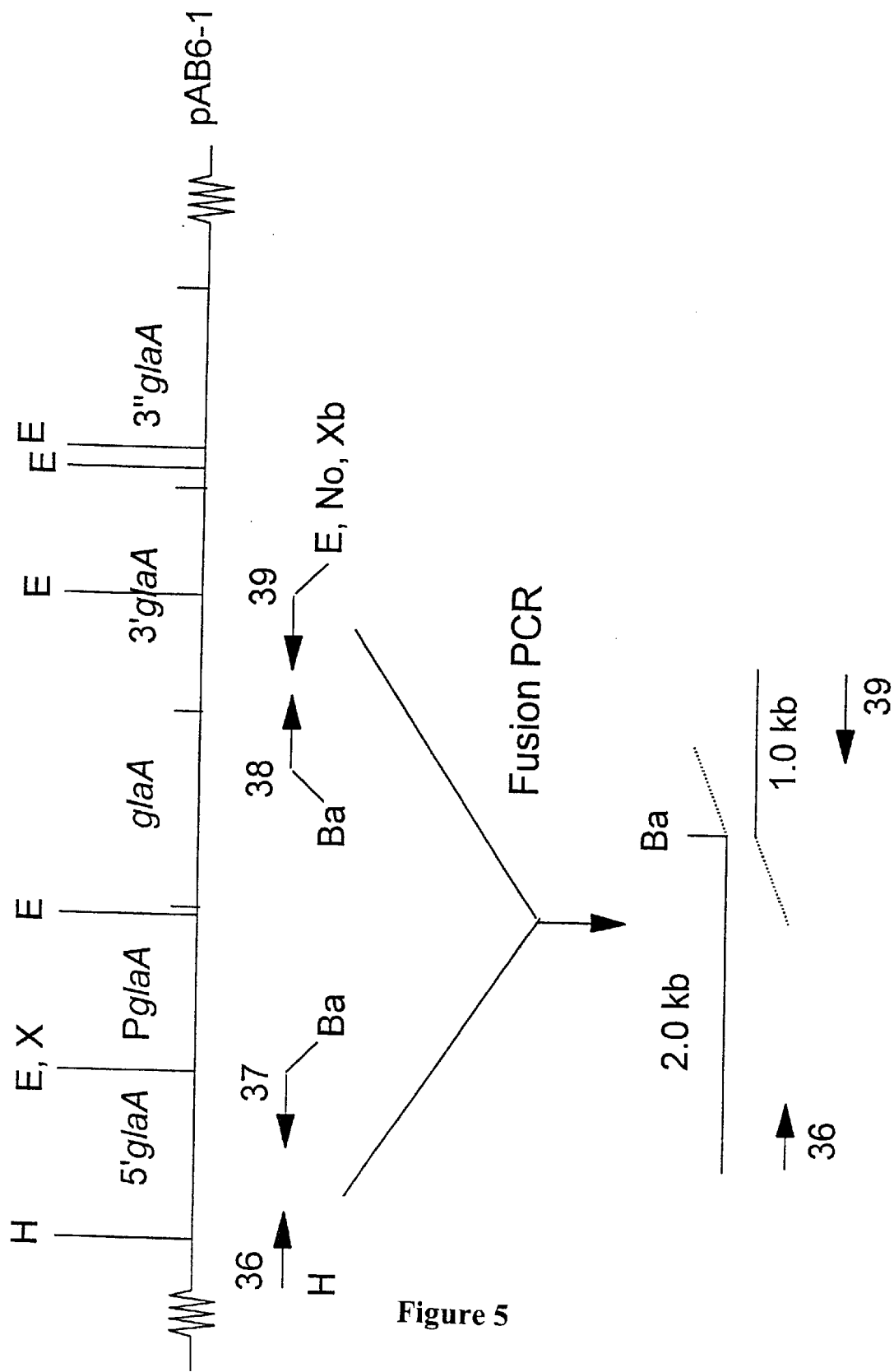
Figure 5:
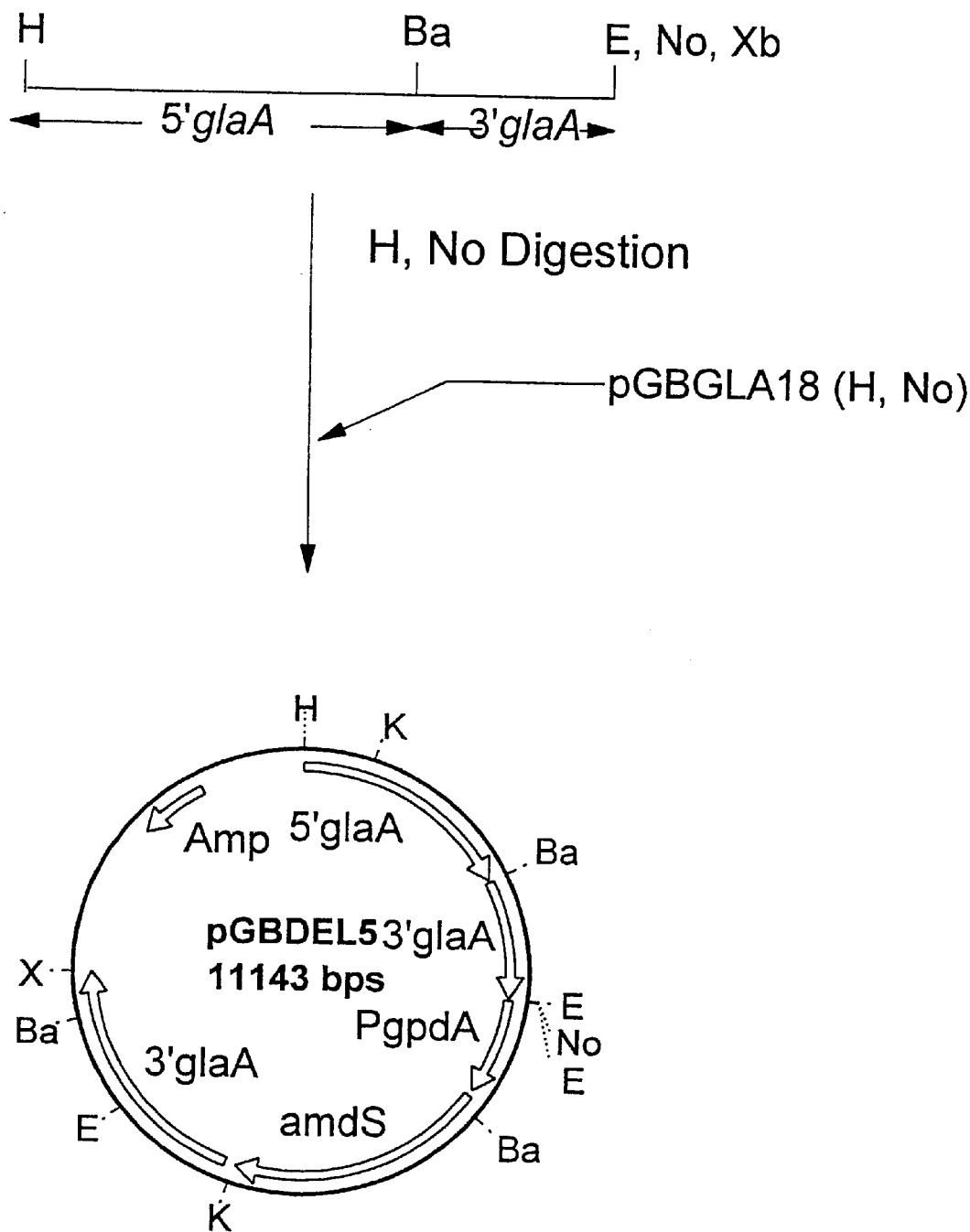

FIGS. 5A–5B: Schematic presentation of a fusion PCR to include a BamHI restriction site between the 5'- and 3'-glaA sequences and to add cloning sites at the border for appropriate cloning into pGBGLA18 resulting in the gene-replacement vector pGBDEL5.

Figure 6:
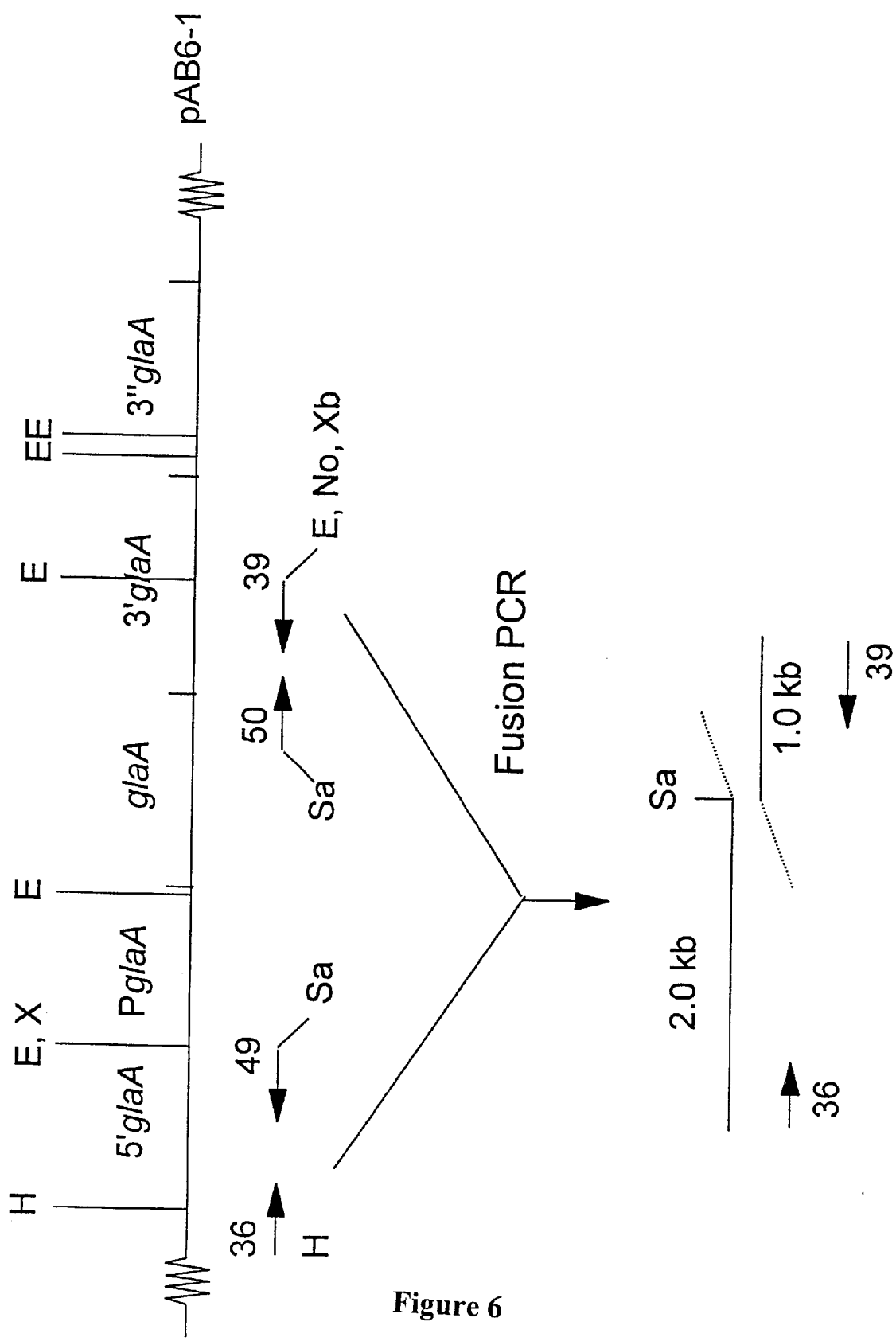
Figure 6:
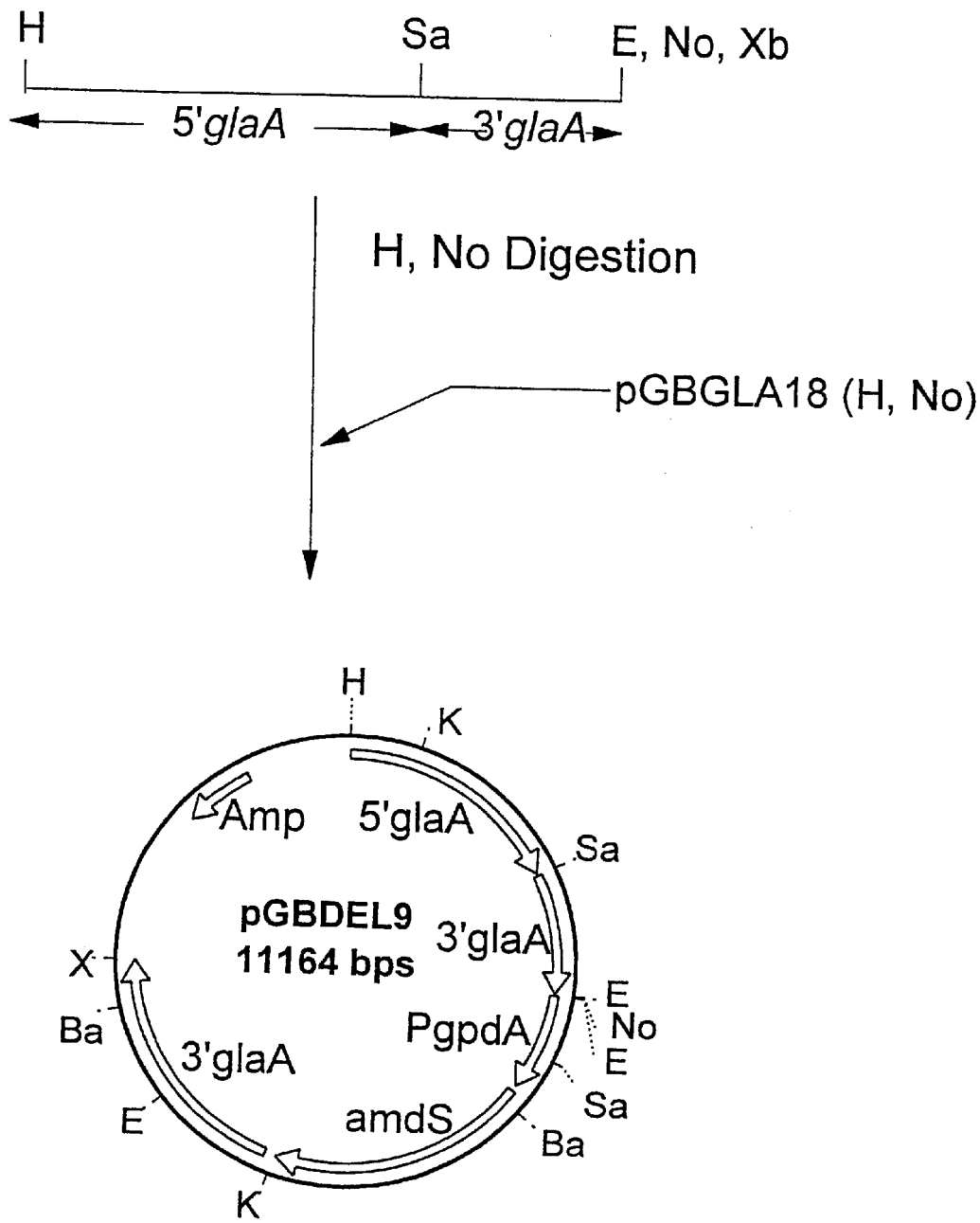

FIGS. 6A–6B: Schematic presentation of a fusion PCR to include a SalI restriction site between the 5'- and 3'-glaA sequences and to add cloning sites at the border for appropriate cloning into pGBGLA18 resulting in the gene-replacement vector pGBDEL9.

Figure 7:
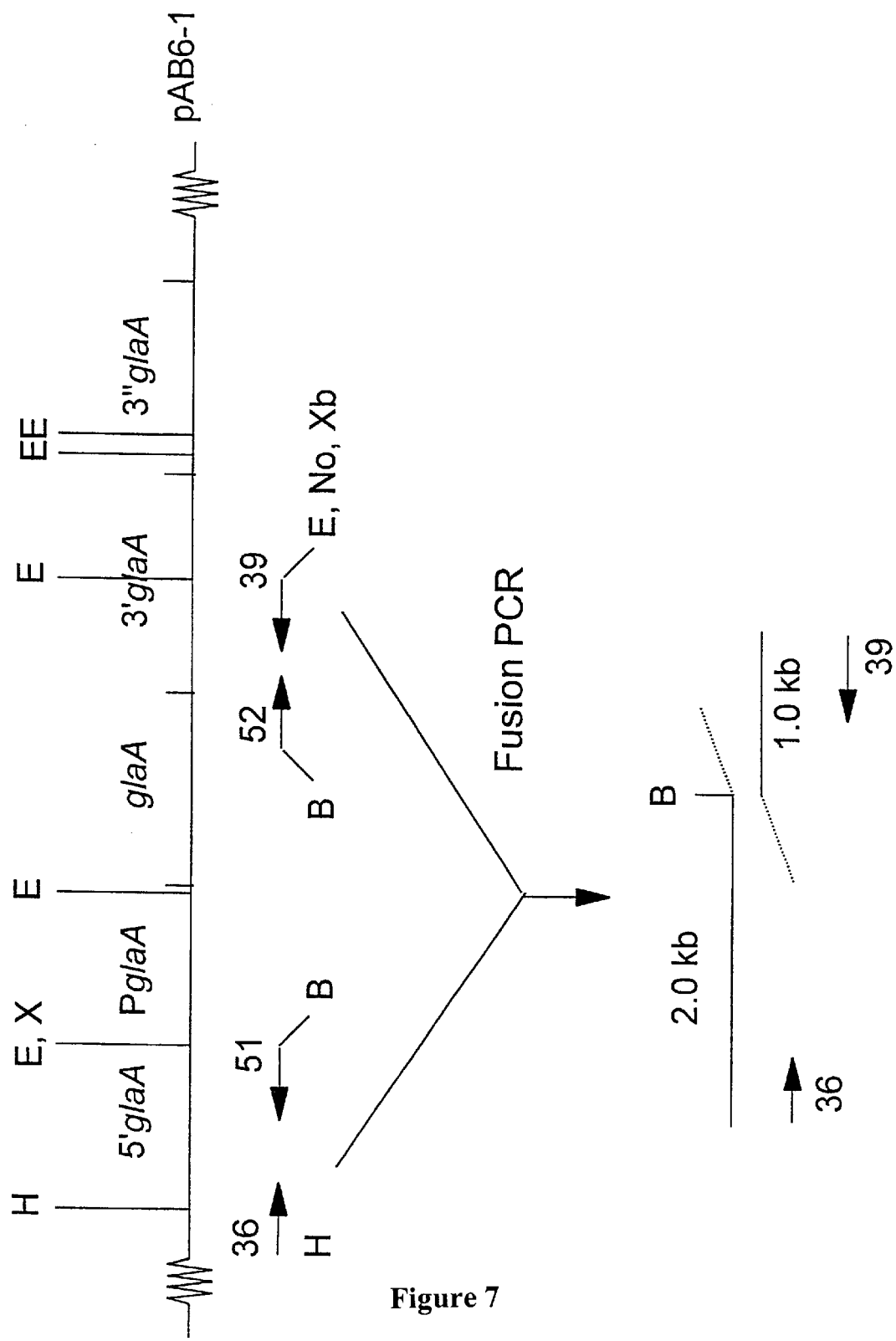
Figure 7:
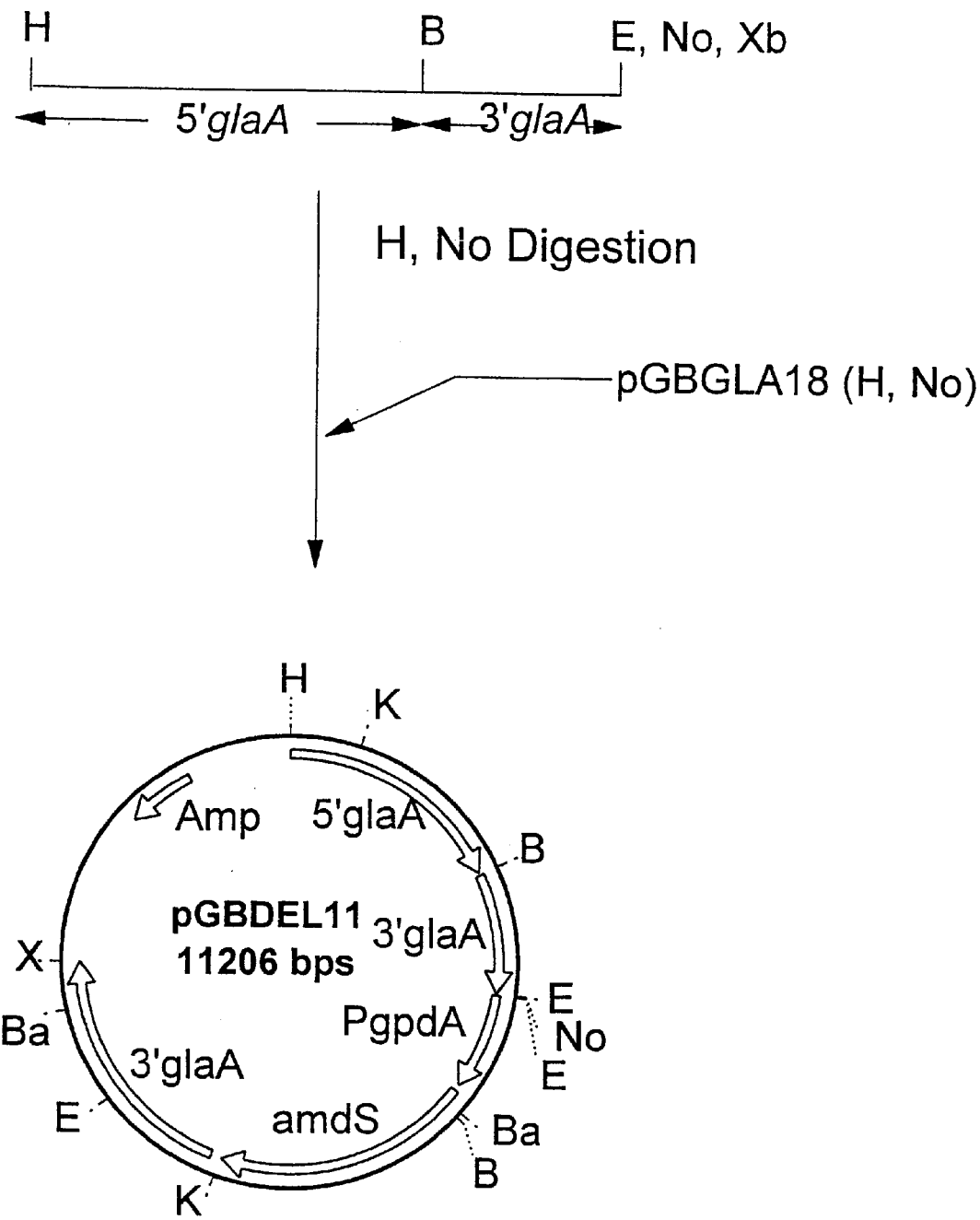

FIGS. 7A–7B: Schematic presentation of a fusion PCR to include a BglII restriction site between the 5'- and 3'-glaA sequences and to add cloning sites at the border for appropriate cloning into pGBGLA19 resulting in the gene-replacement vector pGBDEL11.

Figure 8:
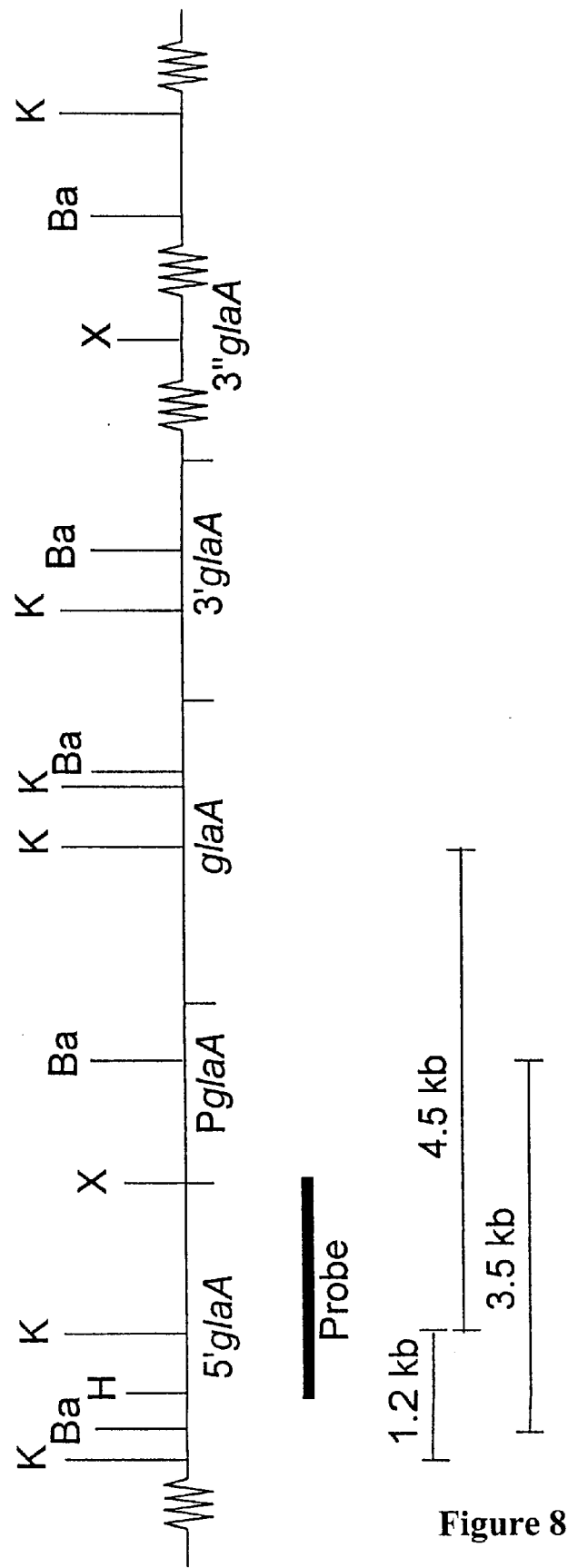
Figure 8:
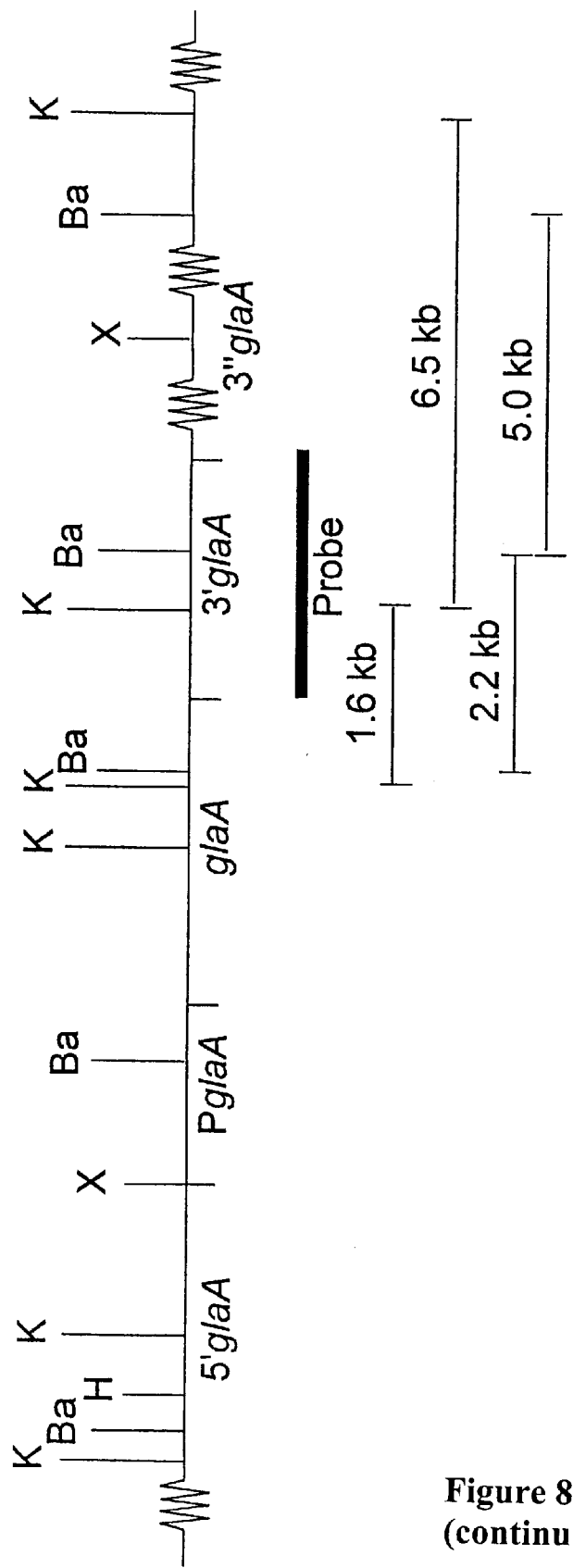

FIGS. 8A–8B: Schematic presentation of hybridization patterns observed after digestion with KpnI or BamHI of chromosomal DNA isolated from the parent strain *A. niger* CBS 646.97 probed with the HindIII/XhoI 5'-glaA DNA fragment (a) or the SalI/SalI 3'-glaA DNA fragment (b).

FIGS. 9A–9B: Schematic presentation of hybridization patterns observed after digestion with KpnI or BamHI of chromosomal DNA isolated from *A. niger* CBS 646.97 transformants, wherein the linearized pGBDEL5 vector has become integrated at the glaA target locus via a double cross-over, probed with the HindIII/XhoI 5'-glaA DNA fragment (a) or the SalI/SalI 3'-glaA DNA fragment (b). In the genome of individual transformants the original KpnI site located within the 3'-glaA sequence of the host might be destroyed (K*) but not necessarily, as a consequence of the double cross-over recombination event.

FIGS. 10A–10B: Schematic presentation of hybridization patterns observed after digestion with KpnI or BamHI of chromosomal DNA isolated from the amdS selection marker gene free transformant *A. niger* GBA-201, comprising one "BamHI-marked ΔglaA DNA amplicon and two remaining intact glaA amplicons, probed with the HindIII/XhoI 5'-glaA DNA fragment (a) or the SalI/SalI 3'-glaA DNA fragment (b).

Figure 11:
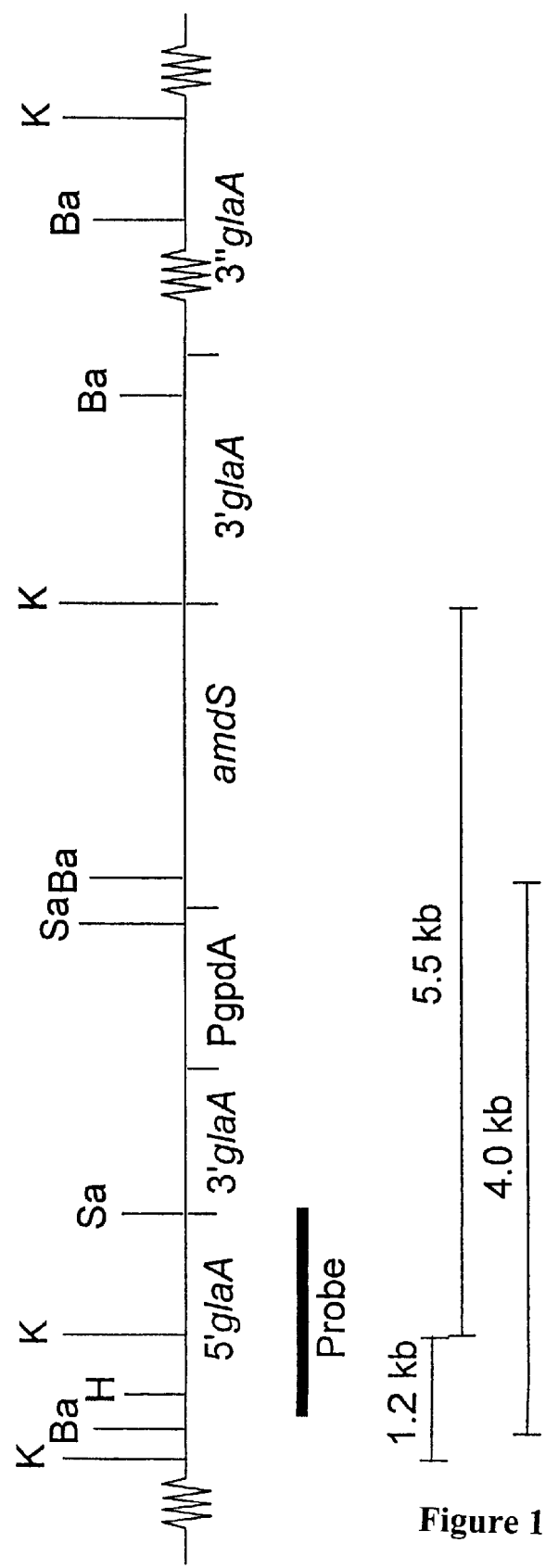
Figure 11:
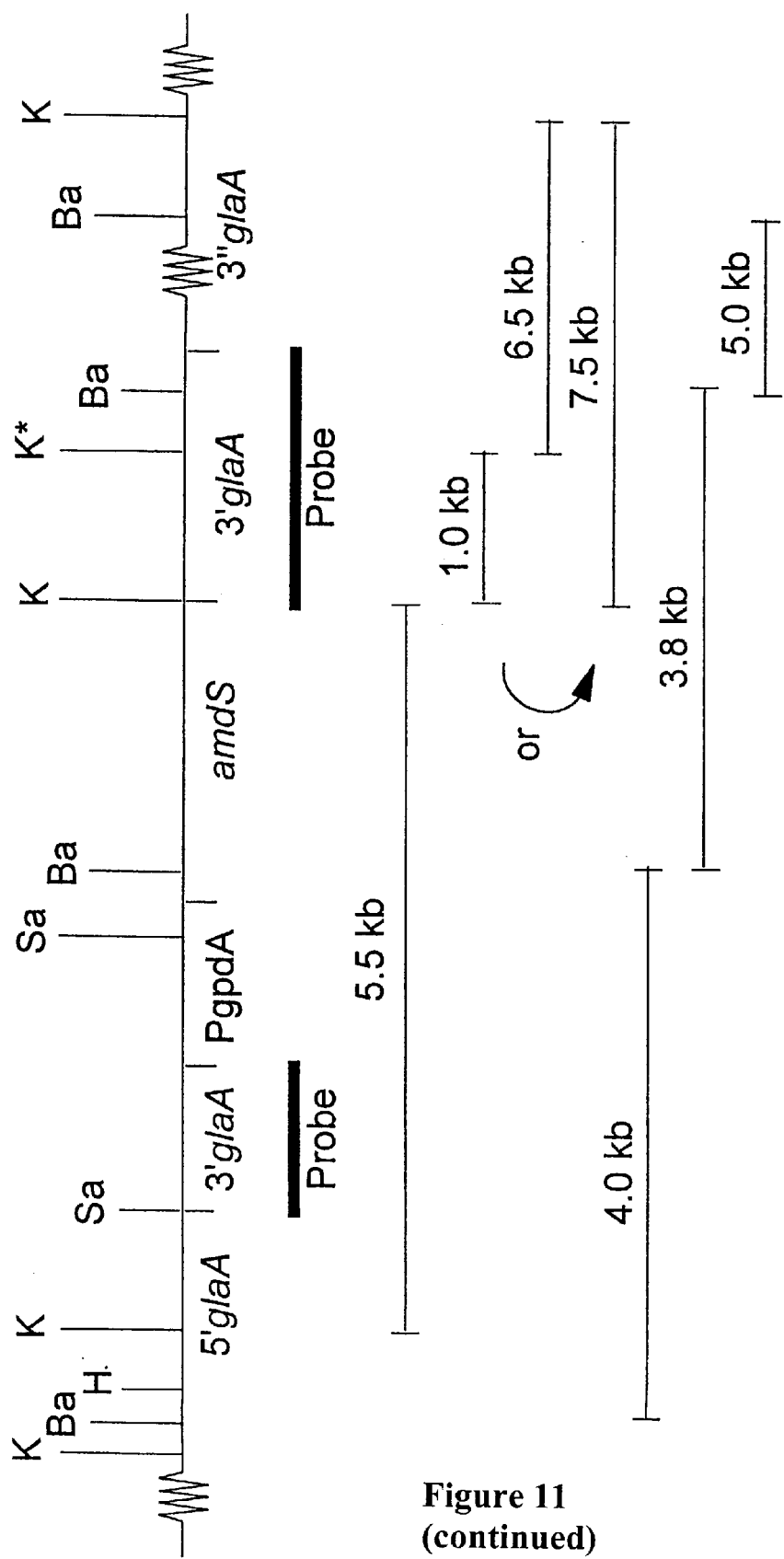

FIGS. 11A–11B: Schematic presentation of hybridization patterns observed after digestion with KpnI or BamHI of chromosomal DNA isolated from *A. niger* GBA-201 transformants, wherein the linearized pGBDEL9 vector has become integrated via a double cross-over, probed with the HindIII/XhoI 5'-glaA DNA fragment (a) or the SalI/SalI 3'-glaA DNA fragment (b). In the genome of individual transformants the original KpnI site located within the 3'-glaA sequence of the host might be destroyed (K*), but not necessarily as a consequence of the double cross-over recombination event.

Figure 12:
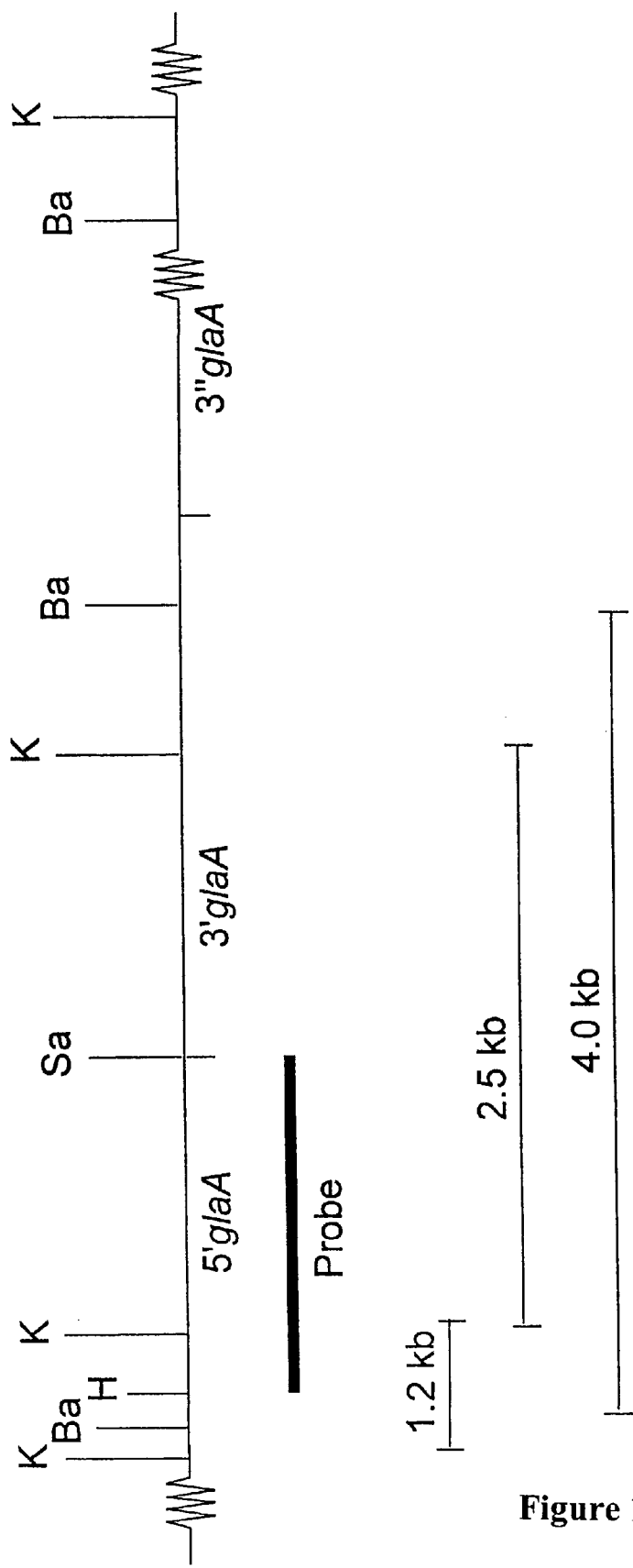
Figure 12:
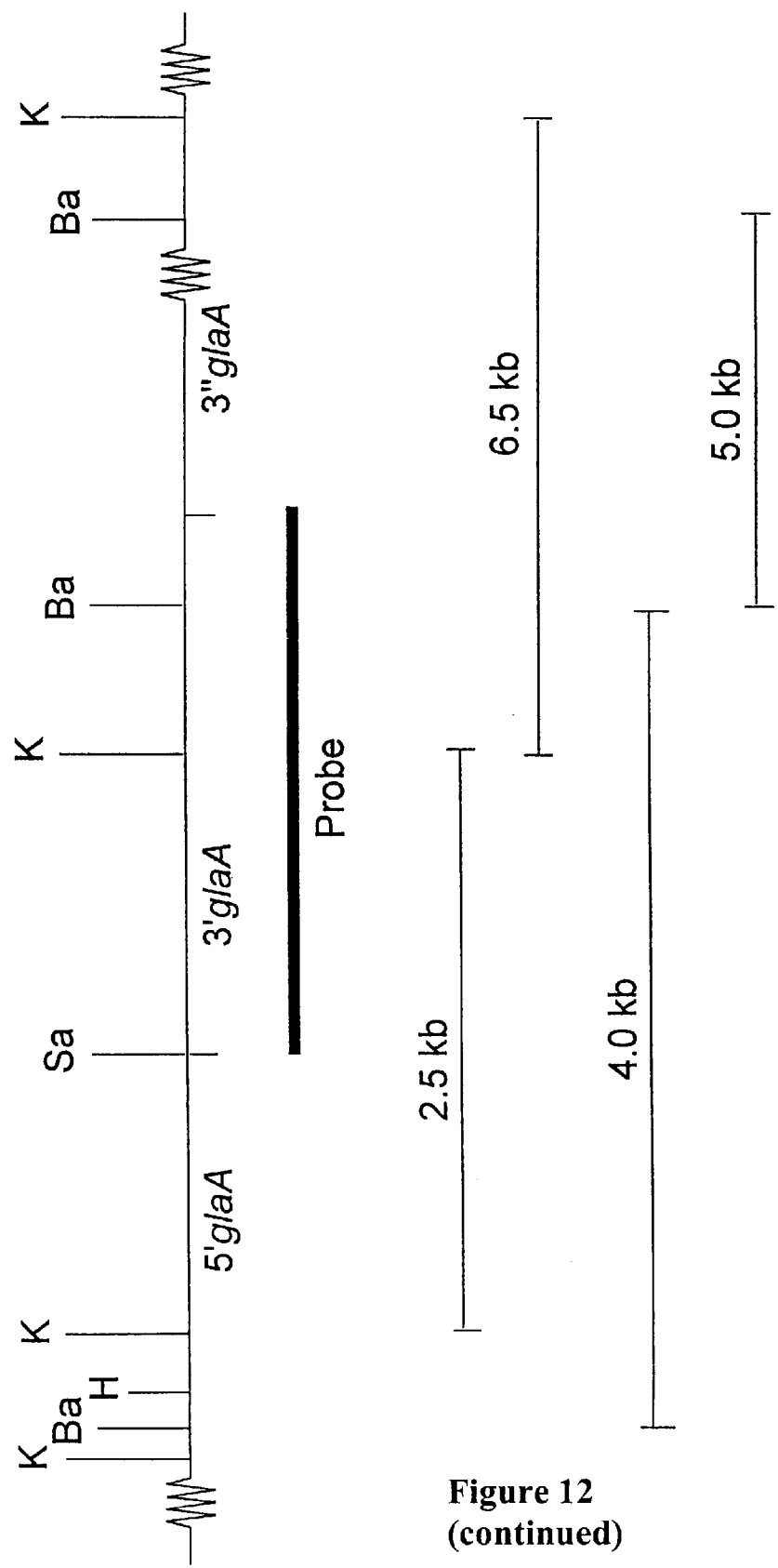

FIGS. 12A–12B: Schematic presentation of hybridization patterns observed after digestion with KpnI or BamHI of chromosomal DNA isolated from the amdS selection marker gene free transformant *A. niger* GBA-202, comprising two "BamHI- and SalI- marked" ΔglaA DNA amplicons and one remaining intact glaA amplicon, probed with the HindIII/XhoI 5'-glaA DNA fragment (a) or the SalI/SalI 3'-glaA DNA fragment (b).

FIGS. 13A–13B: Schematic presentation of hybridization patterns observed after digestion with KpnI or BamHI of chromosomal DNA isolated from *A. niger* GBA-202 transformants, wherein the linearized pGBDEL11 vector has become integrated via a double cross-over, probed with the HindIII/XhoI 5'-glaA DNA fragment (a) or the SalI/SalI 3'-glaA DNA fragment (b). In the genome of individual transformants the original KpnI site located within the 3'-glaA sequence of the host might be destroyed (K*) but not necessarily as a consequence of the double cross-over recombination event.

Figure 14:
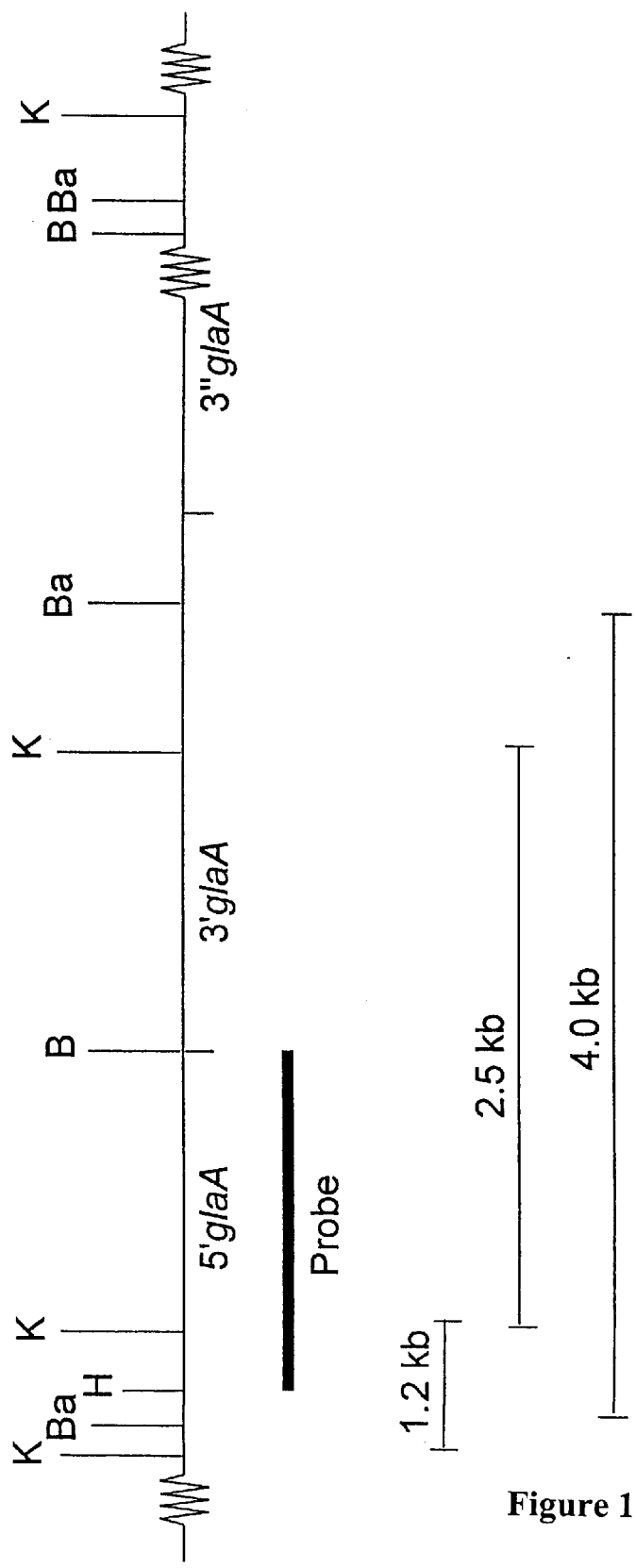
Figure 14:
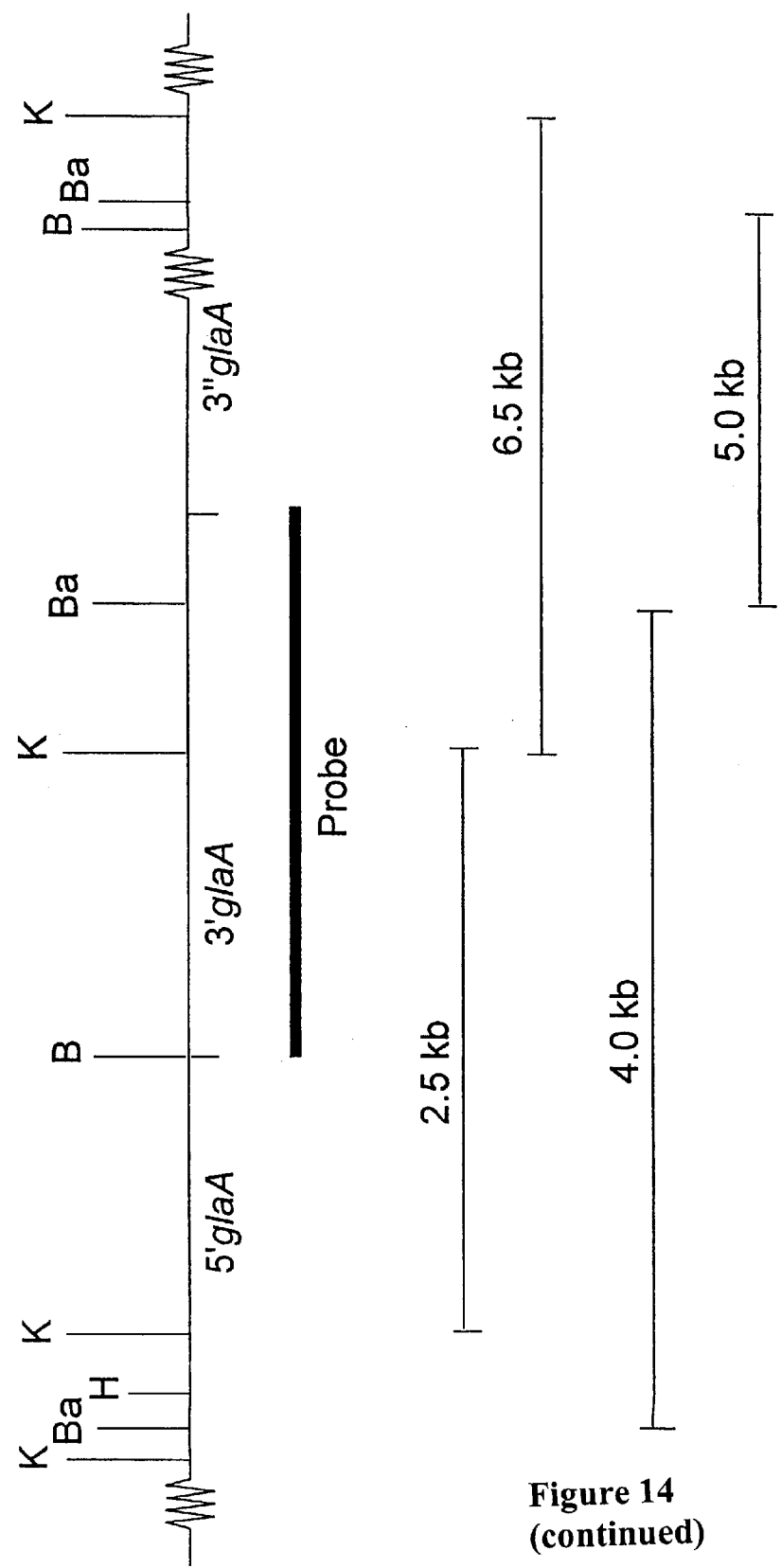

FIGS. 14A–14B: Schematic presentation of hybridization patterns observed after digestion with KpnI or BamHI of chromosomal DNA isolated from the amdS selection marker gene free transformant *A. niger* ISO-505, comprising three "BamHI-, SalI- and BglII-marked" ΔglaA DNA amplicons, probed with the HindIII/XhoI 5'-glaA DNA fragment (a) or the SalI/SalI 3'-glaA DNA fragment (b).

Figure 15:
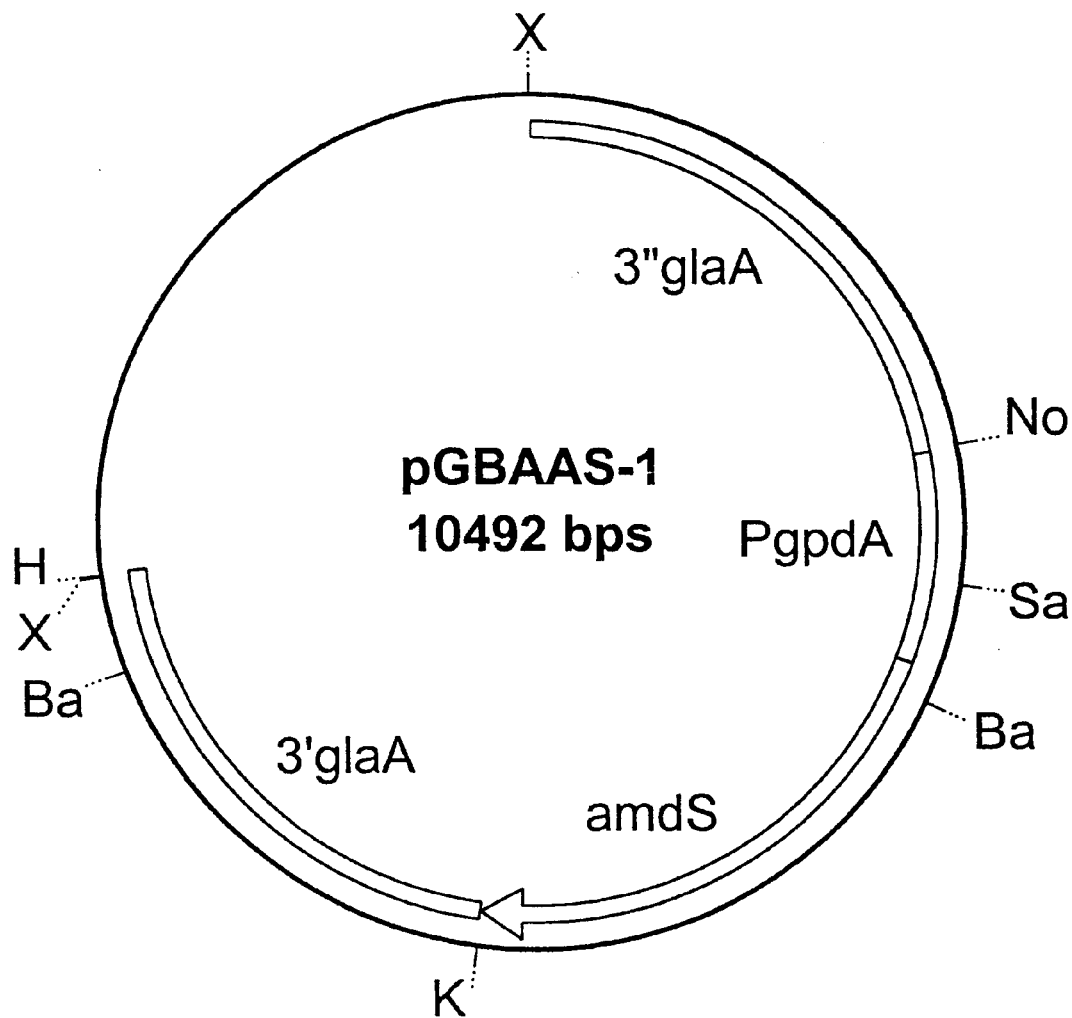

FIG. 15: Physical map of the acetamide selection marker and glaA targeting vector pGBAAS-1.

Figure 16:
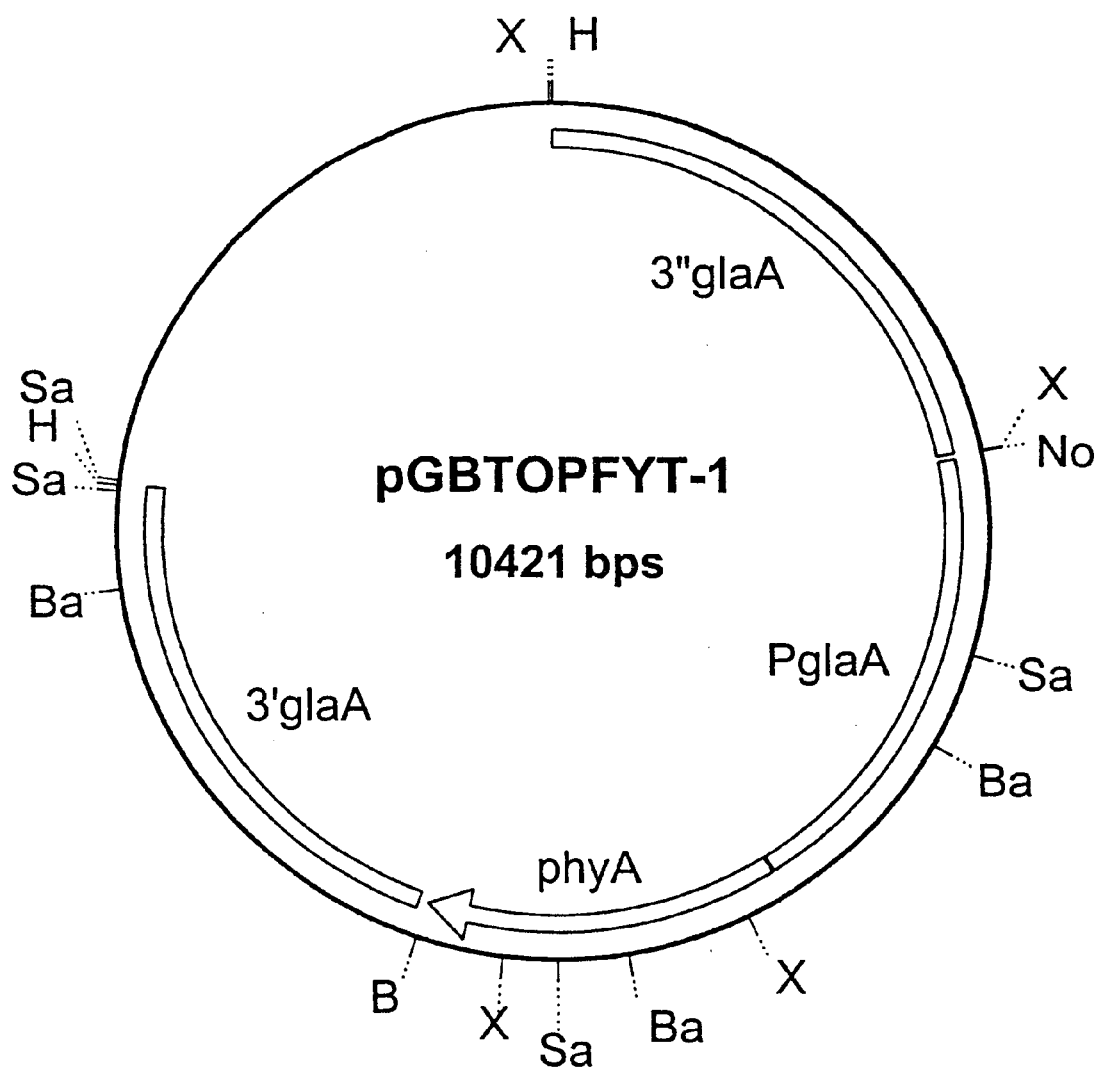

FIG. 16: Physical map of the phytase expression and glaA targeting vector pGBTOPFYT-1.

Figure 17:
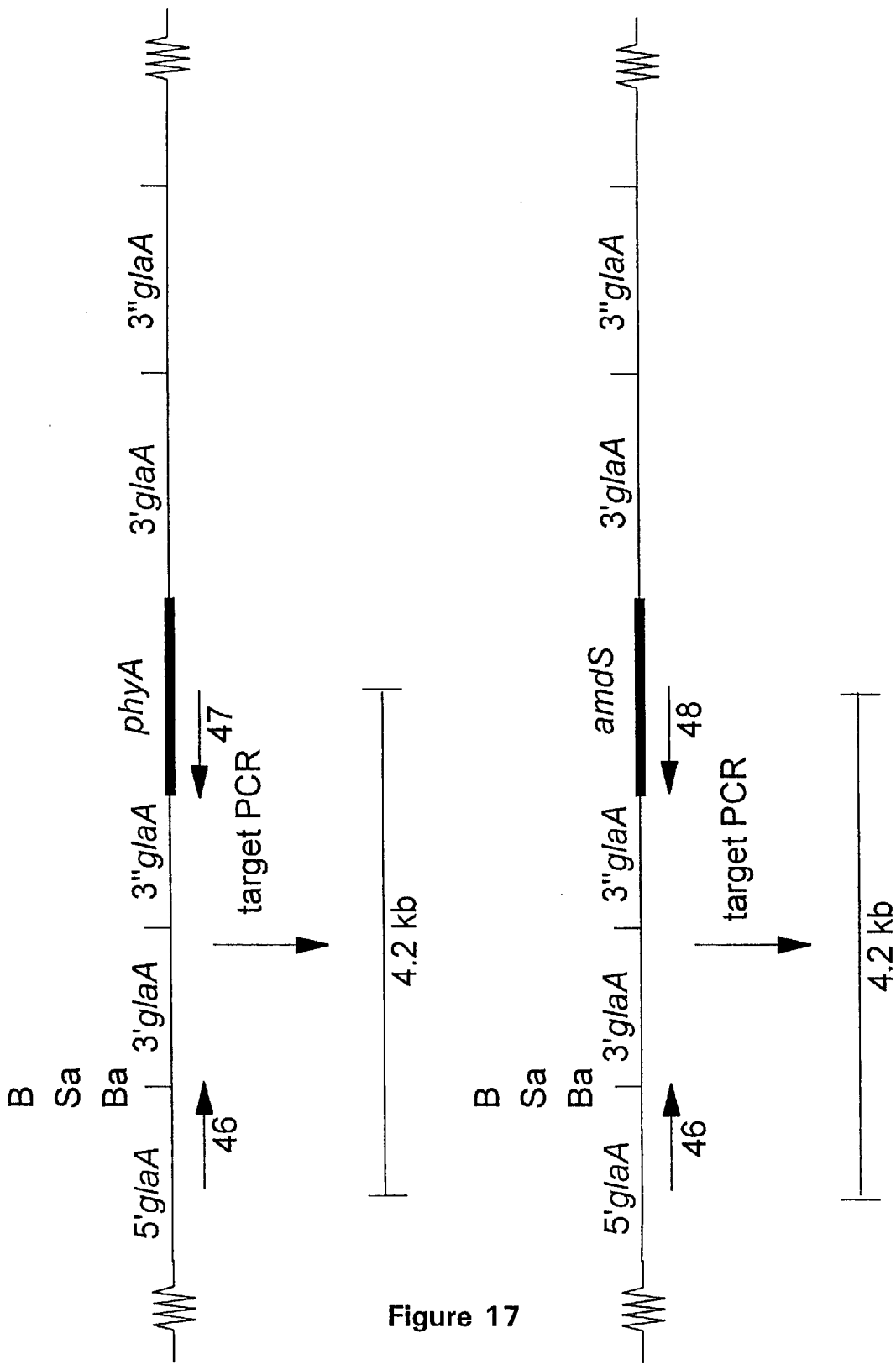

FIG. 17: Schematic illustration of the targeting PCR test to determine whether the phyA expression cassette (a) or the amdS cassette (b) has become targeted adjacent to one of the 3'-3"-glaA target loci in *A. niger* ISO-505 transformants. Targeting of one of these cassette results in both cases in amplification of a 4.2 kb sized DNA fragment.

Figure 18:
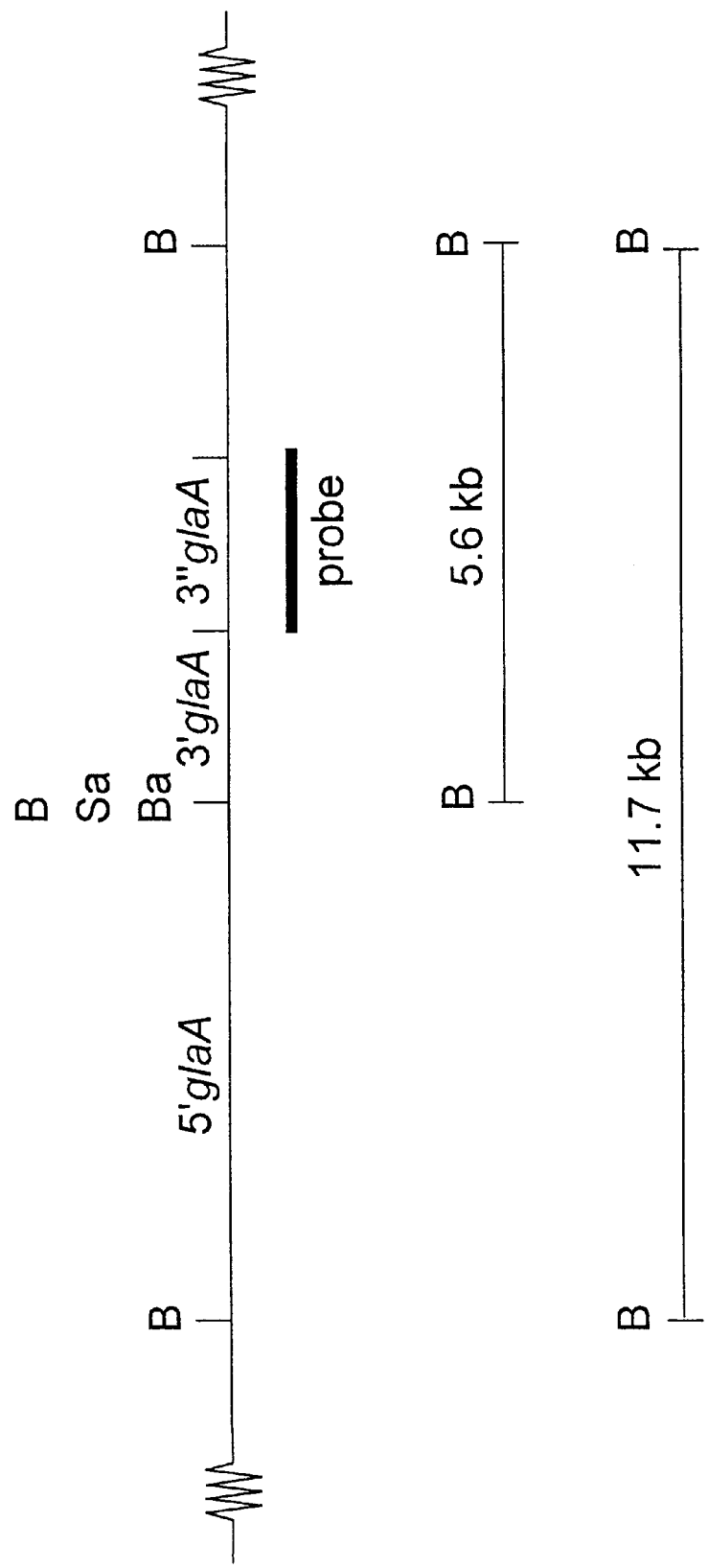

FIG. 18: Schematic illustration of the three ΔglaA domains in *A. niger* ISO-505. The hybridization pattern is shown of a BglII digest probed with the 2.2 kb SalI/XhoI 3"-glaA DNA fragment.

Figure 19:
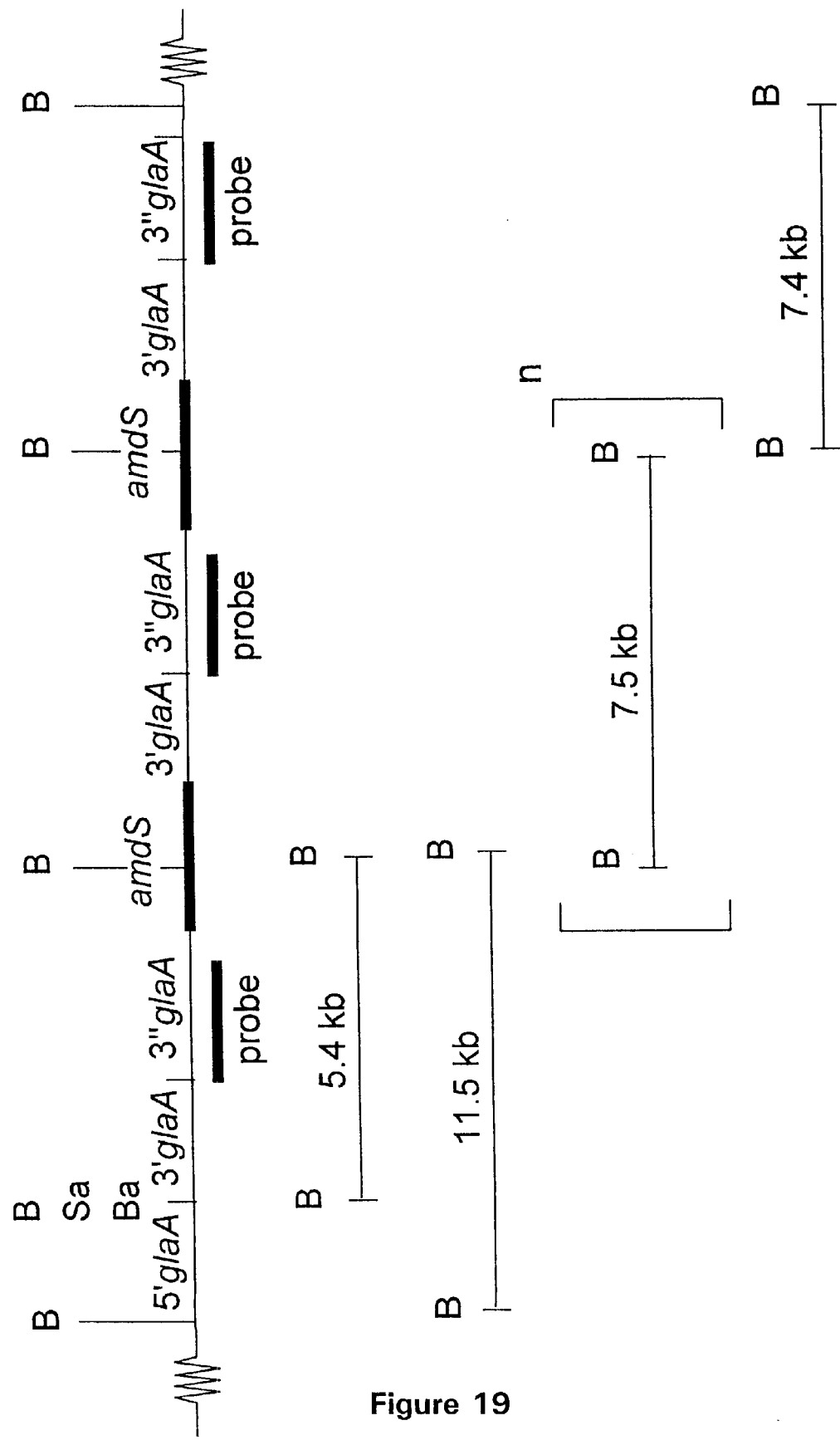

FIG. 19: Schematic illustration of the ΔglaA domains (each marked by B*, Sa* and Ba*) in pGBAAS-1/pGBTOPFYT-1 *A. niger* ISO-505 transformants, in which multiple amdS cassettes are targeted in one of three ΔglaA domains of the *A. niger* ISO-505 host. The hybridization pattern is shown of a BglII digest probed with the 2.2 kb SalI/XhoI 3"-glaA DNA fragment. Note that the prensence and intensity of the 7.5 kb BglII hybridizing fragment is dependend on the number (n) of integrated amdS cassettes.

Figure 20:
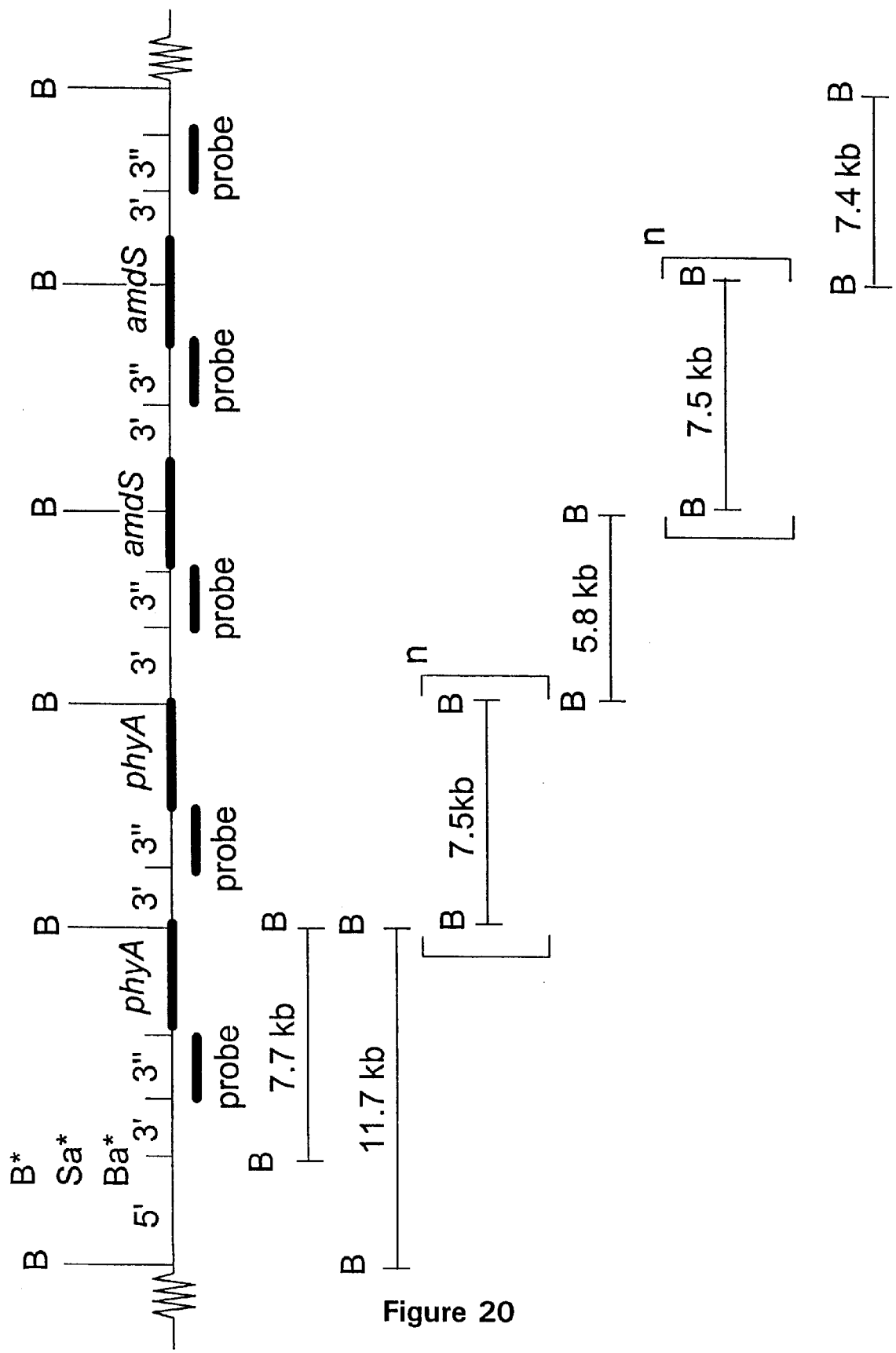

FIG. 20: Schematic illustration of the three ΔglaA domains (each marked by B*, Sa* and Ba*) in pGBAAS-1/pGBTOPFYT-1 *A. niger* ISO-505 transformants, in which multiple phyA has become integrated adjacent at the 3'-3"-glaA target sequence of one of three ΔglaA domains of the *A. niger* ISO-505 host and with in addition downstream one or multiple amdS cassettes. The hybridization pattern is shown of a BglII digest probed with the 2.2 kb SalI/XhoI 3"-glaA DNA fragment. Note that the intensity of the 7.5 kb BglII hybridizing fragment is dependend on the number (n) of integrated phyA and amdS cassettes.

Figure 21:
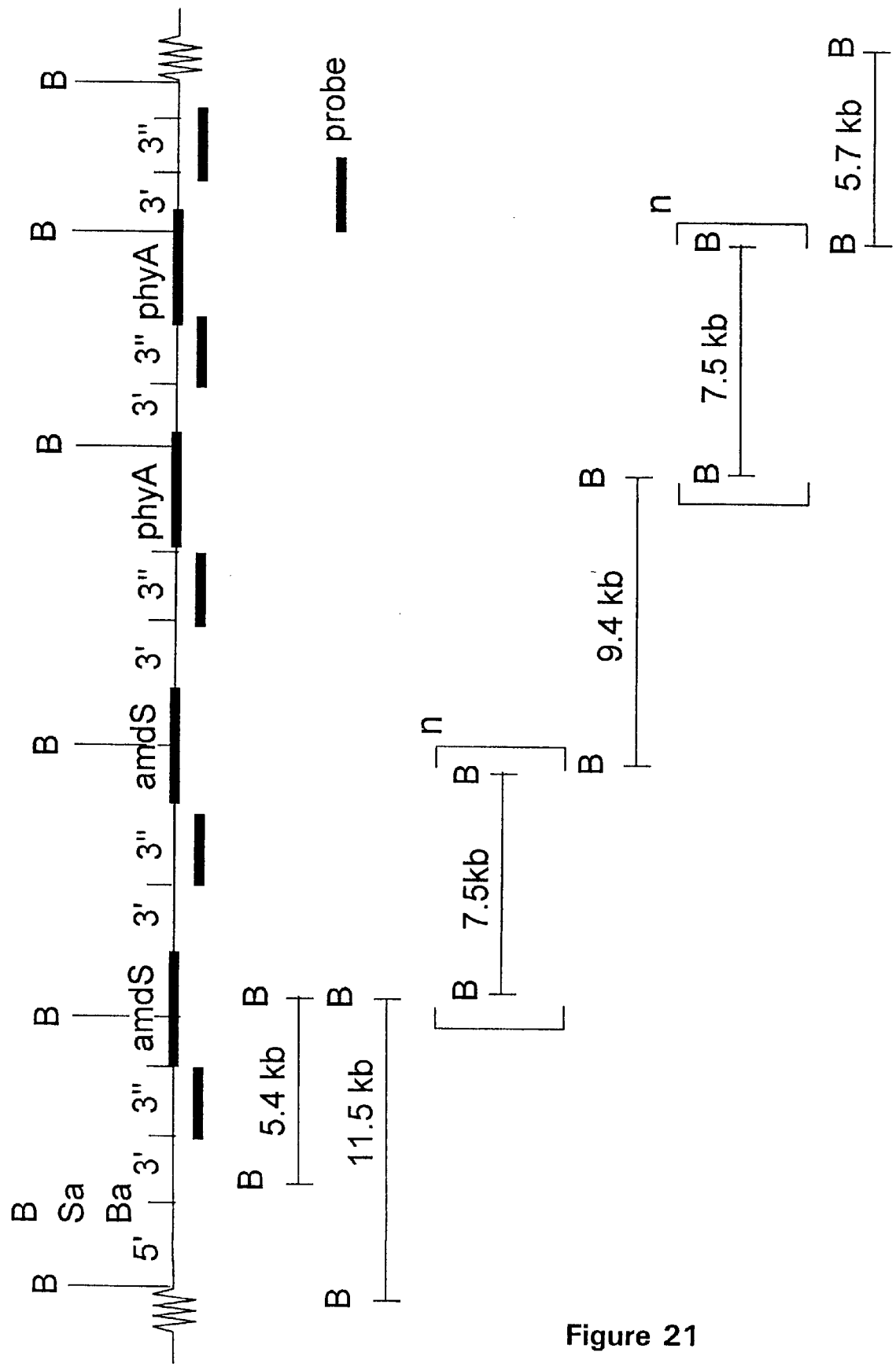

FIG. 21: Schematic illustration of the three ΔglaA domains (each marked by B*, Sa* and Ba*) in pGBAAS-1/pGBTOPFYT-1 A. niger ISO-505 transformants, in which multiple amdS cassettes are integrated adjacent at the 3'-3"-glaA target sequence of one of three ΔglaA domains of the A. niger ISO-505 host and with in addition downstream one or multiple phyA cassettes. The hybridization pattern is shown of a BglII digest probed with the 2.2 kb SalI/XhoI 3"-glaA DNA fragment. Note that the intensity of the 7.5 kb BglII hybridizing fragment is dependend on the number (n) of integrated phyA and amdS cassettes.

Figure 22:
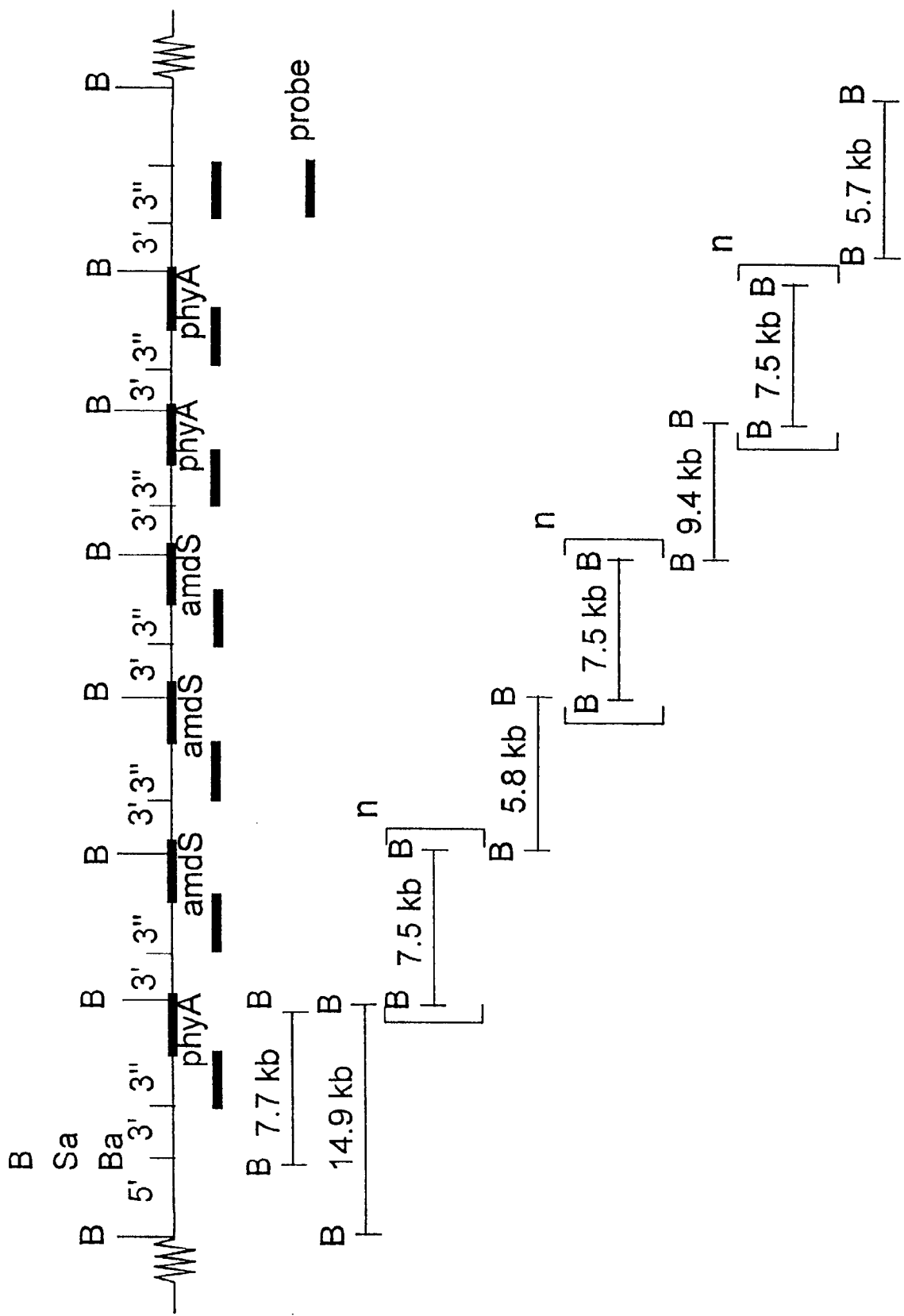

FIG. 22: Schematic illustration of the three ΔglaA domains (each marked by B*, Sa* and Ba*) in pGBAAS-1/pGBTOPFYT-1 A. niger ISO-505 transformants, in which multiple phyA cassettes are integrated adjacent at the 3'-3"-glaA target sequence of one of three ΔglaA domains of the A. niger ISO-505 host and with in addition downstream one or multiple phyA and amdS cassettes. The hybridization pattern is shown of a BglII digest probed with the 2.2 kb SalI/XhoI 3"-glaA DNA fragment. Note that the intensity of the 7.5 kb BglII hybridizing fragment is dependend on the number (n) of integrated phyA and amdS cassettes.

Figure 23:
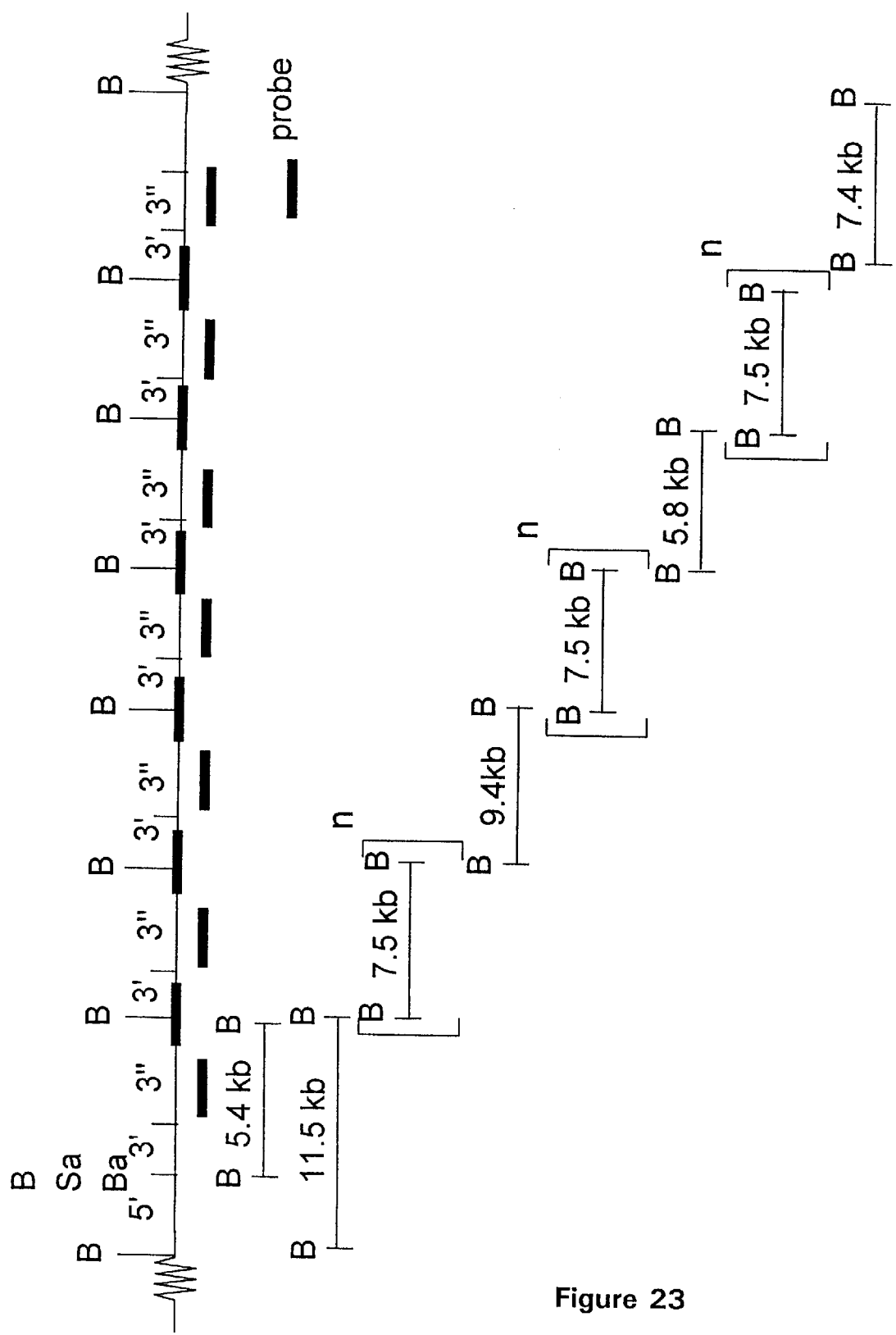

FIG. 23: Schematic illustration of the three ΔglaA domains (each marked by B*, Sa* and Ba*) in pGBAAS-1/pGBTOPFYT-1 A. niger ISO-505 transformants, in which multiple amdS cassettes are integrated adjacent at the 3'-3"-glaA target sequence of one of three ΔglaA domains of the A. niger ISO-505 host and in addition more downstream one or multiple amdS and phyA cassettes. The hybridization pattern is shown of a BglII digest probed with the 2.2 kb SalI/XhoI 3"-glaA DNA fragment.

FIGS. 24A–24B: Physical map of amdS gene free A. niger ISO-505 transformants containing one phyA copy (a), two phyA copies (b) and three phyA gene copies (c) targeted at the "BamHI-marked" ΔglaA locus. A schematic hybridization pattern is shown of BamHI and BglII digests, probed with 3"-glaA probe.

FIGS. 25A–25B: Schematic illustration of the three glaA domains in A. niger ISO-505-2 transformant, in which two phyA cassettes are targeted at the "BamHI-marked" ΔglaA amplicon showing the "DNA-flag" genotype BamHI$^+$/SalI$^+$/BglII$^+$ (A), BamHI$^{2+}$/SalI$^-$/BglII$^+$ (B) and BamHI$^{2+}$/SalI$^+$/BglII$^-$ (C). The hybridization patterns are shown of a BamHI digest probed with the 2.2 kb SalI/XhoI 3"-glaA DNA fragment. Note that the intensity of both BamHI hybridizing fragments is dependend on the presence and number of different amplicons.

FIGS. 26A–26B: Schematic illustration of the three glaA domains in A. niger ISO-505-2 transformant, in which two phyA cassettes are targeted at the "BamHI-marked" ΔglaA amplicon showing the "DNA-flag" genotype BamHI$^+$/SalI$^+$/BglII$^+$ (A), BamHI$^{2+}$/SalI$^-$/BglII$^+$ (B) and BamHI$^{2+}$/SalI$^+$/BglII$^-$ (C). The hybridization patterns are shown of a BglII digest probed with the 1.5 kb HindIII/XhoI 5'-glaA DNA fragment. Note that the intensity of BglII hybridizing fragments is dependend on the presence and number of different amplicons.

Figure 27:
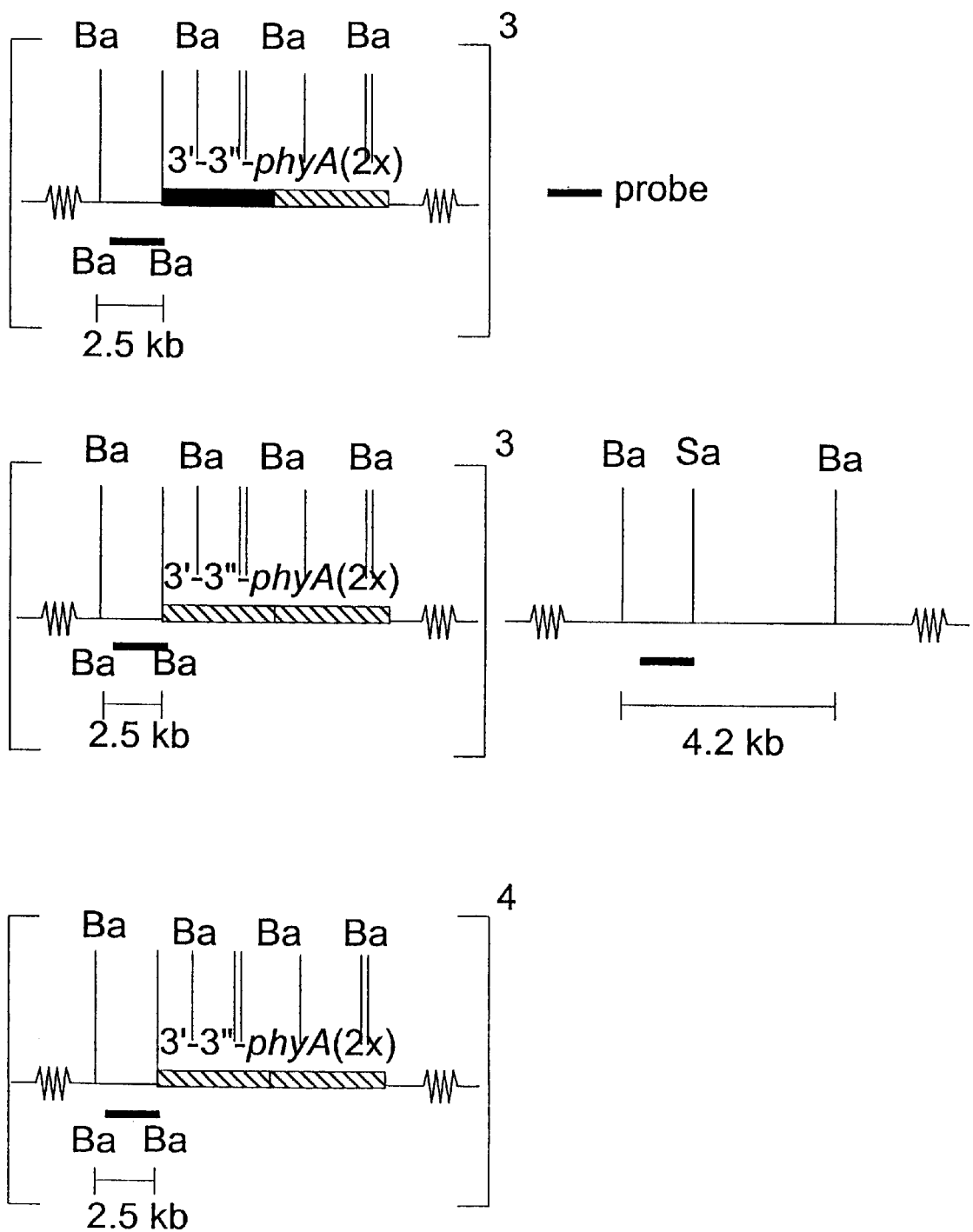

FIG. 27: Schematic illustration of the glaA domains in A. niger ISO-505-2 transformant, in which two phyA cassettes are targeted at the "BamHI-marked" ΔglaA amplicon, showing the "DNA-flag" genotype BamHI$^{3+}$/SalI$^-$/BglII$^-$ (A), BamHI$^{3+}$/SalI$^+$/BglII$^-$ (B) and BamHI$^{4+}$/SalI$^-$/BglII$^-$ (C). The hybridization pattern is shown of a BamHI digest probed with the 1.5 kb HindIII/XhoI 5'-glaA DNA fragment. Note that the intensity of both BamHI hybridizing fragments is dependend on the presence and number of different amplicons.

FIG. 28: Schematic illustration of the glaA domains in A. niger ISO-505-2 transformant, in which two phyA cassettes are targeted at the "BamHI-marked" ΔglaA amplicon, having the "DNA-flag" genotype BamHI$^{3+}$/SalI$^-$/BglII$^-$ (A), BamHI$^{3+}$/SalI$^+$/BglII$^-$ (B) and BamiHI$^{4+}$/SalI$^-$/BglII$^-$ (C). The hybridization pattern is shown of a BglII digest probed with the 2.2 kb SalI/XhoI 3"-glaA DNA fragment. Note that the intensity of both BamHI hybridizing fragments is dependend on the presence and number of different amplicons.

Figure 29:
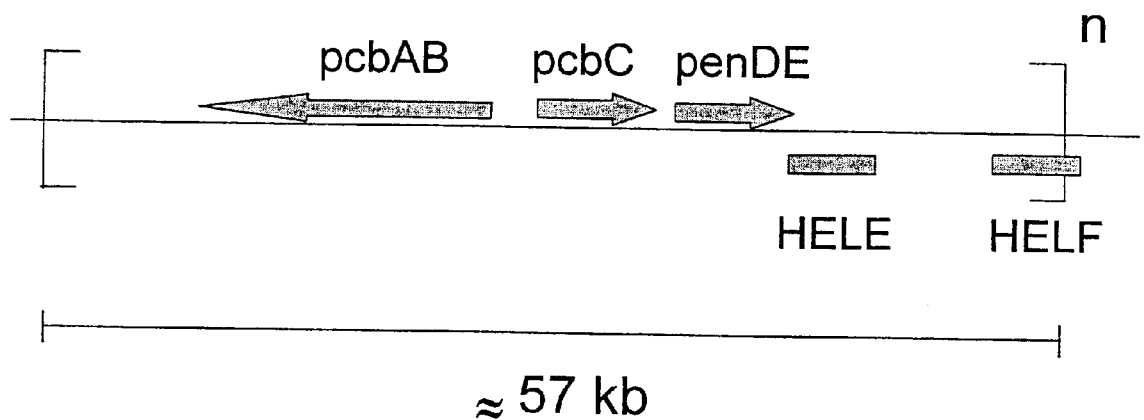

FIG. 29: PEN amplicons in P. chrysogenum. Relative positions of the penicillin biosynthetic genes, HELE and HELF, within a single amplicon (between brackets). Multiple PEN amplicons are present as direct reapeats (n). Note that the 3' end of HELF extends into the adjacent PEN amplicon.

FIGS. 30A–30B: Quantitation of PEN amplicons by Southern analyses. Relative positions of BstXI sites, probes and sizes of the expected hybridization fragments from the niaD locus (A) and PEN amplicon (B) The amount of DNA hybridizing to the HELE probe depends on the number of PEN amplicons (n).

Figure 31:
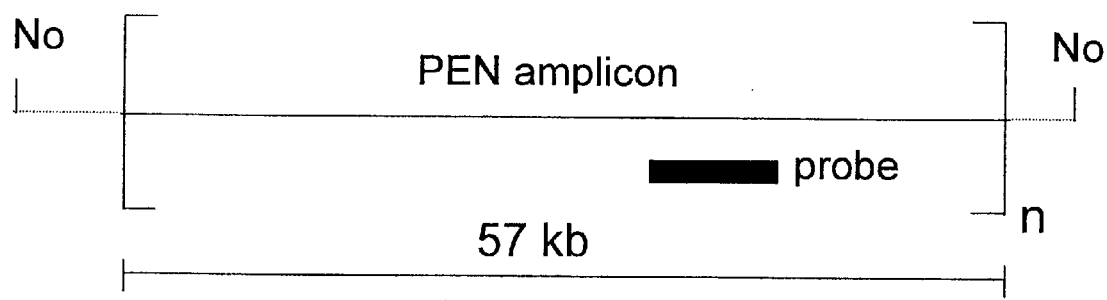

FIG. 31: Quantitation of PEN amplicons by CHEF. Relative positions of NotI sites and HELE probe are indicated. The NotI sites are located outside the PEN amplicon. The expected sizes of hybrizing fragments depend on the number of PEN amplicons (30+n×57) kb.

FIGS. 32A–32C: Targeted integration. (A) Expression vectors contain the gene of interest, regulated by a suitable promoter (P) and terminater (T). The cassette is flanked by 5" and 3" regions homologous to the target site (" and ' to distinguish vector sequence from genomic sequence, respectively). Cassette and flankings are cloned in an E. coli vector for propagation of the expression vector. Prior to transformation, the expression vector is digested with restriction enzyme R to create a linear fragment and remove the E. coli sequence. (B) Integration occurs at the homologous region in the genome with the free 5' and 3' ends of the transformation fragment as hot spot for recombination. (C) Resulting transformant contains 1 or multiple copies (n) of the transformation fragment (between brackets) integrated at the target site.

Figure 33:
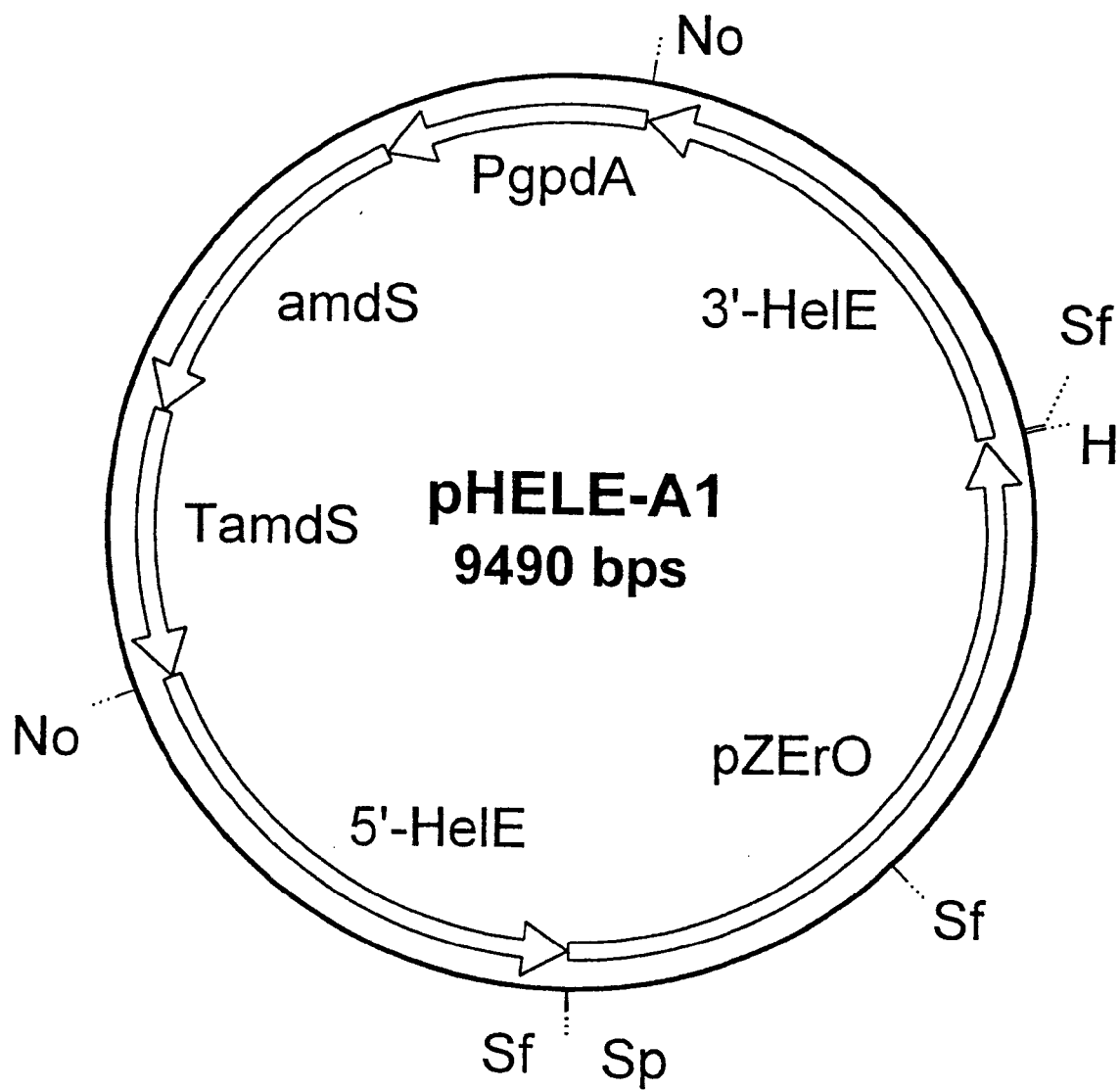

FIG. 33: Expression vector pHELE-A1. The transformation fragment, comprising the amdS expression cassette flanked by 5' and 3' regions of HELE, was isolated as a SfiI fragment. These sites were introduced via the oligo's used to PCR the corresponding flankings.

Figure 34:
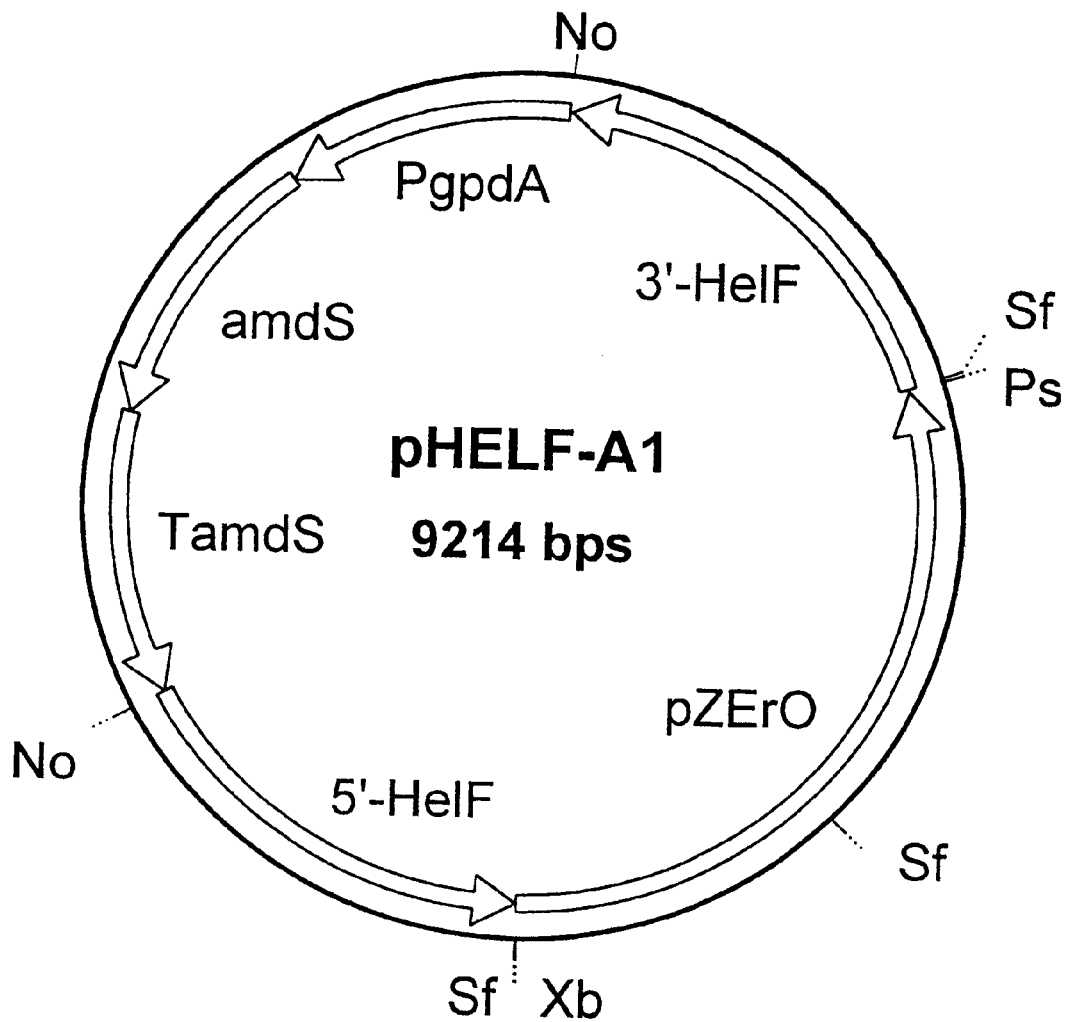

FIG. 34: Expression vector pHELF-A1. The transformation fragment, comprising the amdS expression cassette flanked by 5' and 3' regions of HELF, was isolated as a SfiI fragment. These sites were introduced via the oligo's used to PCR the corresponding flankings.

Figure 35:
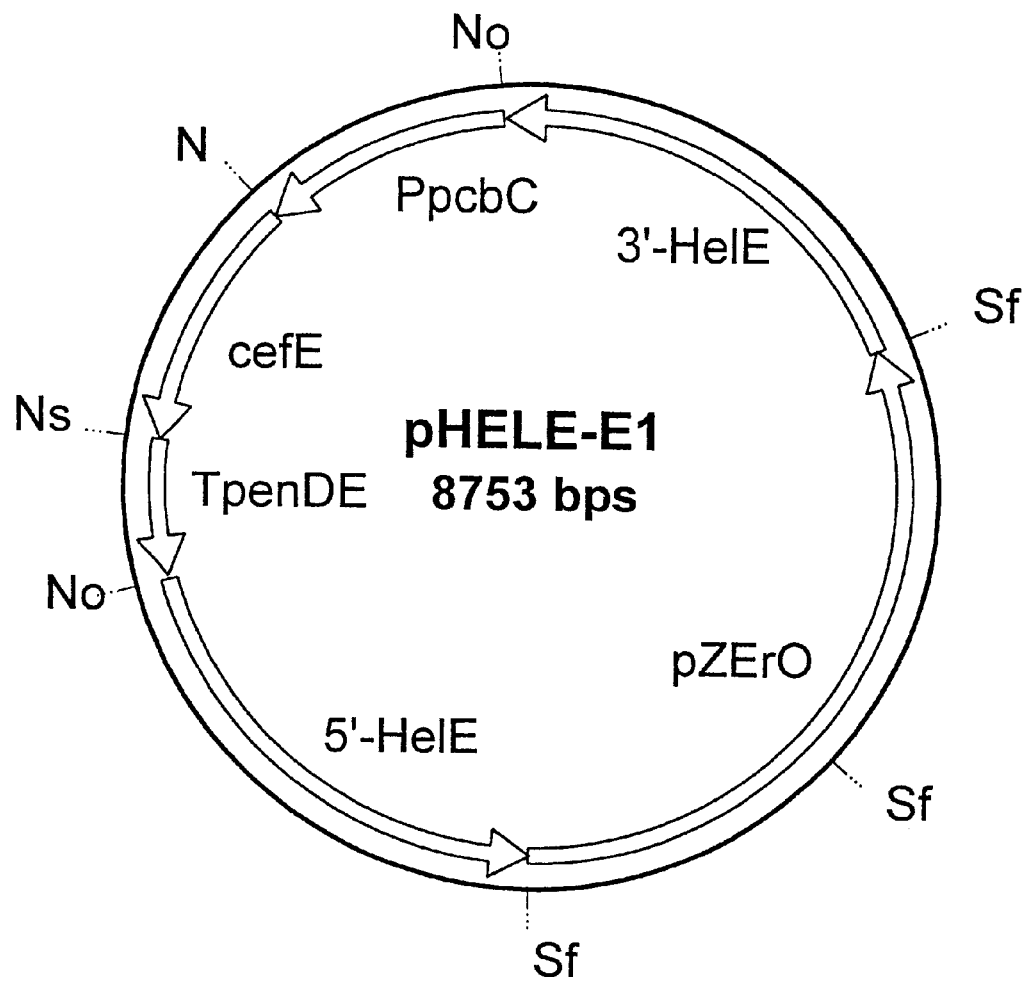

FIG. 35: Expression vector pHELE-E1. The transformation fragment, comprising the cefE expression cassette flanked by 5' and 3' regions of HELE, was isolated as a SfiI fragment.

Figure 36:
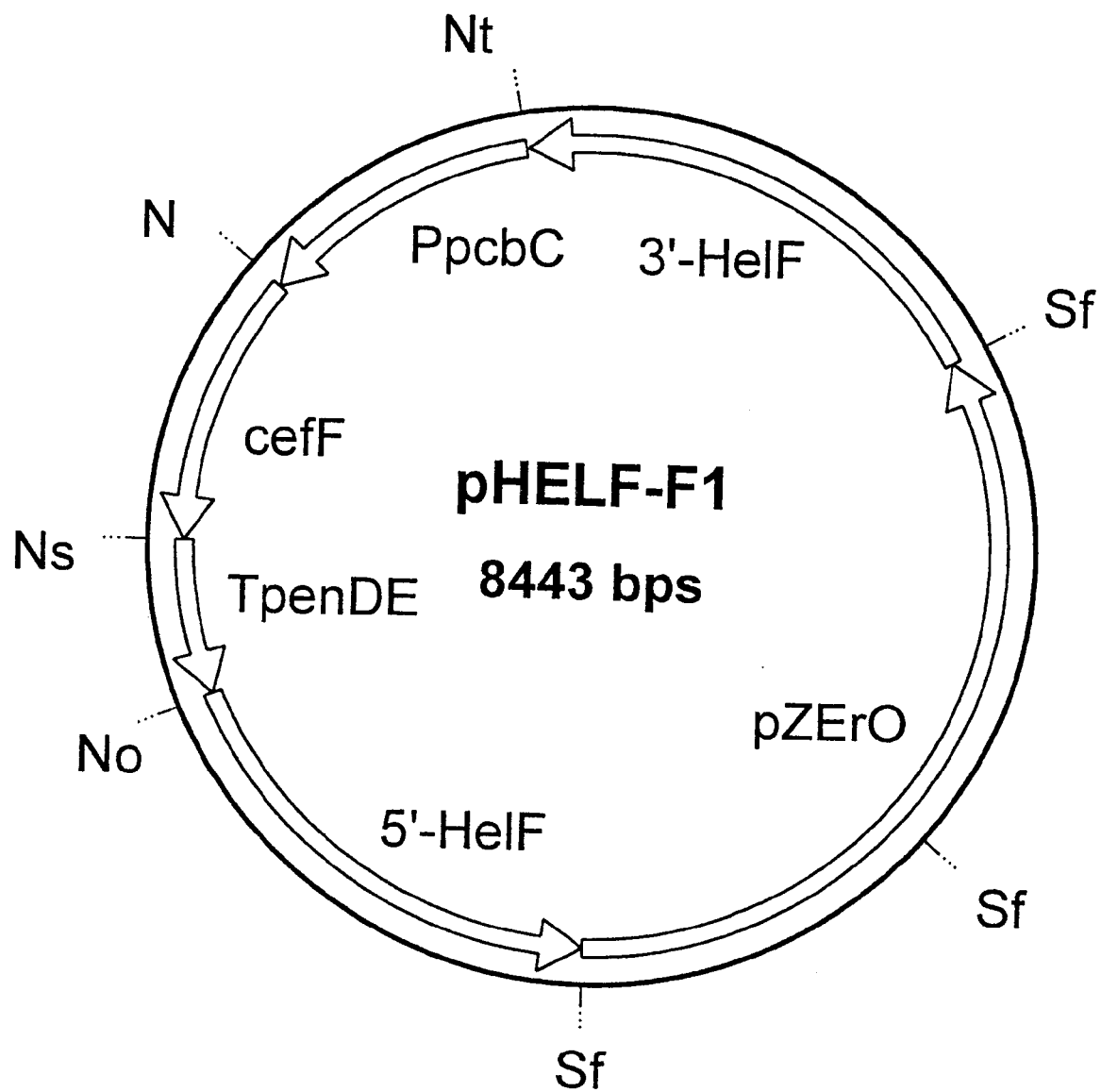

FIG. 36: Expression vector pHELF-F1. The transformation fragment, comprising the cefF expression cassette flanked by 5' and 3' regions of HELE, was isolated as a SfiI fragment.

FIGS. 37A–37B: Loss of amdS through recombination. (A) Direct repeats of the 5' and 3' flankings arise by tandem integration of expression cassettes. (B) The 5' and 3' flankings pair and recombination occurs through a single cross-over. (C) The region between site of cross-over is lost. Note that any number of cassettes (including the genes of interest) can be lost, since all are flanked by direct repeats.

FIGS. 38A–38B: Integration of cefE in HELE. Physical map of (A) single or (B) multiple cefE cassettes in HELE. Relative positions of NruI sites, cefE probe and expected sizes of hybridizing fragments are indicated. The 6.0 kb fragment occurs by multiple integrations of the cassette and its intensity depends on the number of cassettes present (n).

Figure 39:
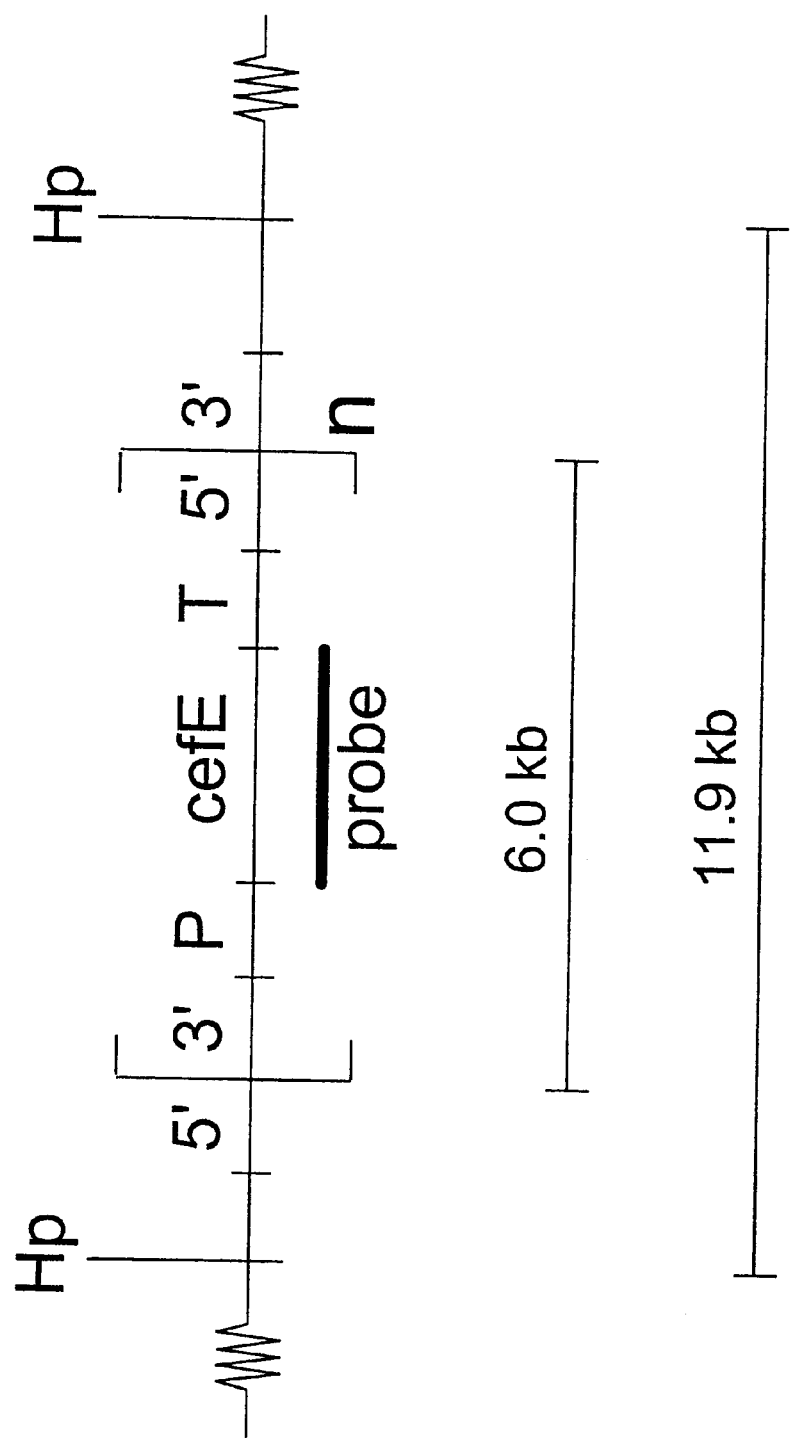

FIG. 39: Integration of cefE in HELE determined by TAFE. Relative positions of HpaI sites, probe and expected sizes of hybridizing fragments are indicated. The size of the hybridizing fragment depends on the number (n) of cassettes integrated (5.9+n×6.0) kb.

FIGS. 40A–40K: Cassette and targeting PCR. Schematic presentation of specific template and oligo combinations. Essential for targeting PCR is that one oligo is located upstream of the 5' flanking. Hence, although several cassettes can be present, only the cassette 3' of this oligo yields a PCR product. Relevant domains, oligo's and expected sizes of PCR products are indicated. (A) Cassette PCR of cefE, (B) Targeting PCR of cefE in HELE, (C) Targeting PCR of amdS in HELE, (D) cassette PCR of amdS, (E) targeting PCR of cefE-amdS combination (F) targeting PCR of amdS-cefE combination (G) targeting PCR of amdS-amdS combination (H) cassette PCR of niaD locus (I) cassette PCR of cefF (J) targeting PCR of cefF integrated in HELF (K) targeting PCR of amdS integrated in HELF.

Figure 41:
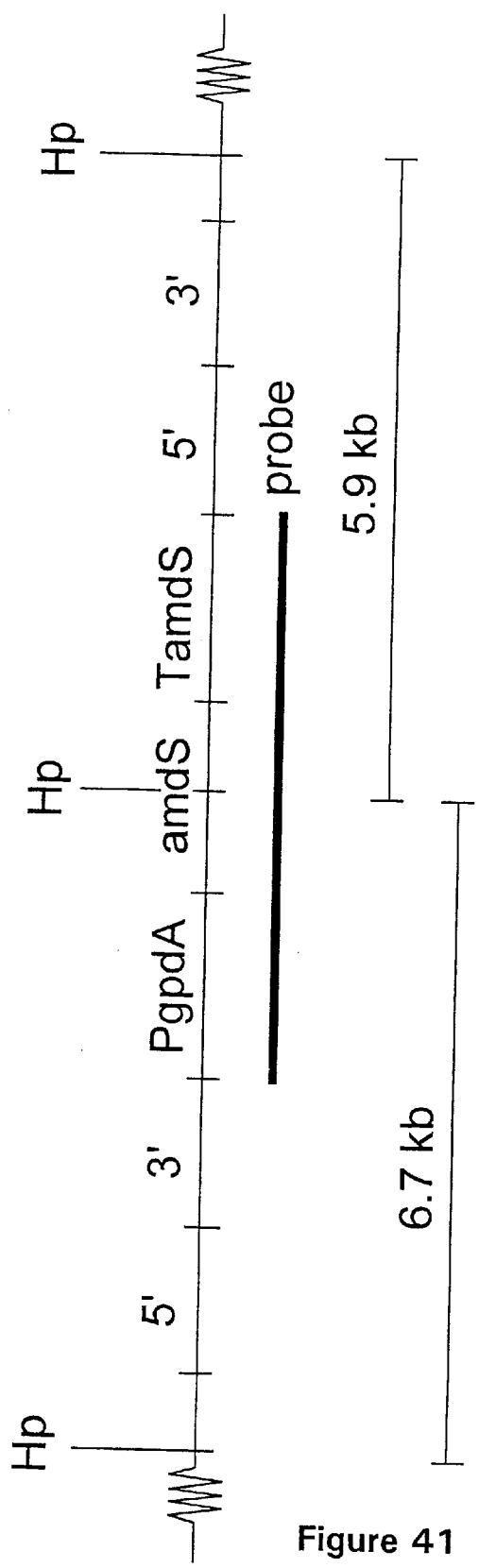

FIG. 41: Integration of amdS in HELE. Relative positions of HpaI sites, amdS probe and expected sizes of the hybridizing fragments are indcated.

FIGS. 42A–42E: Probes. DNA fragments isolated for preparation of probes: (A) cefE probe: NdeI-NsiI fragment of pHEL-E1. (B) cefF probe: NdeI-NsiI fragment of pHEL-F1. (C) amdS probe: NotI fragment of pHELE-A1. (D) HELE probe: SpHI-NotI fragment of pHELE-A1. (E) niaD probe: PCR product of oligo's 28 and 29 with chromosomal *P. chrysogenum* DNA as template.

Figure 43:
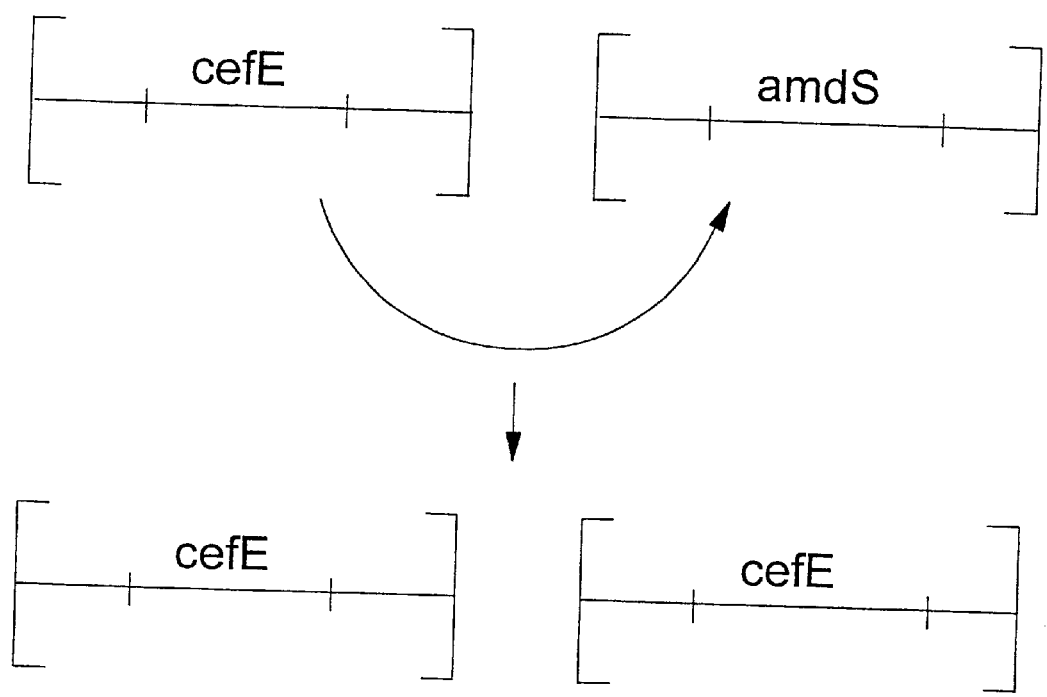

FIG. 43: Gene conversion. Gene conversion and resulting duplication of cefE through substitution of amdS by cefE in another PEN amplicon (between brackets).

Figure 44:
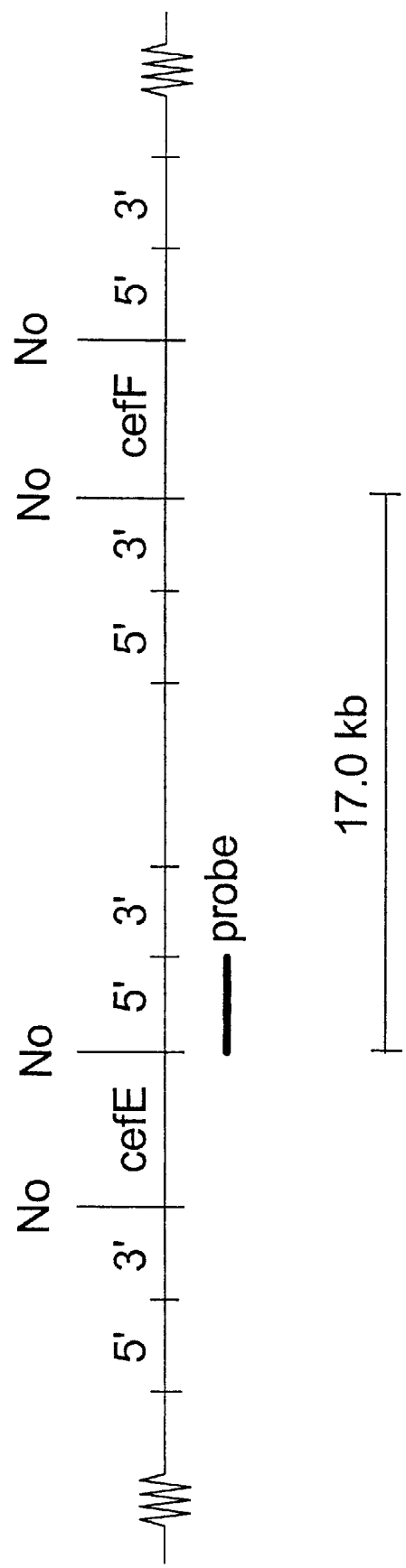

FIG. 44: Integration of (cefE+cefF) in one amplicon. Relative positions of NotI sites, HELE robe and expected sizes of hybridizing fragments, specific for integration of cefE in HELE and cefF in HELF on the same amplicon, are indicated. Note that NotI site are incorporated via integration of cefE and cefF cassettes.

Figure 45A:
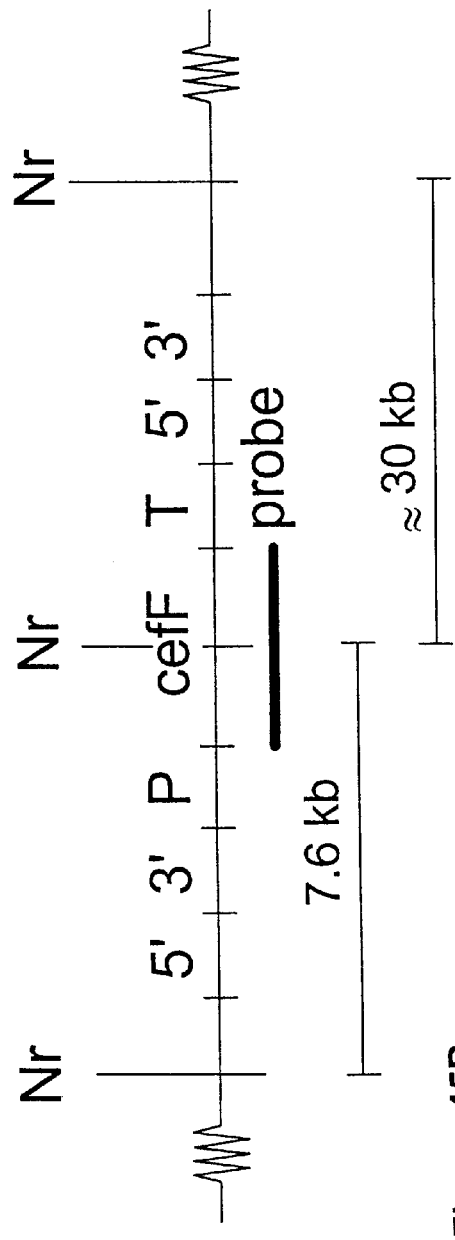
Figure 45B:
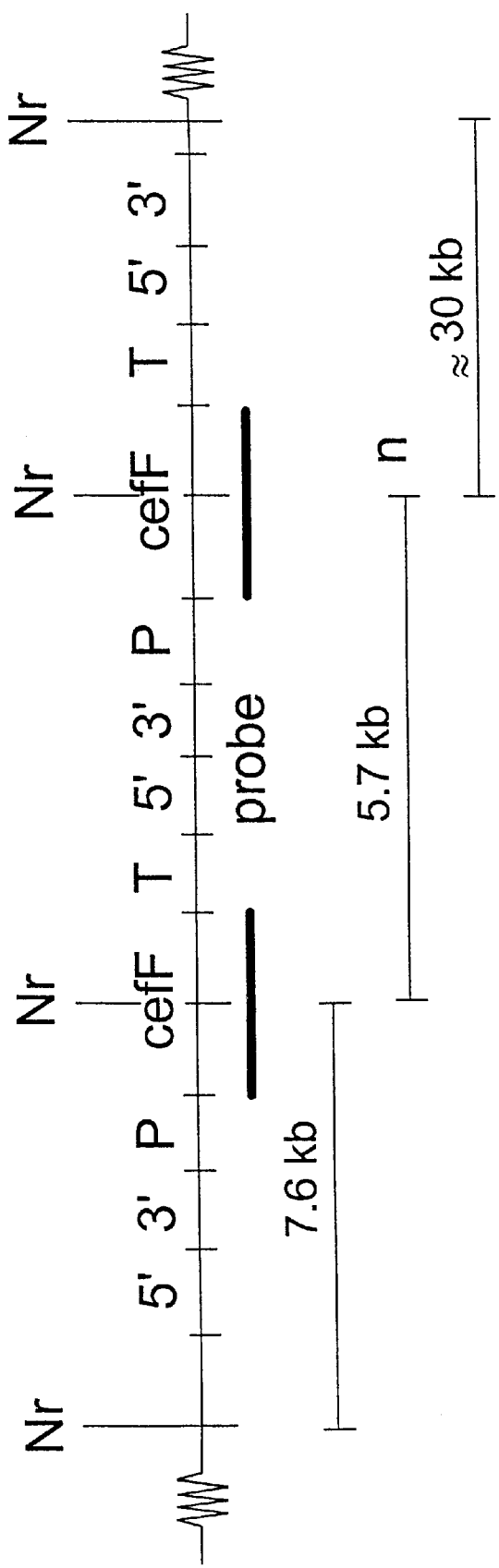

FIGS. 45A–45B: Integration of cefF in HELF. Physical map of (A) single or (B) multiple cefF cassettes in HELF. Relative positions of NruI sites, cefF probe and expected sizes of hybridizing fragments are indicated. The 5.7 kb fragment occurs by multiple integrations of the cassette and its intensity depends on the number of cassettes present (n).

Figure 46A:
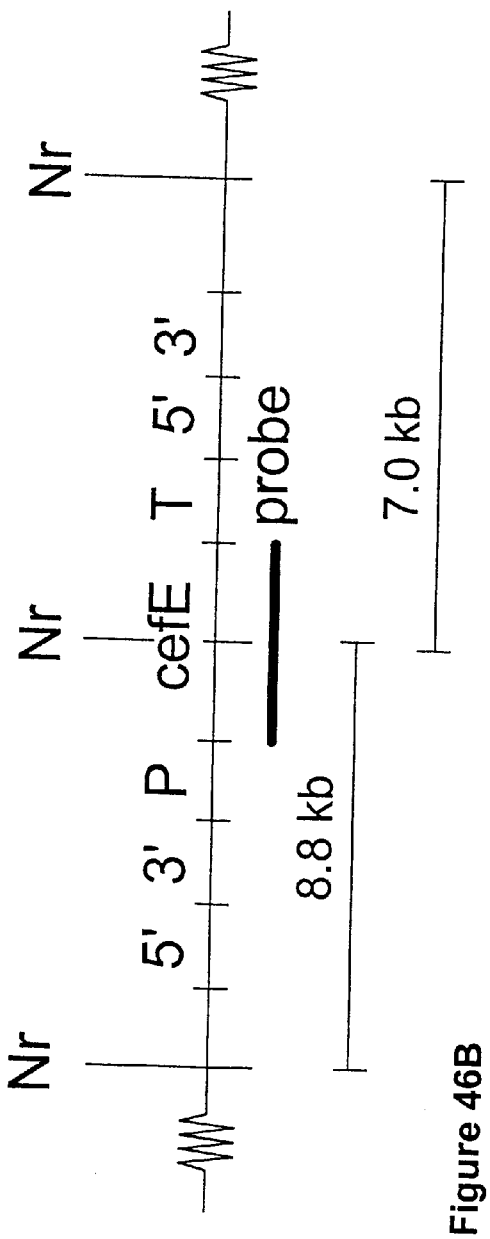
Figure 46B:
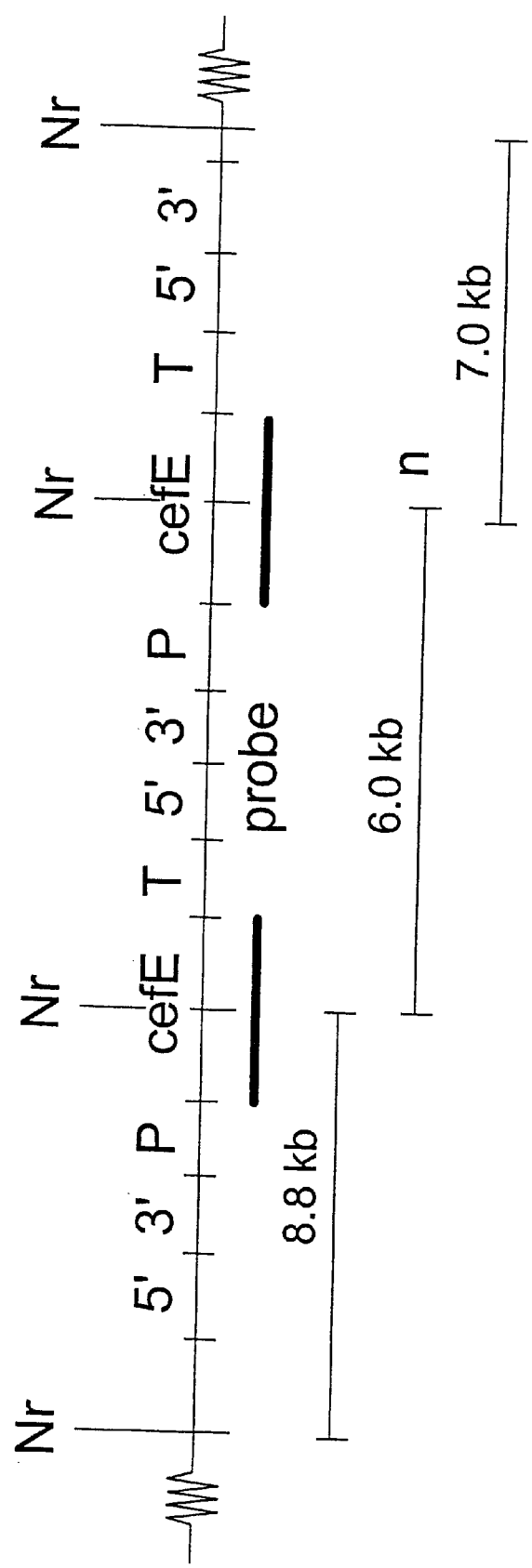
Figure 46C:
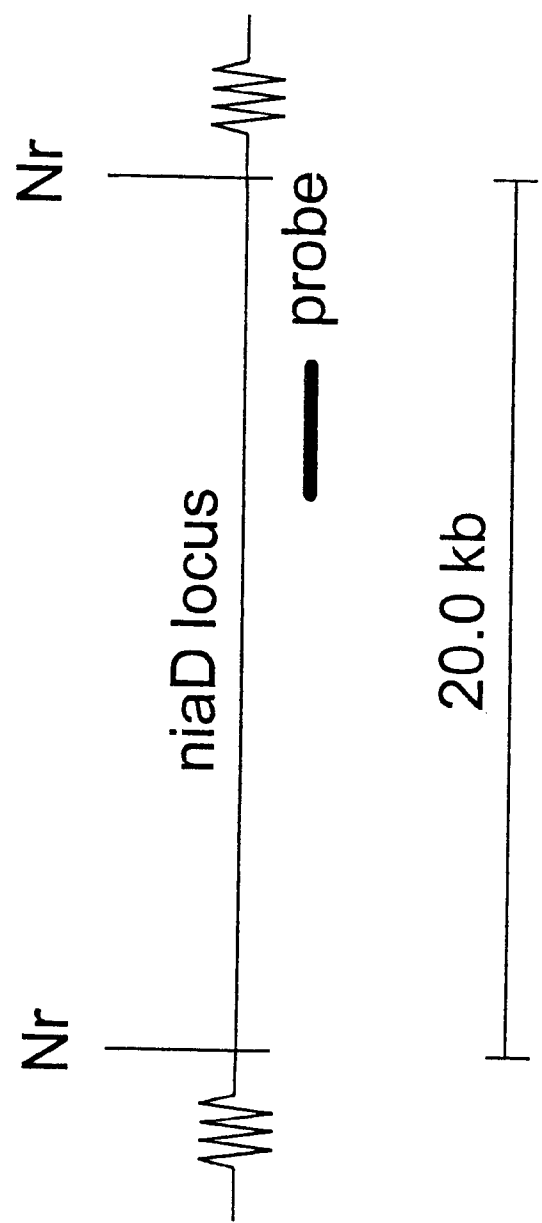

FIGS. 46A–46C: Quantitation of cefE in (cefE+cefF) gene convertants. Relative positions of NruI sites, probes and expected sizes of hybridizing fragments for (A) single or (B) multiple cefE cassettes in HELE. The 6.0 kb fragment occurs by multiple integrations of the cassette and its intensity depends on the number of cassettes present (n). (C) niaD locus. Gene convertants will have a hybridization is pattern identical to the parental strain but increased intensity relative to the niaD signal.

Figure 47A:
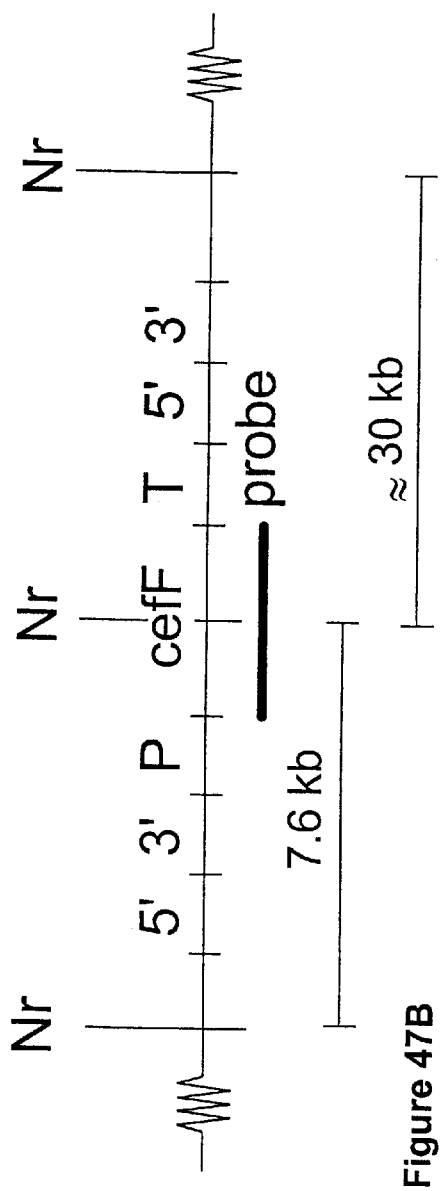
Figure 47B:
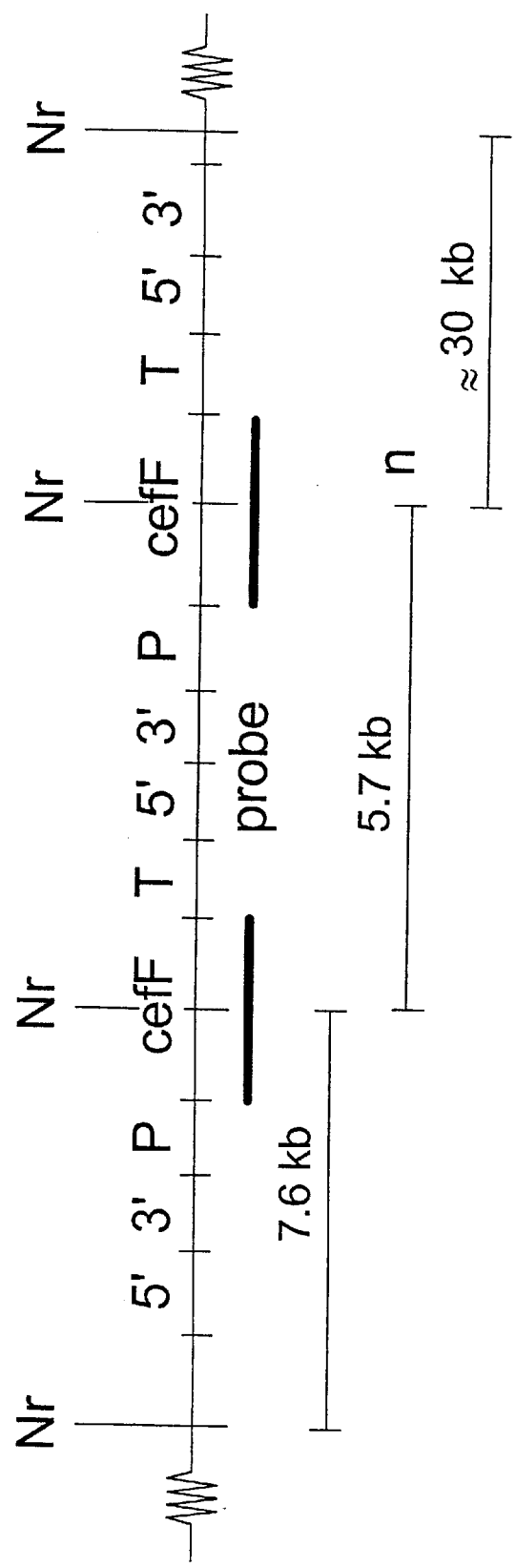
Figure 47C:
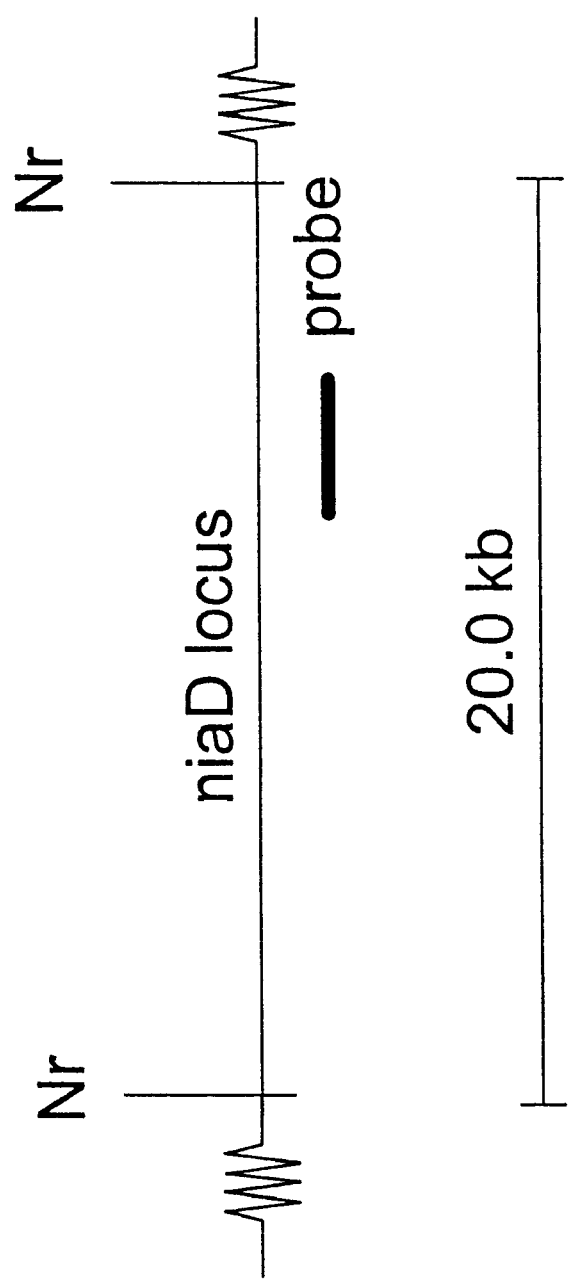

FIGS. 47A–47C: Quantitation of cefF in (cefE+cefF) gene convertants. Relative positions of NruI sites, probes and expected sizes of hybridizing fragments for (A) single or (B) multiple cefF cassettes in HELF. The 5.7 kb fragment occurs by multiple integrations of the cassette and its intensity depends on the number of cassettes present (n). (C) niaD locus. Gene convertants will have a hybridization pattern identical to the parental strain but increased intensity relative to the niaD signal.

Figure 48A:
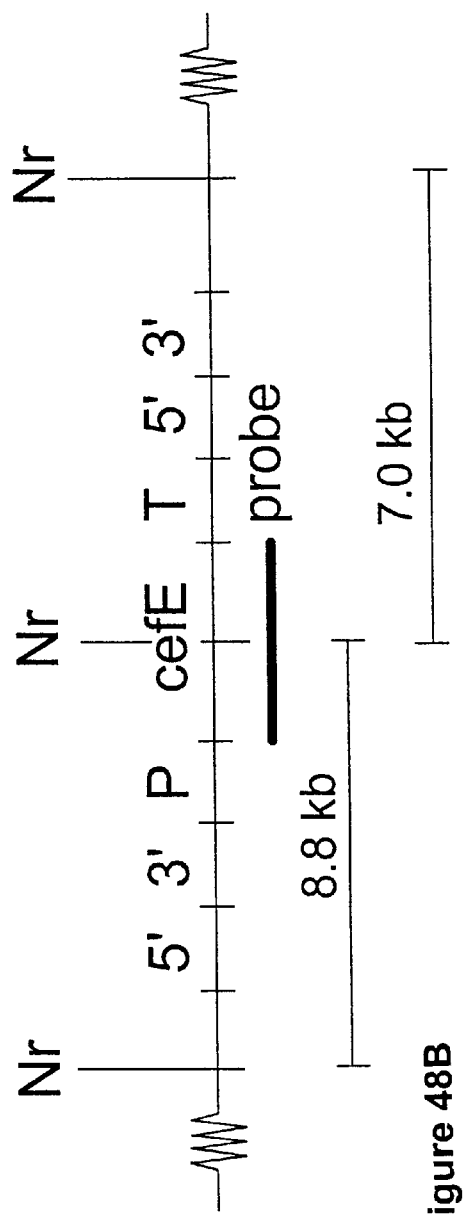
Figure 48B:
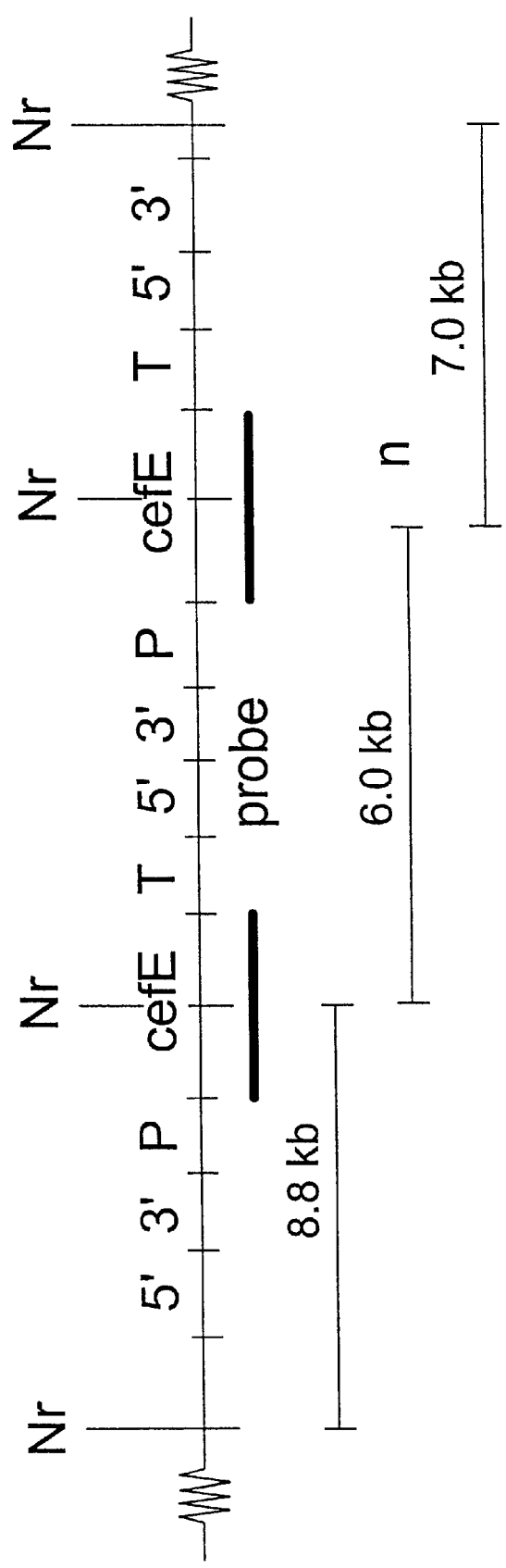
Figure 48C:
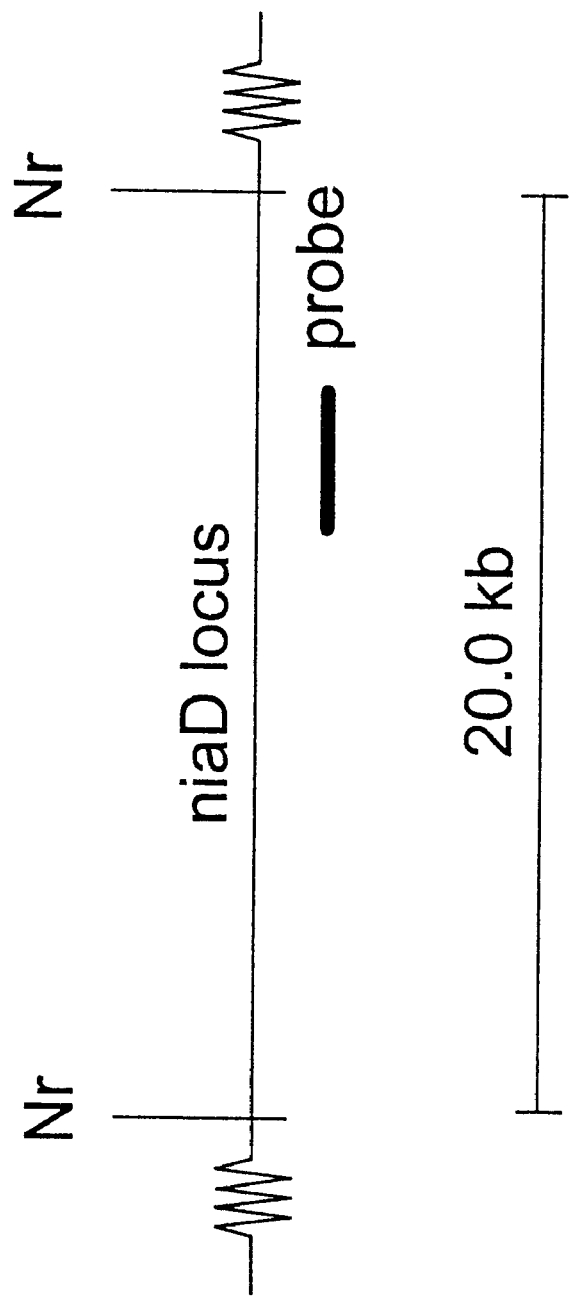

FIGS. 48A–48C: Quantitation of cefE gene convertants. Relative positions of NruI sites, probes and expected sizes of hybridizing fragments for (A) single or (B) multiple cefe cassettes in HELE. The 6.0 kb fragment occurs by multiple integrations of the cassette and its intensity depends on the number of cassettes present (n). (C) niaD locus. Gene convertants will have a hybridization pattern identical to the parental strain but increased intensity relative to the niaD signal.

DESCRIPTION OF THE INVENTION

In a first aspect the present invention relates to a filamentous fungus which has integrated a recombinant DNA molecule into at least two substantially homologous DNA domains of its chromosome(s), wherein the DNA domains are not the ribosomal DNA repeats. Filamentous fungi of the invention are prepared by transforming a filamentous fungus with at least two such DNA domains in its genome with a recombinant DNA molecule and identification of a transformant with at least one recombinant DNA molecule integrated in at least one of the DNA domains and by subsequent identification of strains in the progeny of the transformant, which the DNA domain comprising the recombinant DNA molecule has multiplied through gene conversion with the other versions of the DNA domain or through amplification of the DNA domain comprising the recombinant DNA molecule. In other words, the filamentous fungus of the invention has incorporated at least one recombinant DNA molecule in at least one of its endogenous DNA domains in its genome.

The filamentous fungi of the present invention are eukaryotic microorganisms and include all filamentous forms of the division Eumycota of the kingdom of fungi (see e.g. Lasure and Bennett, 1985, Fungal Taxonomy, In: gene manipulations in Fungi, pp 531–535, Academic Press, Inc.). The filamentous fungi of the present invention are morphologically, physiologically and genetically distinct from yeast: in contrast to yeasts such as *S. cerevisiae*, vegetative growth of filamentous fungi is by hyphal elongation and carbon metabolism is obligately aerobic. Moreover, yeasts like *S. cerevisiae* have a prominent stable diploid phase whereas in filamentous fungi like e.g. *Aspergillus nidulans* and *Neurospora crassa* diploids only exist briefly prior to meiosis. In addition, many industrially important filamentous fungi belong to the subdivision of Deuteromycotina, also referred to as the Fungi Imperfecti, an artificial group of fungi that are distinguished by the absence of any known sexual form. Preferred filamentous fungi of the invention belong to the genera of Aspergillus, Trichoderma, Penicillium, Cephalosporium, Acremonium, Fusarium, Mucor, Rhizophus, Phanerochaete, Neurospora, Humicola, Claviceps, Sordaria, Ustilago, Schizophyllum, Blakeslea, Mortierella, Phycomyces and Tolypocladium. The most preferred filamentous fungi of the invention are fungi which belong to the *Aspergillus niger* group as defined by Raper and Fennell (1965, In: The genus Aspergillus, The Williams & Wilkins Company, Baltimore), e.g. *A.niger*, the *Aspergillus flavus* group as defined by Raper and Fennell (supra), e.g. *A. oryzae*, as well as the fungi *Trichoderma reesei* and *Penicillium chrysogenum*. The invention is exemplified by the filamentous fungi *A. niger* and *P. chrysogenum*.

The filamentous fungi according to the invention comprise in their genome at least two substantially homologous versions of a DNA domain suitable for integration of one or more copies of a recombinant DNA molecule, wherein the DNA domain is non-ribosomal DNA. In the examples herein the amplified glucoamylase (glaA) locus of A. niger and the amplified penicillin cluster of P. chrysogenum are used as DNA domains for integration of the recombinant DNA molecules. Both the glaA locus of A. niger and the penicillin cluster of P. chrysogenum, comprising the penicillin biosynthetic genes pcbAB, pcbc and penDE, occur in a single copy in genomes of wild type A. niger and P. chrysogenum strains, respectively. Strains containing multiple copies of these DNA domains, as used in the present examples, can be obtained in classical strain improvement programs by selecting for strains with improved glucoamylase or penicillin production, respectively. Frequently, such production improvements are the result of amplification of a DNA domain in the selected strains. Such amplified DNA domains are referred to as amplicons hereinafter. Although the present invention preferably uses such amplicons as DNA domains for the integration of the recombinant DNA molecules, the invention is by no means limited thereto. In fact, any DNA domain of which two or more substantially homologous versions occur in the genome of a filamentous fungus can be used as long as two functional criteria are fulfilled: 1) the DNA domain should be suitable for accepting the integration of a recombinant DNA molecule; 2) the DNA domain should be capable of recombination with the other substantially homologous versions of the domain in the fungal genome in order to achieve multiplication of the integrated recombinant DNA molecule through gene conversion.

In order to meet the first criterium, a DNA domain must be of sufficient length in order to allow targeting of the recombinant DNA molecule into the domain through homologous recombination. For this purpose a DNA domain should comprise at least 100 bp, preferably at least 1 kb and more preferably at least 2 kb. The suitability of a DNA domain for integration therein of a recombinant DNA molecule is furthermore determined by the requirement that integration into the DNA domain should not disrupt functions that are essential for the viability of the filamentous fungus in question.

For the second functional criterium, i.e. the capability of recombination with the other substantially homologous versions of the domain in the fungal genome, is required for allowing gene conversions between the different versions of the DNA domain. The minimal requirement for this purpose is that each version of the domain is flanked on either end of the domain by DNA sequences that are sufficiently homologous to the corresponding flanking sequences of the other version of the DNA domains so as to allow homologous recombination between the flanking sequences. The result of this homologous recombination being a gene conversion wherein one of the versions of the DNA domain is replaced by a duplicated version of the other DNA domain containing the integrated recombinant DNA molecule. The minimum requirements regarding length and extend of homology of the flanking sequences still allowing gene conversion is not exactly known and may vary depending on the organism in question. Probably a minimum length of 100 bp with an overall homology at least 60% will still allow gene conversion. Obviously the frequency of gene conversion will increase with increasing length and homology of the sequences flanking the DNA domain. Preferably the different domains are flanked by sequences of at least 1 kb which share at least 80% homology. The fungal genome may contain one or different types of DNA domains as defined above. Examples of different types of such domains which are not perfect copies of each other are allelic variants, gene families and/or genes encoding isoenzymes. Most preferred are domains which are exact copies of each other, differing at most in the presence of the integrated recombinant DNA molecule. Examples of such identical domains are amplicons. Thus, in a preferred embodiment of the invention, said DNA domains suitable for integration of one or more copies of a recombinant DNA molecule are amplicons.

The overall length of the DNA domains is not important and may vary from less than 1 kb to several hundreds of kb's, e.g. in the examples herein the length of the DNA domains ranges from about 57 kb per unit for the amplified penicillin cluster to more than 80 kb per unit for the amplified glaA locus.

The recombinant DNA molecule comprises any combination of genetic elements required to introduce a desired genetic modification in the filamentous fungi of the invention. The recombinant DNA molecule comprises any genetic element, parts thereof or combinations thereof, such as a gene (coding part or complete locus), a cDNA, a promoter, a terminator, an intron, a signal sequence, any regulatory DNA sequence or recognition sequence of DNA-binding proteins. The genetic elements may also include DNA sequences that have been modified i.e. containing one or more nucleotide alterations (e.g. insertions, deletions, substitutions).

The desired genetic modifications include any modification, i.e. insertions, deletions, and/or substitutions of DNA sequences in a selected filamentous fungus which are the result of the introduction of one or more of the above mentioned genetic elements into the fungus by transformation or co-transformation of the recombinant DNA molecule. It will be understood that several such genetic modifications can be introduced in independent rounds of transformation.

According to one embodiment of the invention, the recombinant DNA molecule integrated in the DNA domain of the filamentous fungus contains one or more expression cassettes for the expression of one or more desired genes. An expression cassette is herein understood to mean a DNA fragment comprising a desired gene to be expressed and which is operably linked to the appropriate expression elements that are capable of effecting and regulating the expression of the gene. Such expression elements include promoters, signal sequences, terminators and the like.

If the filamentous fungus is intended for the production of proteins or enzymes either heterologous or homologous, the desired gene preferably encodes a secreted protein or enzyme and thus comprises a signal sequence effecting the secretion of the enzyme. This embodiment is e.g. exemplified herein by the integration of expression cassettes comprising the A.niger phytase gene in the A.niger glaA amplicons. However, it will be clear to the skilled person that the invention is applicable to any protein or enzyme of interest.

Alternatively, if the filamentous fungus is intended for the production of primary or secondary metabolites, the desired genes will usually encodes one or more intracellular enzymes that are involved in the biosynthesis of these metabolites. In a preferred embodiment according to this aspect of the invention, the filamentous fungus comprises one or more recombinant DNA molecules integrated in the DNA domain, whereby the recombinant DNA molecules comprises one or more expression cassettes for intracellular enzymes that are part of a metabolic pathway which is not native to the filamentous fungus. Examples of such filamentous fungi include e.g. *P.chrysogenum* strains which have integrated in their penicillin amplicons expression cassettes for a deacetoxycephalosporin C synthetase (expandase) and a deacetylcephalosporin C synthetase (hydroxylase), allowing these strains to synthesize adipoyl-7-aminodeacetoxycephalosporanic acid and adipoyl aminodeacetylcephalosporanic acid, respectively.

The mechanism by which the recombinant DNA molecule integrates in the DNA domain is not important for the invention and may depend on the application of the invention at hand. Integration of the recombinant DNA molecule in the DNA domain can occur by random integration but more preferably integration occurs by homologous recombination, either by a single cross-over recombination event, i.e. resulting in an insertion of the recombinant DNA molecule, or by a double cross-over recombination event, resulting in a replacement by the recombinant DNA molecule, substituting part of the original sequences of the DNA domain. In order to promote integration through homologous recombination the recombinant DNA preferably contains sequences that are homologous to the target sequences for integration in the DNA domain. Preferably such targeting sequences in the recombinant DNA molecule are identical to the target sequence in the DNA domain.

In a preferred embodiment of the invention each version of the substantially homologous DNA domains present in the filamentous fungus comprises an integrated copy of the recombinant DNA molecule. Full occupation with integrated recombinant DNA molecules of all the DNA domain present in the fungus produces the highest possible copy number of the recombinant DNA molecule and provides a more stable situation because such a fungus contains no 'empty' DNA domains that could function as donor in gene conversions with filled DNA domains, thereby reducing the copy number of the integrated recombinant DNA molecule. Either each version of the same type of DNA domains may be occupied with recombinant DNA molecules or each version of different types of said DNA domains. Preferably, each version of all types of the substantially homologous DNA domains present in the genome of the filamentous fungus comprises an integrated copy of the recombinant DNA molecule.

In one advantageous aspect of the invention, the DNA domain used for integration of the recombinant DNA molecule is a domain which in its native state comprises an endogenous gene capable of high level expression. It is generally known that the expression level of an integrated recombinant gene can vary greatly depending on the genomic locus where that gene is integrated. The advantage of using highly expressed domains for integration of recombinant genes to be expressed is that these domains are at least capable of supporting high level expression of the endogenous gene. It is therefore likely that such domains will also support high level expression of an integrated recombinant gene. Indeed we have found that integration in the glaA domain of *A.niger* and integration in the penicillin cluster of *P.chrysogenum* as described in the examples herein provides higher expression levels per gene copy as compared to integration in some other genomic loci. In this context it will be understood that a gene capable of high level expression is defined as a gene which, when expressed at maximum level, produces an mRNA that constitutes at least 0.1% of the total mRNA population, preferably at least 0.5% of the total mRNA and most preferably at least 1% of the total mRNA. Examples of such highly expressible endogenous genes of which the domains in which they are contained are particularly suitable for the integration of the recombinant DNA molecule of the invention are genes encoding glycolytic enzymes, amylolytic enzymes, cellulolytic enzymes and/or antibiotic biosynthetic enzymes. Even more preferred are domains comprising genes involved in industrial processes and known to be expressed at high level such as glucoamylase genes, TAKA amylase genes, cellobiohydrolase genes and penicillin biosynthetic genes.

In a further aspect of the invention, the highly expressed endogenous gene is inactivated in each copy of the DNA domain in the filamentous fungus in cases where the expression of the endogenous gene is not required. In such cases the inactivation of the high level expression of the endogenous gene makes available energy and resources which can further the expression of the gene of interest. Moreover, in case both the desired enzyme to be produced by integration of the recombinant DNA molecule and the enzyme encoded by the endogenous gene are secreted enzymes, inactivation of the endogenous enzyme will result in more pure preparations of the desired enzyme. Preferably the endogenous gene is inactivated by means of an irreversible deletion of at least part of the endogenous gene in order to exclude reversion of the inactivation. More preferably the inactivation of the endogenous gene is effected by an irreversible deletion which comprises at least part of the promoter and upstream activating sequences. This is particularly advantageous in cases where the expression of a desired gene encoding an enzyme to be produced by integration of the recombinant DNA molecule is driven from a promoter derived from the endogenous gene because it will eliminate competition for potentially limiting transcription factors required for expression of the desired gene.

In a further embodiment of the invention, each version of the DNA domains is distinguished from the other versions of the domains in the filamentous fungus by means of an unique sequence tag. Such sequence tags allow to monitor the gene conversions between the different domains which facilitates the screening and/or selection of convertants with a desired genotype. Any form of sequence tags can be used as long as they allow detection of the different versions of the domain: e.g. ranging from restriction sites that are detected on Southern blots to complete selectable marker genes providing a easy assayable phenotype. A particularly useful embodiment of the sequence tag is exemplified herein and allows to detect each of the domains in a single PCR using one pair of oligonucleotides to prime the PCR. The domains are modified in such a way that in the PCR each version of the domains will produce a PCR fragment with a unique length. The length and intensity of the obtained PCR fragments are indicative for the presence and copy number of each of the domains, respectively. This form of sequence tag, referred to as "DNA flags", allows to rapidly analyze the genotype of large numbers of convertant colonies, in order to obtain a convertant with the desired genotype.

The present invention further relates to methods for preparing the filamentous fungi of the invention. These methods comprise the step of transforming a filamentous fungus comprising in one or more of its chromosomes at least two substantially homologous DNA domains suitable for integration of one or more copies of a recombinant DNA molecule and wherein the DNA domains are not the ribosomal DNA repeats, with a recombinant DNA molecule. Transformation of filamentous fungi is nowadays routine for the skilled person and a variety of transformation protocols suitable for filamentous fungi are available.

Transformation of the filamentous fungus with the recombinant DNA molecule requires the use of a selectable marker gene that allows to distinguish fungal cells that have taken up the transforming DNA form the untransformed cells. A variety of selectable marker genes are available for use in the transformation of filamentous fungi. Suitable markers include auxotrophic marker genes involved in amino acid or nucleotide metabolism, such as e.g. genes encoding ornithine-transcarbamylases (argB), orotidine-5'-decaboxylases (pyrG) or glutamine-amido-transferase indoleglycerol-phosphate-synthase phosphoribosyl-anthranilate isomerases (trpC), or involved in carbon or nitrogen metabolism, such e.g. niaD or facA, and antibiotic resistance markers such as genes providing resistance against phleomycin, bleomycin or neomycin (G418). Preferably, bidirectional selection markers are used for which both a positive and a negative genetic selection is possible. Examples of such bidirectional markers are the pyrG, facA and amdS genes. Due to their bidirectionality these markers can be deleted from transformed filamentous fungus while leaving the introduced recombinant DNA molecule in place, in order to obtain filamentous fungi that do not contain selectable markers. This essence of this MARKER GENE FREE™ transformation technology is disclosed in EP-A-0 635 574, which is herein incorporated by reference. Of these selectable markers the use of dominant and bidirectional selectable markers such as acetamidase genes like the amdS genes of *A. nidulans, A. niger* and *P. chrysogenum* is most preferred. In addition to their bidirectionality these markers provide the advantage that they are dominant selectable markers that, the use of which does not require mutant (auxotrophic) strains, but which can be used directly in wild type strains.

A further embodiment thus relates to filamentous fungi according to the invention wherein the recombinant DNA molecule lacks a selectable marker gene, or more preferably to filamentous fungi according to the invention which altogether lack a selectable marker gene.

The selectable markers used for transforming the filamentous fungi of the invention with the recombinant DNA molecule can either be physically linked to the recombinant DNA molecule to be transformed or they can be on a separate DNA molecule that is cotransformed with the desired recombinant DNA molecule. Cotransformation is routinely used by those skilled in the art because it occurs at relatively high frequency in filamentous fungi.

A next step in the methods for preparing the filamentous fungi of the invention comprises the selecting of a transformant with at least one recombinant DNA molecule integrated in at least one of the DNA domains of the filamentous fungus. A number of routine techniques are available to the skilled person for determining which of the obtained transformants has an integration of an recombinant DNA molecule in one of its DNA domains. In a further step the selected transformant is propagated and from its progeny a strain is selected in which at least two of the DNA domains comprise the integrated recombinant DNA molecule. This means that strains are selected in which the DNA domain comprising the integrated recombinant DNA molecule is multiplied, either through gene conversion with an "empty" DNA domain or through amplification. Such gene conversion and/or amplification events occur spontaneously at low frequency. The exact frequency at which these events occur may depend on a number of variables including the fungus in question and the number, the length and the extent of homology of the DNA domains. We have found, however, that these frequencies are sufficiently high to enable one to screen and select for strains in which these events have occurred using analysis techniques available today. Strains in which the DNA domain comprising the integrated recombinant DNA molecule is multiplied can e.g. be identified by simply screening for strains with higher production levels of the product whoses sythesis is effected by the recombinant DNA molecule, or alternatively such strains can be identified by analysing their genotype by e.g. the "DNA-flag" test as outlined above.

A method according to the invention may comprise additional steps in which one of the strains in which multiplication of the DNA domain comprising the integrated recombinant DNA molecule has occurred is propagated and wherein form its progeny strains are selected in which additional copies of the DNA domains comprise the integrated recombinant DNA molecule. These strains may then again be subjected to this procedure until a strain is obtained in which each of the DNA domains comprises the integrated recombinant DNA molecule. As outlined above herein, such strains provide that advantages that of high copy number of the recombinant DNA molecule and improved stability.

In a further aspect of the method for preparing the filamentous fungi of the invention, the recombinant DNA molecule comprises sequences which are substantially homologous to the DNA domains. The presence of such substantially homologous sequences in the recombinant DNA molecule will significantly increase the frequency at which the recombinant DNA molecule integrates into the DNA domain. The minimum requirement for the substantially homologous sequences in the recombinant DNA molecule is not known but in practice reasonable targeting frequencies are obtained with homologous targeting sequences of at least 1 kb, preferably at least 2 kb.

As mentioned above, one aspect of the invention relates to the use of bidirectional selectable markers for transforming the filamentous fungus with the recombinant DNA molecule. Once such a transformant has been obtained it is advantageous to subject them to counter selection for the absence of the bidirectional marker. Such markerless transformants can then be subjected to further transformations or can be propagated to select from its progeny strains with gene conversions and/or amplifications of the DNA domain comprising the recombinant DNA molecule(s).

In an alternative method for preparing a filamentous fungus according to the invention a filamentous fungus is transformed with a recombinant DNA molecule and a transformant is selected with at least one recombinant DNA molecule integrated in a predetermined genomic target sequence. This transformant is subsequently propagated and from its progeny strains are selecting with at least two DNA domains comprising the integrated recombinant DNA molecule. In this case the recipient filamentous fungus to be transformed with the recombinant DNA molecule does not necessarily contain multiple copies of the DNA domain. The DNA domain is rather amplified after that the recombinant DNA molecule is integrated therein.

The present invention allows the preparation of recombinant filamentous fungi comprising in one or more of its chromosomes at least two substantially homologous DNA domains suitable for integration of one or more copies of a recombinant DNA molecule, wherein the DNA domains are not the ribosomal DNA repeats, and wherein at least two of the DNA domains comprise an integrated copy of a recombinant DNA molecule. These recombinant fungi can be used in processes for the production of a product of interest. Such a process will usually include the steps of culturing the recombinant cells in a medium conducive to the production of the product of interest and recovery of the product of interest from the culture medium and/or from the fungus. The products of interest can be proteins, such as an enzyme, and/or primary metabolites, such as $CO_2$, alcohol or organic acids, and/or secondary metabolites, such as antibiotics or carotenoids. The product of interest can also be the recombinant fungi themselves, i.e. the biomass obtained in the process. Examples of enzymes and proteins that can be produced in the filamentous fungi of the invention include lipases, phospholipases, phosphatases, phytases, proteases, pullulanases, esterases, glycosidases, amylases, glucoamylases, catalases, glucose oxidases, β-glucosidases, arabinofuranosidases, rhamnosidases, apiosidases, chymosin, lactoferrin, cell wall degrading enzymes such as cellulases, hemicellulases, xylanases, mannanases, pectinases, rhamnogalacturonases, and the like.

Some of the advantages of the filamentous fungi of the invention and the methods for their preparation are summarized below:

The present invention provides greater versatility as compared to the available systems for non-random multicopy integration recombinant DNA molecules in filamentous fungi. Greater versatility because the present invention is not confined to the use of deficient selectable marker genes for transformation, and also because the present invention is not confined to the use of only ribosomal DNA sequences as target sequence for integration.

The filamentous fungi of the invention provide greater genetic stability of the integrated multiple copies of the recombinant DNA molecule as compared to conventional recombinant filamentous fungi in which the recombinant DNA molecules are randomly integrated in tandem arrays.

In particular, filamentous fungi with a high copy number of randomly integrated recombinant DNA molecules will usually have a large numbers of tandemly repeated recombinant DNA molecules integrated in only few genomic loci. This configuration is inherently less stable than a configuration according to the invention, wherein only few tandemly repeated copies of the recombinant DNA molecule (preferably not more than five copies) are integrated in several different genomic sites such as the substantially homologous DNA domains. For example, a filamentous fungus according to the invention may have a copy number of 15, whereby the fungus may have three tandemly repeated copies of a recombinant DNA molecule integrated in each of five substantially homologous DNA domains. In contrast, a conventional recombinant filamentous fungus with a copy number of 15 may have 10 copies integrated in one undefined genomic site and 5 copies in another undefined genomic site. In accordance with the prsent invention it has been found the latter configuration to be less stable with respect to the loss of the recombinant DNA molecules as compared to a fungus according to the invention having the same copy number.

The filamentous fungi of the invention are expected to provide higher expression levels per gene copy as compared filamentous fungi with integrations in ribosomal DNA because the latter has not evolved to support high level RNA-polymerase II transcription of protein encoding genes.

The filamentous fungi of the invention are multicopy strains of which the genotype can be completely defined at least as far as the integrated recombinant DNA molecules are concerned. This will facilitate obtaining regulatory approval for processes and products in which these fungi are involved.

For similar reasons the phenotype of the filamentous fungi will be much more predictable as compared to conventional recombinant filamentous fungi in which the recombinant DNA molecules are randomly integrated because the random integration can alter the expression of unknown genes that are resident in or near the integration sites.

The methods for preparation of the filamentous fungi of the invention provide the advantage of synergy with earlier classical strain improvement programs. As outlined above, in preferred embodiment of the invention industrial filamentous fungi are used which have been obtained in classical strain improvement programs. The use of such fungi is not only advantageous because they will often comprise amplicons that are suitable for the integration and subsequent multiplication of recombinant DNA molecules according to the invention, but also because the industrial filamentous fungi will have accumulated (a large number of) mutations that are advantageous not only for the productions of the product at which the strain improvement program was aimed (the "previous" product) but also for other new products. By modifying in these improved industrial filamentous fungi the genes involved in the production of the "previous" product so as to enable the fungus to produce a new product, the advantageous mutations will now contribute to the efficient production of the new product. In this way the present invention can safe significant efforts in the development of new production strains.

The present invention allows the "designing and building" of recombinant filamentous fungi. With the expression "designing and building" we mean that at single copy level a design is made of all the desired genetic modifications to be introduced in a DNA domain. E.g. in case of the production of a desired protein one or more expression cassettes for the protein are integrated in the DNA domain and in the same domain resident endogenous genes that might negatively influence the expression of the desired protein are inactivated. In case a mixture of proteins is to be produce the designing will comprise adjusting the expression levels of the different proteins to the desired ratios. The latter may be particularly advantageous in the case of metabolic pathway engineering where a number of new metabolic activities, forming part of a new metabolic pathway, are to be introduced in a predetermined ratio. Once these design of these desired genetic modification has been established in the DNA domain at single copy level, the building process can begin, which means that the designed single copy domain is multiplied by gene conversion and/or amplification of the domain comprising the desired genetic modifications until the desired production level is reached.

EXAMPLES

| Nomenclature | |
|---|---|
| A. niger | Aspergillus niger |
| P. chrysogenum | Penicillium chrysogenum |
| S. clavuligerus | Streptomyces clavuligerus |
| A. nidulans | Aspergillus nidulans |
| phyA | A. niger phyA gene, encoding phytase. |
| amdS | A. nidulans amdS gene, encoding acetamidase (Corrick et al., 1987 Gene 53:63–71) |
| cefE | S. clavuligerus cefE gene, encoding deacetoxy-cephalosporin C synthetase. (Kovacevic et al., 1989 J. Bacteriol. 171:754–760) |
| cefF | S. clavuligerus cefF gene, encoding deacetyl-cephalosporin C synthetase. (Kovacevic, S. and Miller, J. R. 1991 J. Bacteriol. 173:398–400) |

| Nomenclature | |
|---|---|
| niaD | *P. chrysogenum* niaD gene encoding nitrate reductase (Haas et al., 1996 Biochem. Biophys. Acta 1309:81–84) |
| glaA | *A. niger* glaA gene encoding glucoamylase |
| gpdA | *A. nidulans* gpdA gene, encoding glyceraldehyde 3-phosphate dehydrogenase (Punt et al., 1988 Gene 69:49–57) |
| pcbC | *P. chrysogenum* pcbC gene, encoding isopenicillin N synthase (IPNS) (Carr et al., 1986 Gene 48:257–266) |
| $P_{gpdA}$ | gpdA promoter |
| $P_{glaA}$ | glaA promoter |
| $P_{pcbC}$ | pcbC promoter |
| $T_{penDE}$ | penDE terminater |
| $T_{amdS}$ | amdS terminater |
| $T_{glaA}$ | glaA terminater |
| GLA | *A. niger* glucoamylase protein |

| Abbreviations | |
|---|---|
| CHEF | Clamped Homogenous Electric Fields (electrophoresis) |
| TAFE | Transverse Alternating Field Electrophoresis |
| kb | kilo base |
| bp | base pair |
| ADCA | aminodeacetoxycephalosporanic acid |
| ADAC | aminodeacetylcephalosporanic acid |
| oligo | oligonucleotide |
| PCR | Polymerase Chain Reaction |

Oligo nucleotides:

1. 5'-gta gct gcg gcc gcc tcc gtc ttc act tct tcg ccc gca ct-3'  [SEQ. ID NO.1]

2. 5'-caa agg gca tgc ggc cgt atc ggc cgg tga caa aca tca ttc aac gcc-3'  [SEQ. ID NO.2]

3. 5'-atg ttt aag ctt ggc cga tac ggc caa aac acc ttt gat tcc-3'  [SEQ. ID NO.3]

4. 5'-caa gtt gcg gcc gct cct cac taa cga gcc agc aga tat cga tgg-3'  [SEQ. ID NO.4]

5. 5'-ctt atg cgg ccg cga att cga gct ctg tac agt gac-3'  [SEQ. ID No.5]

6. 5'-cgg tac gtg cgg ccg ctc gta cca tgg gtt gag tgg tat g-3'  [SEQ. ID NO.6]

7. 5'-ata tgt gcg gcc gct tta cat ggt caa tgc aat tag atg gtg g-3'  [SEQ. ID NO.7]

8. 5'-ata act cta gag gcc cta ccg gcc ttt gca aat ata ctg taa gaa cc-3'  [SEQ. ID NO.8]

9. 5'-gta tat tct gca ggg ccg gta ggg cca aca gtt tcc gca ggt g-3'  [SEQ. ID NO.9]

10. 5'-gta tgg gcg gcc gct tta caa cta gaa tat ggg aac ctg tgg g-3'  [SEQ. ID NO.10]

11. 5'-ctc gag tgc ggc cgc aaa gct agc ttg ata tcg aat tcc tta tac tgg gcc tgc tgc att g-3'  [SEQ. ID NO.11]

12. 5'-gtc cat atg ggt gtc tag aaa aat aat ggt gaa aac ttg aag gcg-3'  [SEQ. ID NO.12]

13. 5'-cat atg gcg gac acg ccc gta ccg atc ttc-3'  [SEQ. ID NO.13]

14. 5'-atg cat tgg ctc gtc atg aag agc tat ca tcc ggc ctg cgg ctc gtt ctt cgc-3'  [SEQ. ID NO.14]

15. 5'-cag cta ccc cgc ttg agc aga cat c-3'  [SEQ. ID NO.15]

16. 5'-gtc agg gaa gaa cac gag ggc gca g-3'  [SEQ. ID NO.16]

17. 5'-ccc tct ctt cgt cgt tgt cca cgc c-3'  [SEQ. ID NO.17]

18. 5'-atg tcc ttg gcc gac ttc agc tcg g-3'  [SEQ. ID NO.18]

19. 5'-gac gag cca atg cat ctt ttg tat g-3'  [SEQ. ID NO.19]

-continued

```
20. 5'-cgg gta ctc gct cta cct act tcg g-3'        [SEQ. ID NO.20]

21. 5'-gcc cag tat aag gaa ttc gat atc aag-3'      [SEQ. ID NO.21]

22. 5'-agg gtc gac act agt tct aga gcg g-3'        [SEQ. ID NO.22]

23. 5'-gac gtt atc gga cgg aga ctc agt g-3'        [SEQ. ID NO.23]

24. 5'-gcc tac tct gtt ctg gag agc tgc-4'          [SEQ. ID NO.24]

25. 5'-ccc cca tcc cgg tca cgc act cgc g-3'        [SEQ. ID NO.25]

26. 5'-cac aga gaa tgt gcc gtt tct ttg g-3'        [SEQ. ID NO.26]

27. 5'-tca cat atc ccc tac tcc cga gcc g-3'        [SEQ. ID NO.27]

28. 5'-gtc gcg tat ccc agg-3'                      [SEQ. ID NO.28]

29. 5'-gtc aaa gga tat gca tac-3'                  [SEQ. ID NO.29]

30. 5'-agc tta tgc ggc cgc gaa ttc agg tac cgt atc tcg aga-  [SEQ. ID NO.30]
    3'

31. 5'-att ttc tcg aga tac ggt acc tga att cgc ggc cgc ata-  [SEQ. ID NO.31]
    3'

32. 5'-gtg cga ggt acc aca atc aat cca ttt cgc-3'  [SEQ. ID NO.32]

33. 5'-atg gtt caa gaa ctc ggt agc ctt ttc ctt gat tct-3'    [SEQ. ID NO.33]

34. 5'-aga atc aag gaa aag gct acc gag ttc ttg aac cat-3'    [SEQ. ID NO.34]

35. 5'-atc aat cag aag ctt tct ctc gag acg ggc atc gga gtc   [SEQ. ID NO.35]
    ccg-3'

36. 5'-gac cat gat tac gcc aag ctt-3'              [SEQ. ID NO.36]

37. 5'-gga tcc tta act agt taa gtg ggg gcc tgc gca aag-3'    [SEQ. ID NO.37]

38. 5'-tta act agt taa gga tcc aca atc aat cca ttt cgc-3'    [SEQ. ID NO.38]

39. 5'-gct cta gag cgg ccg cga att cat ccg gag atc c-3'      [SEQ. ID NO.39]

40. 5'-ctt tgc gca ggc ccc cac-3'                  [SEQ. ID NO.40]

41. 5'-tgc agg gta aat cag gga-3'                  [SEQ. ID NO.41]

42. 5'-tcc gct aaa ggt ggt cgc g-3'                [SEQ. ID NO.42]

43. 5'-ccc cag cat cat tac acc tc-3'               [SEQ. ID NO.43]

44. 5'-aaa gga ccc gag atc cgt ac-3'               [SEQ. ID NO.44]

45. 5'-tct cga tac caa ggt cac cac ggg c-3'        [SEQ. ID NO.45]

46. 5'-gca tcc atc ggc cac cgt cat tgg a-3'        [SEQ. ID NO.46]

47. 5'-atc cag acc agc aca ggc agc ttc g-3'        [SEQ. ID NO.47]

48. 5'-tcc gca tgc cag aaa gag tca ccg g-3'        [SEQ. ID NO.48]

49. 5'-gtc gac tta act agt taa ggc ttc aga cgc agc gag-3'    [SEQ. ID NO.49]

50. 5'-tta act agt taa gtc gac aca atc aat cca ttt cgc-3'    [SEQ. ID NO.50]

51. 5'-aga tct tta act agt taa gtg gcc tga aca gtg ccg-3'    [SEQ. ID NO.51]

52. 5'-tta act agt taa aga tct aca atc aat cca ttt cgc-3'    [SEQ. ID NO.52]
```

Materials & Methods

General Procedures

Standard molecular cloning techniques such as DNA isolation, gel electrophoresis, enzymatic restriction modifications of nucleic acids, Southern analyses, E. coli transformation e.a., were performed as described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego. Synthetic oligo deoxynucleotides were obtained from ISOGEN Bioscience (Maarssen, The Netherlands). DNA sequence analyses were performed on an Applied Biosystems 373A DNA sequencer, according to supplier's instructions.

Transformation of Aspergillus niger.

Transformation of A. niger was performed according to the method described by Tilburn, J. et.al. (1983) Gene 26, 205–221 and Kelly, J. & Hynes, M. (1985) EMBO J., 4, 475–479 with the following modifications:

Spores were grown for 16 hours at 30° C. in a rotary shaker at 300 rpm in Aspergillus minimal medium. Aspergillus minimal medium contains per liter: 6 g $NaNO_3$; 0.52 g KCl; 1.52 g $KH_2PO_4$; 1.12 ml 4 M KOH; 0.52 g $MgSO_4.7H_2O$; 10 g glucose; 1 g casaminoacids; 22 mg $ZnSO_4.7H_2O$; 11 mg $H_3BO_3$; 5 mg $FeSO_4.7H_2O$; 1.7 mg $CoCl_2.6H_2O$; 1.6 mg $CuSO_4.5H_2O$; 5 mg $MnCl_2.2H_2O$; 1.5 mg $Na_2MoO_4.2H_2O$; 50 mg EDTA; 2 mg riboflavin; 2 mg thiamine-HCl; 2 mg nicotinamide; 1 mg pyridoxine-HCL; 0.2 mg panthotenic acid; 4 µg biotin; 10 ml Penicillin (5000 IU/ml) Streptomycin (5000 UG/ml) solution (Gibco).

Novozym 234 (Novo Industries) instead of helicase was used for preparations of protoplasts;

after protoplast formation (60–90 minutes), KC buffer (0.8 M KCl, 9.5 mM citric acid, pH6.2) was added to a final volume of 45 ml, the protoplast suspension was centrifuged for 10 minutes at 3000 rpm at 4° C. in a swinging-bucket rotor. The protoplasts were resuspended in 20 ml KC buffer and subsequently 25 ml of STC buffer (1.2 M sorbitol, 10 mM Tris-HCl pH 7.5, 50 mM $CaCl_2$) was added. The protoplast suspension was centrifuged for 10 minutes at 3000 rpm at 4° C. in a swinging-bucket rotor, washed in STC-buffer and resuspended in STC-buffer at a concentration of $10^8$ protoplasts/ml;

to 200 µl of the protoplast suspension the DNA fragment, dissolved in 10 µl in TE buffer (10 mM Tris-HCl pH 7.5, 0.1 mM EDTA), 100 µl of a PEG solution (20% PEG 4000 (Merck), 0.8 M sorbitol, 10 mM Tris-HCl pH 7.5, 50 mM $CaCl_2$) was added;

after incubation of the DNA-protoplast suspension for 10 minutes at room temperature, 1.5 ml PEG solution (60% PEG 4000 (Merck), 10 mM Tris-HCl pH 7.5, 50 mM $CaCl_2$) was added slowly, with repeated mixing of the tubes. After incubation for 20 minutes at room temperature, suspensions were diluted with 5 ml 1.2 M sorbitol, mixed by inversion and centrifuged for 10 minutes at 4000 rpm at room temperature. The protoplasts were resuspended gently in 1 ml 1.2 M sorbitol and plated onto selective regeneration medium consisting of Aspergillus minimal medium without riboflavin, thiamine.HCL, nicotinamide, pyridoxine, panthotenic acid, biotin, casaminoacids and glucose, supplemented with 10 mM acetamide as the sole nitrogen source, 1 M sucrose, solidified with 2% bacteriological agar #1 (Oxoid, England). After incubation for 6–10 days at 30° C., the plates were replica plated onto selective acetamide plates consisting of Aspergillus minimal medium with 2% glucose instead of sucrose and 1.5% agarose instead of agar. Single transformants were isolated after 5–10 days of growth at 30° C.

Transformation of *Penicillium chrysogenum*.

The Ca-PEG mediated protoplast transformation procedure is used. Preparation of protoplasts and transformation of *P. chrysogenum* was performed according to the method described by Gouka et al., Journal of Biotechnology 20 (1991), 189–200 with the following modifications:

After transformation, the protoplasts were plated onto selective regeneration medium plates consisting of Aspergillus minimal medium, osmotically stabilized with 1.2 M sucrose, containing 0.1% acetamide as sole nitrogen source and solidified with 1.5% bacteriological agar #1 (Oxoid, England).

After 5–8 days of incubation at 25° C. transformants appeared.

TAFE

DNA fragments ranging from 20 to 50 kb were separated on 1% agarose gels by TAFE, using a Beckman Geneline™ II apparatus (Beckman) according to instructions of the suppliers. Electrophoresis parameters: 4 sec A, 4 sec B pulsetimes at 300 mA for approximately 18 h at 14° C.

CHEF

DNA fragments larger than approximately 50 kb were separated on 1% agarose gels by CHEF electrophoresis, using a CHEF-DRII module (BioRad), equiped with a Pulsewave 760 Switcher, Model 200/2.0 power supply, and CHEF electrophoresis cell. Electrophoresis parameters: initial time 50 sec, final time 90 sec, start ratio 1.0, 200 V for 20 to 24 h at 14° C.

Quantitation of PCR Products and Hybridization Signals

PCR products and hybridization signals were quantitated from photographs of ethidium bromide stained agarose gels or autoradiograms, respectively, according to the ImageQuaNT™ software (Molecular Dynamics).

DNA Labeling and Hybridizations

DNA labeling and hybridizations were according to the ECL™ direct nucleic acid labeling and detection systems. (Amersham LIFE SCIENCE, Little Chalfont, England).

Cassette- and DNA-flag Specific PCR Procedure on *A. niger* Colonies.

*A. niger* spores were plated onto PDA-plates (Potato Dextrose Agar, Oxoid; prepared according to the supplier's instructions). After growth for 48 hours at 30° C., the ½–¼ part mycelium of a single colony was transferred to 50 µl novozym (5 mg Novozym 234 (Novo Industries) per ml KC (0.8 M KCl, 9.5 mM citric acid, pH 6.2)) and incubated for 1 hour at 37° C. Subsequently, 300 µl DNA dilution buffer (10 mM Tris-HCl pH 7.5; 10 mM NaCl; 1 mM EDTA) was added and the suspension was boiled for 5 minutes at 100° C., followed by vigorously fortexing to rupture intact mycelium. 5 µl of these mixtures was used as template in 50 µl PCR reactions containing 5 µl 10×Super Taq PCR buffer 1 (HT Biotechnology Ltd.), 8 µl dNTP's (1.25 mM each), 20–80 ng of each oligo nucleotides and 1U Super Taq (HT Biotechnology Ltd, Cambridge, UK). The optimal amount of oligo's was determined experimentally for each purchased batch.

Twenty-five amplification cycles, (each: 1 min 94° C., 1 min 55° C. and 1.5 min 72° C.) and a final extension step of 7 min 72° C., were performed in a DNA-amplifier (e.g. Perkin-Elmer, Hybaid).

For the DNA flag-test, as primer set oligo's 40/41 was used, for the phyA cassette PCR test oligo set 42/43 and for the amdS cassette test the oligo set 15/16. Subsequently, to analyse PCR products, 20 µl of the PCR mixture was analyzed by agarose gel electrophoresis on a 2% agarose gel in TBE buffer (0.09M Tris, 0.09 M $H_3BO_3$, 2 mM EDTA; pH 8.3).

Targeting Specific PCR Procedure for *Aspergillus niger*.

Preparation of DNA-templates and PCR reaction conditions were used as described for the targeting PCR test for Penicillium. As primer sets, oligo's 46/48 were used to the determine whether the amdS cassette is targeted adjacent to the glaA target locus, and oligo set 46/47 to determine whether the phyA cassette is targeted adjacent to the glaA target locus. Used PCR conditions were as described for the targeting PCR test for Penicillium.

Targeting PCR of *P. chrysogenum* Transformants

Approximately one third of 4-days old colonies was incubated for 2 h at 37° C. in 50 µl KC buffer (60 g/l KCl, 2 g/l citric acid, pH 6.2), supplemented whith 5 mg/ml Novozym™234. Subsequently 100 µl 10 mM Tris, 50 mM EDTA, 150 mM NaCl, 1% SDS, pH8 and 400 μl QIAquick™ PB buffer (Quiagen Inc., Chatsworth, USA) was added. Extracts were gently resuspended and loaded onto a QIAquick™ spin column. Columns were centrifugated for 1 min at 13000 rpm in a microfuge and washed once with 500 μl QIAquick™ PE buffer. Traces of ethanol were removed by a final quick spin. Chromosomal DNA (PCR template) was eluted from the column by addition of 50 μl H$_2$O and subsequent centrifugation for 1 min at 13000 rpm. PCR reactions contained 10pl eLONGase™ B buffer (Life Technologies, Breda, The Netherlands), 14 μl dNTP's (1.25 mM each), 1 μl eLONGase™ Enzyme Mix, 1 μl template, and 30–50 ng of each oligo, in a final volume of 50 μl. The optimal amount of oligo's was determined experimentally for each purchased batch. On average, 30 to 50 ng was used. Reactions were performed with the following cycle conditions: 1×(2 min 94° C.), 10×(15 sec 94° C., 30 sec 55° C., 4 min 68° C.), 20× (15 sec 94° C., 30 sec 55° C., 4 min start with incline of 20 sec per cycle, 68° C.), 1× (10 min 68° C.). Samples of 8 μl were loaded on agarose gels for analyses of PCR products.

Cassette PCR of *P. chrysogenum* Transformants

Approximately one third of 4-days old colonies was incubated for 2 h at 37° C. in 200 μl DVB buffer (10 mM Tris, 10 mM NaCl, 1 mM EDTA, pH7.5), supplemented with 5 mg/ml Novozym™234. The mixture was boiled for 8 min and subsequently vortexed vigorously to disrupt intact mycelia. Five μl of these mixtures was used as template in 50 μl PCR reactions containing 5 μl 10× Super Taq PCR buffer (HT Biotechnology Ltd., Cambridge, UK), 8 μl dNTP's (1.25 mM each), 1 U Super Taq and 20–80 ng of each oligo. The optimal amount of oligo's was determined experimentally for each purchased batch. On average, 20 to 80 ng was used. Reactions were performed with the following cycle conditions: 25×(1 min 94° C., 1 min 55° C., 1,5 min 72° C.), 1×(8 min 72° C.). Samples of 15 μl were loaded on agarose gels for analyses of PCR products.

Chromosomal DNA Isolation.

*A. niger* and *P. chrysogenum* spores were inoculated in 20 ml Aspergillus minimal medium (see transformation of *A. niger*) in a 100 ml conical flask and grown for 20–24 hours at 30° C. in a rotary shaker at 300 rpm. 5–10 ml of a well grown culture were inoculated in 100 ml fresh Aspergillus minimal medium and grown for another 20–24 hours at 30° C. in a rotary shaker at 300 rpm. After growth, mycelium was harvested by filtration over a Miracloth (Cal Biochem) filter and washed with 15 ml KC buffer (0.8 M KCl, 9.5 mM citric acid, pH 6.2). Per gram of the washed mycelium (3–5 g. of a 100 ml culture) 4 ml KC buffer and 0.25 ml novozym (50 mg Novozym 234 (Novo Industries) /ml KC buffer) was added and protoplast formation was allowed to take place at 30° C. under gently shaking. After protoplast formation, KC buffer was added to a volume of 45 ml and the protoplast suspension was centrifuged at 3000 rpm at 4° C. for 5 minutes in a swinging bucket rotor. Protoplasts were resuspended in 20 ml KC buffer. Then 25 ml of STC buffer (1.2 M sorbitol, 10 mM Tris-HCl pH 7.5, 50 mM CaCl$_2$) was added and after mixing the suspension was subsequently centrifuged at 3000 rpm at 4° C. for 5 minutes in a swinging bucket rotor, resuspended in 50 ml STC buffer and again centrifuged for 5 minutes at 2500×g at 4° C. in a swinging bucket rotor. To 0.3–0.6 ml of the protoplast pellet 60 μl proteinase-K (20 mg/ml) and 1 ml low melting point agarose (0.8% in 1 M Sorbitol/0.45 M EDTA) was added. After mixing by vortexing, the suspension was transferred to wells of a preformed plexiglass mold and set on ice for approx. 15 minutes. Next, the agarose plugs were transferred to 2.5 ml sarcosyl solution (1% Na-lauroyl sarcosine in 0.5 M EDTA). 60 μl Proteinase-K (20 mg/ml) was added and after incubation for 16–20 hours at 50° C. the sarcosyl solution was replaced by 10 ml 50 mM EDTA solution. After 2 hours incubation at 50° C., the EDTA solution was replaced by 10 ml fresh 50 mM EDTA and incubated for another 2 hours at 50° C. Finally, the EDTA solution was replaced by 10 ml fresh 50 mM EDTA solution and the agarose plugs were stored at 4° C.

Restriction Enzyme Digestions of Chromosomal DNA Agarose Plugs.

Part of a DNA agarose plug (prepared as described above), containing 1–3 μg chromosomal DNA, was incubated in 1 ml TE (10 mM Tris-HCl pH 7.5, 1 mM EDTA) for 1 hour at 37° C. The 1 ml TE-buffer was refreshed and the incubation continued for another hour at 37° C. Then the TE-buffer was replaced by 200 μl of a buffer appropriate for each restriction enzyme as recommended by the supplier. After an incubation at 37° C. for one hour, the restriction enzyme buffer was refreshed (50 μl) and incubated for 10 minutes at 65° C. to dissolve the agarose. Finally, 20–40 Units of the appropriate restriction enzyme was added and the digestion mixture was incubated for 16 hours at a temperature as recommended by the supplier for each restriction enzyme.

AmdS counter Selection Procedure.

In most derived vectors the amdS selection marker gene is positioned between DNA repeats. Therefor, in realized transformants with these vectors, removal of the amdS marker gene can be achieved either by internal recombination over the flanking DNA repeats within the cassette or by homologous recombination over repeats that are created by integration via a single cross-over event. Selection of cells that have lost the amdS selection marker is achieved by growth on plates containing fluoroacetamide. Cells harboring the amdS gene metabolize fluoroacetamide to ammonium and fluoroacetate which is toxic to the cell. Consequently, only cells that have lost the amdS gene are able to grow on plates containing fluoroacetamide.

In case of removal of the amdS marker from Aspergillus transformants, spores from these transformants were plated onto selective regeneration medium (described above) containing 5 mM fluoroacetamide and 5 mM ureum instead of 10 mM acetamide, 1.1% glucose instead of 1M sucrose and 1.1% instead of 2% bacteriological agar #1 (Oxoid, England). After 7–10 days of growth at 30° C. single colonies were harvested and plated onto 0.4% potato dextrose agar (Oxoid, England).

In case of removal of the amdS marker from Penicillium transformants, spores from these transformants were plated onto Aspergillus minimal medium containing 10 mM fluoroacetamide and 5% glucose, solidified with 1.5% bacteriological agar #1 (Oxoid, England). After 5–10 days of growth at 25° C., resistant colonies appeared.

*E. coli* Bioassay

Transformants were grown on YPD agar medium for 5 days. *E. coli* ESS2231 was used as indicator bacterium in an agar overlay, that also contained Bacto penase to be able to discriminate between penicillin and cephalosporin production, according to methods well known in the art (Guttiérez et al., Mol. Gen. Genet. 1991 225:56–64). Transformants expressing cefE were identified by a clarification of the agar overlay around the colony.

Industrial Strain Improvement of *P. chrysogenum*

Standard mutagenic techniques and screening procedures well known to persons skilled in the art (Rowlands, 1984 Enzyme Microb. Technol. 6:3–10) were used to isolate *P.*

*chrysogenum* strain CBS 649.97 (deposited on Apr. 11, 1997 at the Centraal Bureau voor Schimmelcultures, Oosterstaat 1, P.O. Box 273,3740 AG, Baarn, The Netherlands) from Wis54-1255 (ATCC 28089)

Adipoyl-7-ADCA and adipoyl-7-ADAC fermentations

Fermentative productions and quantitation of adipoyl-7-ADCA and adipoyl-7-ADAC were essentially as described for production of 2-(carboxyethylthio) acetyl- and 3-(carboxymethylthio) propionyl-7-ADCA (WO 95/04148) with the exception that 3 g/l adipic acid was added to the culture medium instead of 3'-carboxymethylthiopropionic acid. Synthetic adipoyl-7-ADCA and adipoyl-7-ADAC were used as reference substrates.

Aspergillus niger Shake Flask Fermentations.

Of recombinant and control *A. niger* strains a large batch of spores were generated by plating spores or mycelia onto PDA-plates (Potato Dextrose Agar, Oxoid), prepared according to the supplier's instructions. After growth for 3–7 days at 30° C. spores were collected after adding 0,01% Triton X-100 to the plates. After washing with sterile water about 10⁷ spores of selected transformants and control strains were inoculated into shake flasks, containing 20 ml of liquid preculture medium containing per liter: 30 g maltose.$H_2O$; 5 g yeast extract; 10 g hydrolyzed casein; 1 g $KH_2PO_4$; 0.5 g $MgSO_4$.$7H_2O$; 0.03 g $ZnCl_2$; 0.02 g $CaCl_2$; 0.01 g $MnSO_4$.$4H_2O$; 0.3 g $FeSO_4$.$7H_2O$; 3 g Tween 80; 10 ml penicillin (5000 IU/ml)/Streptomycin (5000 UG/ml); pH 5.5. These cultures were grown at 34° C. for 20–24 hours. 10 ml of this culture was inoculated into 100 ml of *A. niger* fermentation medium containing per liter: 70 g maltodextrines; 25 g hydrolyzed casein; 12.5 g yeast extract; 1 g $KH_2PO_4$; 2 g $K_2SO_4$; 0.5 g $MgSO_4$.$7H_2O$; 0.03 g $ZnCl_2$; 0.02 g $CaCl_2$; 0.01 g $MnSO_4$.$4H_2O$; 0.3 g $FeSO_4$.$7H_2O$; 10 ml penicillin (5000 IU/ml)/Streptomycin (5000 UG/ml); adjusted to pH 5.6 with 4 N $H_2SO_4$. These cultures were grown at 34° C. for 6 days. Samples taken from the fermentation broth were centrifuged (10', 5.000 rpm in a swinging bucket centrifuge) and supernatants collected. Glucoamylase or phytase activity assays (see below) were performed on these supernatants.

Glucoamylase Activity Assay.

The glucoamylase activity was determined by incubating 10 μl of a six times diluted sample of the culture supernatant in 0.032 M NaAC/HAC pH 4.05 with 115 μl of 0.2% (w/v) p-Nitrophenyl α-D-glucopyranoside (Sigma) in 0.032 M NaAc/HAc pH 4.05. After a 30 min incubation at room temperature, 50 μl of 0.3 M $Na_2CO_3$ was added and the absorbance at a wavelength of 405 nm was measured. The $A_{405nm}$ is a measure for the GLA production.

Phytase Activity Assay.

100 μl supernatant (diluted when necessary) of shake flask- or micro-titer *Aspergillus niger* fermentations (as reference 100 μl demiwater) is added to 900 μl mixture, containing 0.25 M sodium acetate buffer pH 5.5, 1 mM phytic acid (sodium salt, Sigma P-3168) and incubated for 30 minutes at 37° C. The reaction is stopped by the addition of 1 ml 10% TCA (trichloroacetic acid). After the reaction has been terminated, 2 ml of reagent (3.66 g $FeSO_4$.$7H_2O$ in 50 ml of ammonium molybdate solution (2.5 g $(NH_4)_6Mo_7O_{24}$.$4H_2O$ and 8 ml $H_2SO_4$ diluted up to 250 ml with demiwater) is added.

The absorbance of the blue color is measured spectrophotometrically at 690 nm. The measurements are indicative of the quantity of phosphate released in relation to a calibration curve of phosphate in the range of 0–1 mMol/l.

Culturing of Microorganisms

*S. clavuligerus* strain ATCC 27064 was cultured at 27° C. in tryptic soy broth (Difco).

*P. chrysogenum* strains were cultured at 25° C. in complete YPD medium (1% yeast extract, 2% peptone, 2% glucose). For solid media, 2% Bacto-agar was added. Transformants were purified by repeated cultivation on YPD agar. Single stable colonies were used to prepare agar slants for production of spores.

*A. niger* strains were cultured at 30° C. on PDA containing plates. Transformants were purified by repeated cultivation on PDA plates. Single stable colonies were used to prepare again slants for production of spores.

*E. coli* strains were cultured according to standard procedures (Sambrook)

EXAMPLES A. NIGER

1.1 Selection and Characterization of *Aspergillus niger* Hosts 1.1.a Rationale.

The presence of repeated DNA domains in the genome is essential to use gene conversion as tool to amplify inserted recombinant expression cassettes. For example, the glaA gene of high glucoamylase producing *A. niger* strains could be present on such amplified DNA domains. In order to identify suitable hosts for the production of industrial enzymes we screened for *A. niger* strains with improved glucoamylase production. Here we describe the procedure how to select and to characterize such *A. niger* strains containing the required DNA amplicons.

1.1.b Selection of *A. niger* mutants. From the *A. niger* CBS 513.88 (deposited Oct. 10, 1988) several mutant strains were selected showing an improved production of glucoamylase on shake flask level. Mutagenesis was performed on spores of *A. niger* CBS 513.88 by UV-treatment. Surviving spores (approximately 1%) were tested for their ability to produce glucoamylase in shake flask fermentations as described in Material & Methods. After 6 days of growth glucoamylase enzyme activities were determined as described in Material & Methods.

Several *A. niger* mutant strains could be selected showing enhanced glucoamylase production levels even up to 600 U glucoamylase/ml. The parent strain *A. niger* CBS 513.88 reaches a level of approximately 200 glucoamylase U/ml. The best producing *A. niger* mutant strain was deposited as *A. niger* CBS 646.97 on April 11, 1997 at the Centraal Bureau voor Schimmelcultures, Oosterstaatt, P.O. Box 273, 3740 AG, Baarn, The Netherlands.

1.1.c Genetic Characterization of *A. niger* CBS 646.97.

To determine whether the above described increased in glucoamylase production is the consequence of an amplification of the glaA locus, chromosomal DNA was isolated from the mutant strain *A. niger* CBS 646.97 and its parent *A. niger* CBS 513.88. Southern analyses were carried out on isolated DNA, digested with EcoRI and SalI and probed with a glucoamylase/phytase DNA fragment (glaA/phyA fusion: an EcoRI/BamHI fragment from pFYT3, which is described in Patent Application EP 0420358A1)). Autoradiographs clearly show that improved glucoamylase mutant strain contains multiple (3–4) glaA gene copies.

1.1.d. Size of glaA Amplicons in the Mutant *A. Niger* Strain.

TAFE analyses revealed that large DNA fragments are amplified in the selected mutant *A. niger* strain. Chromosomal DNA was derived from the original *A. niger* CBS 513.88 strain as well as from the *A. niger* CBS 646.97 strain as described in Materials & Methods. Digestions with HindIII and the eight-cutter restriction enzymes NotI, SwaI, AscI and PacI were done and subsequently supplied to TAFE-analyses using several glaA locus specific probes derived from pAB6-1(see Patent Application EP 0357127A1). No differences could be observed with respect to the size of the glaA hybridizing DNA fragments with the above mentioned restriction enzymes between the parent and the mutant strain. The largest hybridizing DNA fragment could be detected in all cases with the restriction enzyme SwaI: approximately 80 kb. The only observed difference is the intensity of the glaA hybridizing DNA band. Although the intensity of the hybridizing glaA bands is difficult to quantify accurately, the TAFE-autoradiographs clearly shows that the mutant strain *A. niger* CBS 646.97 contains additional copies of the observed glaA amplicon.

In addition, we couldn't find another restriction enzyme which cuts outside the detected glaA amplicon. This means that the glaA amplicon encompasses at least 80 kb in size or larger.

1.2 Modifications of glaA loci on the Various Amplicons of *A.niger* CBS 646.97 Strain.

1.2.a. Rationale.

As described previously (Patent Application EP 0635574A1) a genomic target gene can be deleted appropriately in A niger by using the "MARKER-GENE FREE" approach. In that patent application an example is extensively described how to delete glaA specific DNA sequences in the genome of *A. niger* CBS 513.88. Described replacement vector integrates into the *A. niger* glaA genomic sequence via a double cross-over homologous recombination. The deletion vector comprises DNA regions homologous to the glaA target locus and the amdS selectable marker gene driven by the gpdApromoter sequence. In addition, in this vector the amdS selectable marker gene is flanked at both sites by glaA sequences as direct DNA repeats to facilitate subsequently the appropriate elimination of the amdS marker gene.

Such vectors direct replacement of the glaA gene by the amdS marker gene. Subsequently, by performing the fluoroacetamide counter selection on these transformants, the amdS marker gene can be deleted properly by an internal recombination event between the 3'-glaA DNA direct repeats. This resulted in a MARKER-GENE FREE ΔglaA recombinant *A. niger* CBS 513.88 strain, possessing finally no foreign DNA sequences at all.

It's obvious that this "MARKER-GENE FREE" approach is especially useful for modifying and deleting host genomic sequences repeatedly.

This example describes the appropriate deletion of all glaA promoter and encoding sequences in *A. niger* CBS .646.97, in three successive transformation rounds by using a set of three "special designed" pGBDEL replacement vectors. For these three deletion rounds a set of three more or less the same glaA gene-replacement PGBDEL vectors were constructed and used. The reason to include in each pGBDEL vector an unique restriction enzyme recognition DNA sequence, is to recognize and visualize in derived ΔglaA recombinant *A. niger* strain each truncated glaA locus separately by Southern analyses (described in example 1.2.e). The unique restriction site in each PGBDEL vector is positioned at the 5'-border of the truncated glaA locus. However, in each PGBDEL vector, the included glaA sequences for directing targeting of the gene-replacement vector at one of the glaA loci, is slightly different. The consequence is that each truncated glaA locus in the *A. niger* host, is slightly different as well. The reason to include this slight difference is to visualize each truncated glaA locus by a rapid PCR test on colonies: the so-called "DNA-flag" test (FIG. 1). Although not essential, this incorporated DNA feature is especially helpful to monitor, with aid of the in this application described phenomenon of gene conversion events between the glaA amplicons in *A. niger*, the "building" process to amplify the (phytase) expression cassettes, which are targeted at one of these truncated glaA loci of the *A. niger* host. Details of this "building" process to derive rDNA strains for the production of enzymes, making use of the conversion events between glaA amplicons in *A. niger* is described below (examples 1.5 and 1.6).

1.2.b Description of glaA Replacement pGBDEL Vectors.

All constructed pGBDEL replacement vectors comprises:
- a 2 kb sized 5'-glaA target sequence from the HindIII site up to 200 bp in pGBDEL-5, or 180 bp in pGBDEL-9 and 140 bp in pGBDEL-11, upstream the unique XhoI site within the glaA promoter sequence;
- a 2 kb sized 3'-glaA target sequence from the glaA stop codon to SalI site;
- the amdS gene as selectable marker under the control of gpdA promoter;
- two 1 kb sized 3'-glaA DNA direct repeats to facilitate later on the removal of the amdS selectable marker gene and,
- an additional restriction site (BamHI in pGBDEL-5; SalI in pGBDEL-9 and BglII in pGBDEL-11) positioned at the glaA truncation.

By using these PGBDEL replacement vectors, 4.3 kb glaA sequences in the *A. niger* host which will become deleted, which includes the 2 kb sized glaA promoter sequences (ranging from 200, 180 bp or 140 bp in pGBDEL-5, pGBDEL-9 and pGBDEL-11, respectively, upstream the XhoI) up to the ATG start codon and the entire glaA encoding sequence. For a schematic view FIG. 2).

1.2.c. Construction of pGBGLA Intermediate Vectors.

For the construction of the intermediate vector pGB-GLA16 two oligo nucleotides (30/31) were synthesized containing the enzyme restriction sites: NotI, EcoRI, KpnI, and XhoI. Oligo were adapted with a HindIII restriction site at 5'-end and with an EcoRI restriction site at 3'-end. By insertion of this oligo nucleotide into pTZ18R the EcoRI site will be destroyed.

Both oligo nucleotides 30 and 31 were cloned into the EcoRI and HindIII sites of plasmid pTZ18R. Control digests were performed to be certain whether the desired enzyme restriction sites for KpnI, XhoI, NotI and HindIII were incorporated appropriately and the EcoRI site destroyed. Derived plasmid was designated pTM1 (see FIG. 3) From pTM1, the EcoRI and KpnI DNA fragment was isolated and purified by gel electrophoresis after digestion with both restriction enzymes, to insert the EcoRI/KpnI fragment of pGBDEL4L comprising the $P_{gpdA}$/amdS sequence. The construction of pGBDEL4L is described extensively in our previous Patent Application (EPA 0635574A1). pGBDEL4L was digested with EcoRI/KpnI and XhoI (the latter one to avoid molecular cloning of another DNA fragment of pGBDEL4L possessing the same size). The correct EcoRI/KpnI DNA fragment, comprising the PgpdA/amdS sequence, was purified by gel electrophoresis and cloned into the EcoRI/KpnI sites of pTM1. This intermediate vector was designated pGBGLA16 (see FIG. 3).

To insert the 2.2 kb sized 3'-glaA sequence appropriately into the pGBGLA16, the fragment needs some modifications first. A fusion PCR was performed with pAB6–1 as template and two sets of oligo nucleotides as primers (32/33 and 34/35), to destroy the KpnI restriction site within 2.2 kb 3'-glaA sequence, and to create appropriate cloning sites at the 5'-boundary (KpnI) and at the 3'-boundary (XhoI, HindIII). Template pAB6–1 comprises a 16 kb large HindIII fragment in pUC19, containing the glaA genomic locus (molecular cloning is extensively described in EPA 0357127A1).

In the first PCR, oligo nucleotides 32 and 33 were used as primer set to amplify a part (1 kb) of the 3'-glaA sequence. In the second PCR oligo nucleotides 34 and 35 were used to amplify the remaining 1.2 kb sequence of the 3'-glaA flanking.

After purification by gel electrophoresis both amplified fragments were used as template in a fusion PCR with oligo nucleotides 32 and 35 as primer set. A schematic presentation of the PCR fusion is presented in FIG. 4. The obtained 2.2 kb 3'-glaA PCR fusion fragment was purified by gel electrophoresis, digested with KpnI and XhoI and inserted by molecular cloning into the KpnI/XhoI sites of pGBGLA16, yielding pGBGLA18 (see FIG. 4).

1.2.d. Construction of glaA Replacement PGBDEL Vectors.

In obtaining the three final PGBDEL vectors, the 5'-glaA target sequence, an unique restriction site for each vector, and the 1 kb 3'-glaA sequence as direct repeat have to be inserted into the HindIII/NotI sites of pGBGLA18. To this end, three separate fusion PCR's were carried out to construct pGBDEL5, -9 and -11.

Construction of pGBDEL5.

A $1^{th}$ PCR was carried out to modify the 5'-glaA target sequence at the 3'-border with two synthetic oligo nucleotides: 36, containing a part of the nucleotide sequence of pUC19, the HindIII site of the 5'-glaA sequence and 37 matching about 200 bp upstream the XhoI site in the glaA promoter, which comprises an additional BamHI site, stop-codons in all reading frames and the first 18 nucleotides (5'-border) of the 1 kb 3'-glaA direct repeat. The 2nd PCR was performed to modify the 3'-glaA direct repeat at the 5'-border with oligo nucleotides 38, which is the reverse of 37 and oligo nucleotide 39, matching with sequences around the EcoRI site of the 3'-glaA direct repeat, added with the restriction sites XbaI and NotI for appropriate cloning into pTZ18R and pGBGLA18 respectively. In both PCR amplification pAB6-1 was used as template. Amplified DNA fragments of both PCR's were separated by gel electrophoresis and used as templates in the fusion PCR with 36 and 39 as primers. The obtained 3 kb sized DNA fusion fragment was purified by gel electrophoresis, digested with HindIII and NotI and subsequently molecular cloned into the appropriate sites into pGBGLA18, yielding the first gene replacement vector pGBDEL5 (see FIG. 5).

Construction of pGBDEL9.

The $1^{th}$ PCR was carried out with oligo's 36 and 49 (as described above) matching about 180 bp upstream the XhoI site in the glaA promoter, which comprises an additional SalI site, stop-codons in all reading frames and the first 18 nucleotides (5'-border) of the 1 kb 3'-glaA direct repeat. The 2nd PCR was peformed to modify the 3'-glaA direct repeat at the 5'-border with oligo nucleotides 50, which is the reverse of 49 and oligo nucleotide 39.

In both PCR amplifications pAB6-1 was used as template. Amplified DNA fragments of both PCR's were seperated by gel electrophoresis and used as templates in the fusion PCR with oligo's 36 and 39 as primers. The obtained 3 kb sized DNA fusion fragment was purified by gel electrophoresis, digested with HindIII and NotI and subsequently molecular cloned into the appropriate sites into pGBGLA18, yielding the second glaA gene replacement vector pGBDEL9 (see FIG. 6).

Construction of pGBDEL11.

The $_1$th PCR was carried out with oligo's 36 and 51 matching about 140 bp upstream the XhoI site in the glaA promoter, which comprises an additional BglII site, stop-codons in all reading frames and the first 18 nucleotides (5'-border) of the 1 kb 3'-glaA direct repeat. The $2^{nd}$ PCR was performed to modify the 3'-glaA direct repeat at the 5'-border with oligo nucleotides 52, which is the reverse of 51 and oligo nucleotide 39.

In both PCR amplification pAB6-1 was used as template. Amplified DNA fragments of both PCR's were separated by gel electrophoresis and used as templates in the fusion PCR with 36 and 39 as primers. The obtained 3 kb sized DNA fusion fragment was purified by gel electrophoresis, digested with HindIII and NotI and subsequently molecular cloned into the appropriate sites into pGBGLA18, yielding the third gene replacement vector pGBDEL11 (see FIG. 7).

1.2.e Deletion of glaA Promoter and Coding Sequences and Incorporation of Specific "DNA-flags" in *A. niger*.

In this example the successful deletion of all three glaA genes present in *A. niger* 646.97 is described by using the pGBDEL vectors and the "MARKER-GENE FREE" technology in three successive transformation rounds.

By linearizing pGBDEL vectors with XhoI and HindIII and the fact that the rDNA cassettes are flanked by DNA sequences homologous to the glaA target locus of the host genome, pGBDEL vectors will become integrated by a double cross-over event at one of the glaA loci of the host, resulting in a replacement of the glaA sequence by the truncated glaA loci of the pGBDEL vectors. However, the frequency of targeting of a pGBDEL vector by a double crossing-over event is limited and dependent on the number of the glaA genomic target loci of the host. So, although linearized vectors are used comprising 2 kb sized glaA homologous regions at both flanks, still the majority of the generated transformants contain random integrated vectors.

However, the transformant possessing the desired genetic feature could be easily selected and verified, by applying a) the PCR-based DNA-flag test, b) the target specific PCR-procedure and c) by detailed Southern analyses as indicated in Materials & Methods.

Finally, once the appropriate transformant was genetically verified the amdS marker gene was removed by applying the fluoroacetamide counter selection procedure. Due to the incorporated 3-glaA DNA repeats, flanking the $P_{gpdA}$/amdS marker gene cassette, after each round the amdS selection marker was eliminated by an internal recombination event. Thus obtained modified *A. niger* strains were subjected to successive transformation rounds to eliminate and modify the remaining glaA loci.

Modification of the First glaA Amplicon in *A. niger* CBS 646.97 with pGBDEL5.

*A. niger* CBS 646.97 was transformed with 5 µg linearized (HindIII/XhoI) pGBDEL5 DNA. Transformants were selected on selective plates containing acetamide and spores prepared after repeated growth on selective medium.

A restricted number of transformants were selected and isolated chromosomal DNA extensively analysed by Southern analyses using KpnI and BamHI digests and the 5'-glaA HindIII/XhoI and the 2.2 kb SalI 3'-glaA fragments as probes. See FIG. 8 for comparising the BamHI hybridization patterns of the ΔglaA loci of the host strain and the two remaining ΔglaA loci of the transformant.

Figure 9:
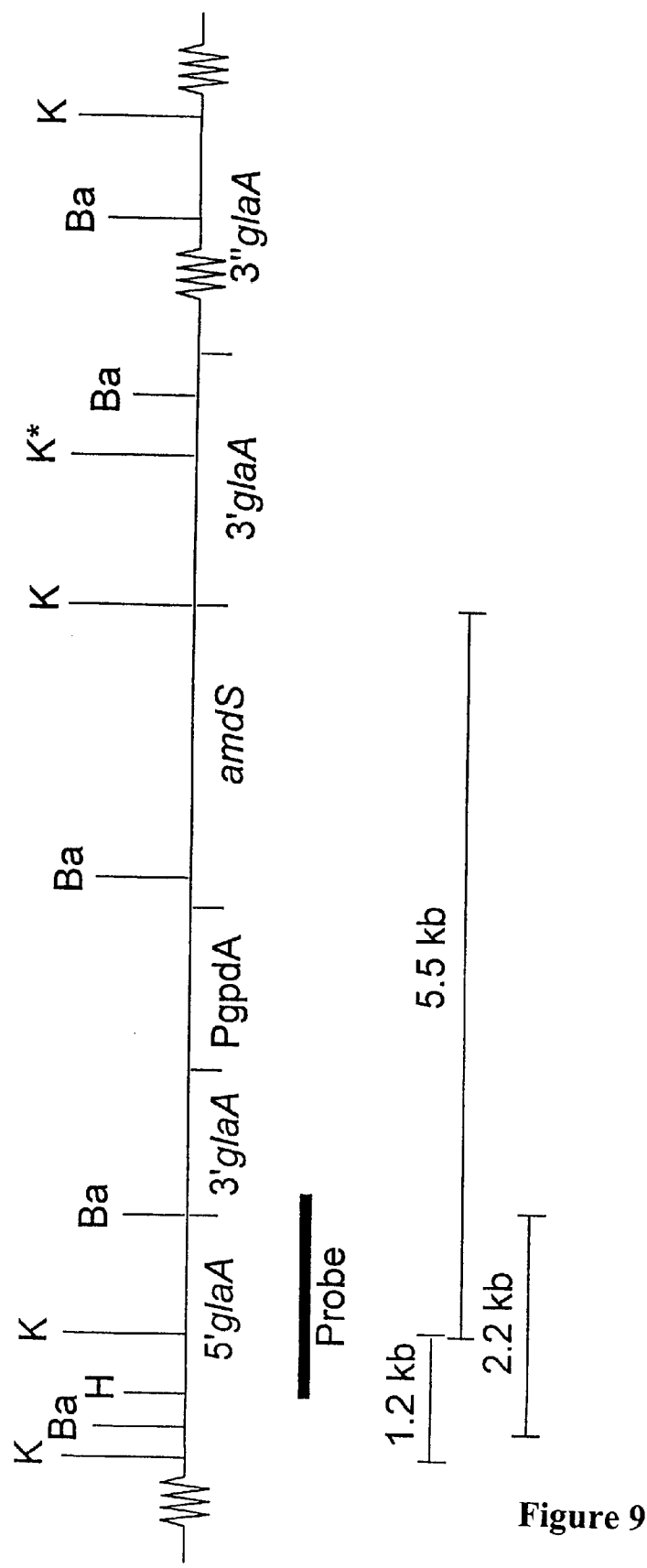
Figure 9:
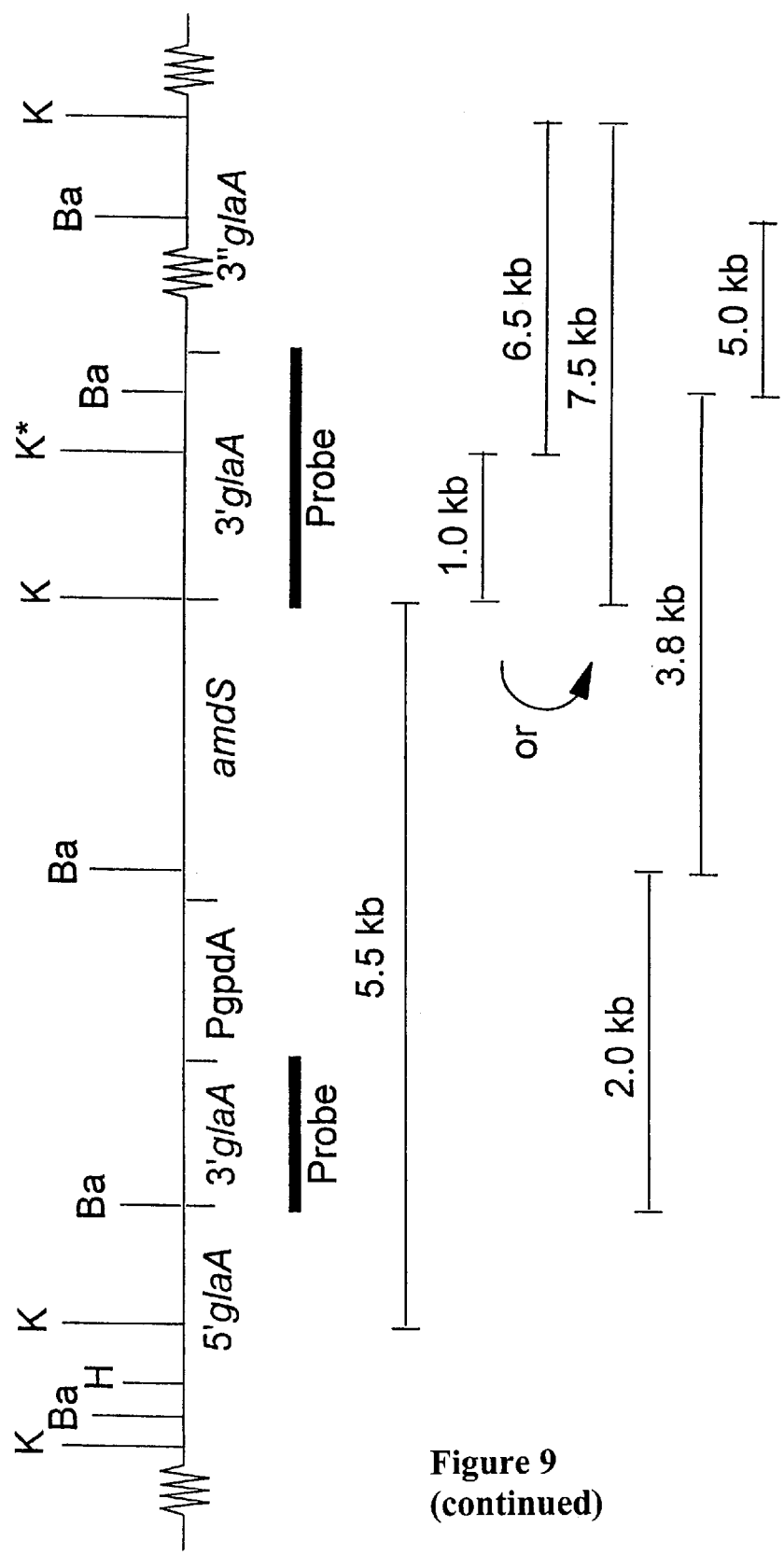

Transformants showing the expected hybridization patterns as indicated in FIG. 9 were selected.

Figure 10:
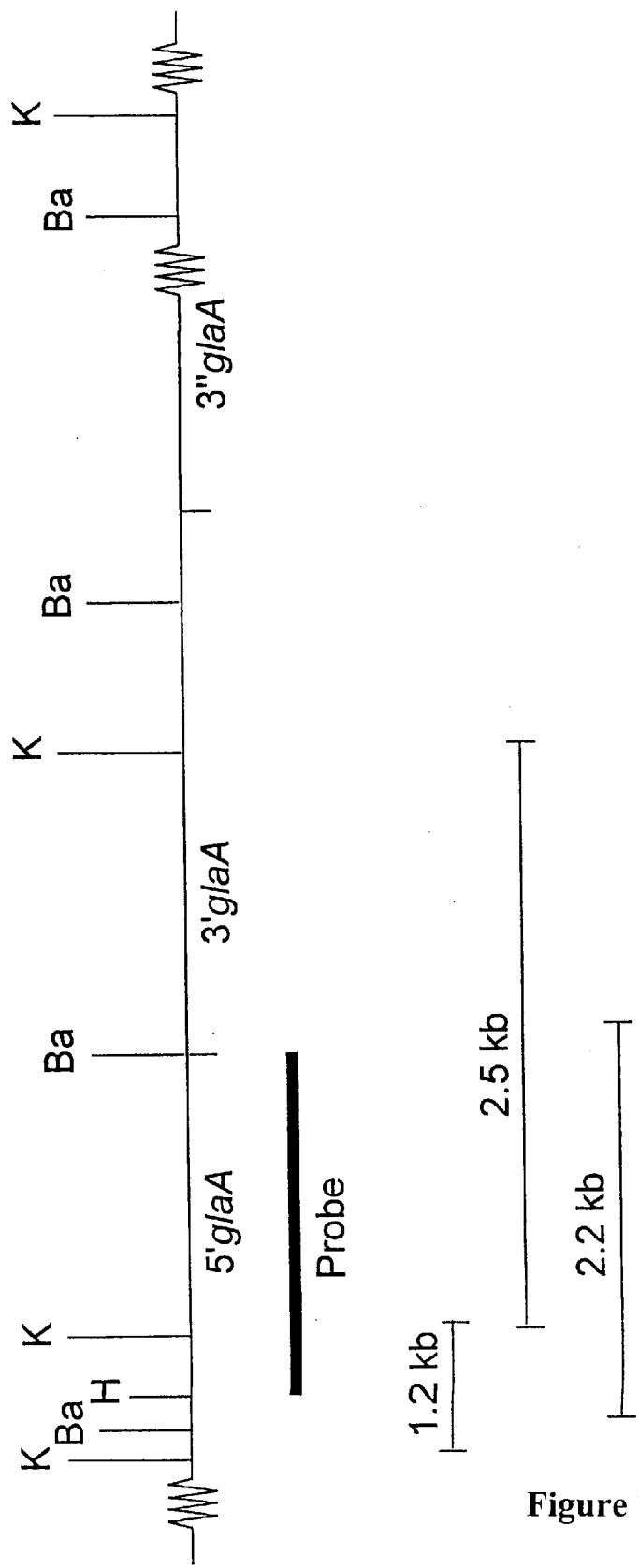
Figure 10:
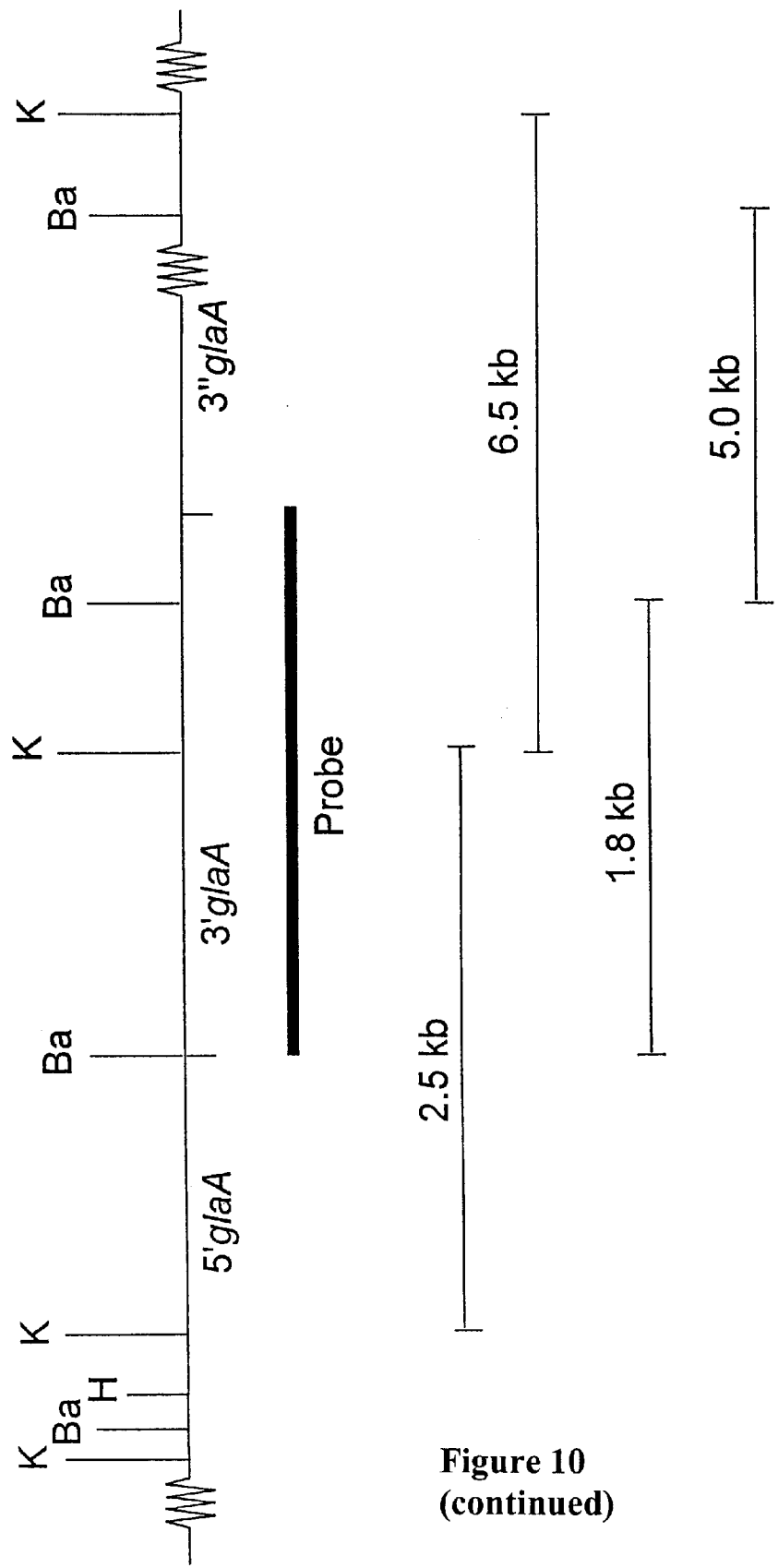

Subsequently, on these transformants the counter slection procedure was performed. Spores were seeded on fluoroacetamide containing medium (for details see Materials & Methods). On average 1–2% of the seeded spores were able to grow on these selective conditions. Cassette PCR analyses, performed directly on mycelium of these growing colonies with amdS specific oligo's 15 and 16 as primers, revealed that all growing cells are indeed recombinant cells, which have lost the amdS marker gene. Surprisingly, however, detailed Southern analysis on many recombinant cells showed that in most cases (frequency about 90%) hybridization patterns were observed which are characteristic only for the parental strain 646.97, instead of the expected pattern for one truncated glaA locus and the two remaining intact glaA loci. In addition, the intensities of hybridizing DNA fragments pointed out that the number of glaA amplicons was not diminished in these amdS-negative strains. Approximately 10% of the cells show the expected hybridization pattern as indicated in FIG. 10. So, in those cases the amdS marker-gene was indeed deleted via the internal recombination event over the flanking 3'-glaA direct repeats, as expected.

This unexpected recombination event in most of the amdS negative strains can be explained only by the occurrence of a genetic phenomenon, called gene-conversion. A feature which is used later on (see example 1.5 and 1.6) to amplify enzyme encoding expression cassettes targeted at one of the truncated glaA amplicons of the A. niger CBS 646.97 host.

One amdS-negative strain, showing the hybridization patterns for one truncated glaA locus and two intact glaA loci as presented in FIG. 10, was designated as A. niger GBA-201 and subjected to a second transformation with pGBDEL-9.

Modification of the Second glaA Amplicon in A. niger CBS 646.97 with pGBDEL9.

A. niger GBA-201 was transformed with 5 µg linearized (HindIII/XhoI) pGBDEL9 DNA. Again transformants were selected on selective plates containing acetamide and spores prepared after repeated growth on selective medium. Because targeting of pGBDEL9 can occur also on the previous "BamHI-marked glaA truncated locus of the host, only those transformants were selected and analysed by Southern analyses, showing still the presence of that truncated "BamHI" glaA locus. To this end, first the PCR-based "DNA-flag" test was performed on mycelium of these transformants. Only those transformants showing the 200 bp DNA fragment characteristic for the "BamHI" truncated glaA locus were analyzed by the PCR-methods, followed by an extensive Southern analyses as indicated above.

Subsequently, spores of the transformant showing the correct hybridization pattern (FIG. 10) were seeded on fluoroacetamide containing medium (for details see Materials & Methods). Again on average 1–2% of the seeded spores were able to grow on these selective conditions. All of them appeared to have lost the amdS gene as revealed after applying the cassette PCR-test on mycelium of these colonies.

As second selection criterium the "DNA-flag" test was performed. Only those transformants were subjected to detailed Southern analyses as described as above, showing the desired DNA-flag pattern (2 bands of 200 and 220 bp) each characteristic for the presence of the "BamHI" truncated glaA amplicon and the "SalI" truncated glaA amplicon, respectively.

One amdS-negative strain, showing the hybridization patterns for two truncated glaA amplicons and one intact glaA amplicon (FIG. 12), was designated A. niger GBA-202 and subjected to a third transformation with pGBDEL-11. Modification of the Third glaA Amplicon in A. niger CBS 646.97 with pGBDEL11.

A. niger GBA-202 was transformed with 5 µg linearized (HindIII/XhoI) pGBDEL-11 DNA. Again transformants were selected on selective plates containing acetamide and spores prepared after repeated growth on selective medium. Also in this case targeting of pGBDEL11 can occur on one of the previous glaA truncated amplicons of the host. By performing the "DNA-flag" test, only those transformants were selected and analysed by Southern analyses, which still show the presence of the 200 and 220 bp fragments, representing the two previously truncated "BamHI" and "SalI" glaA amplicons.

Figure 13:
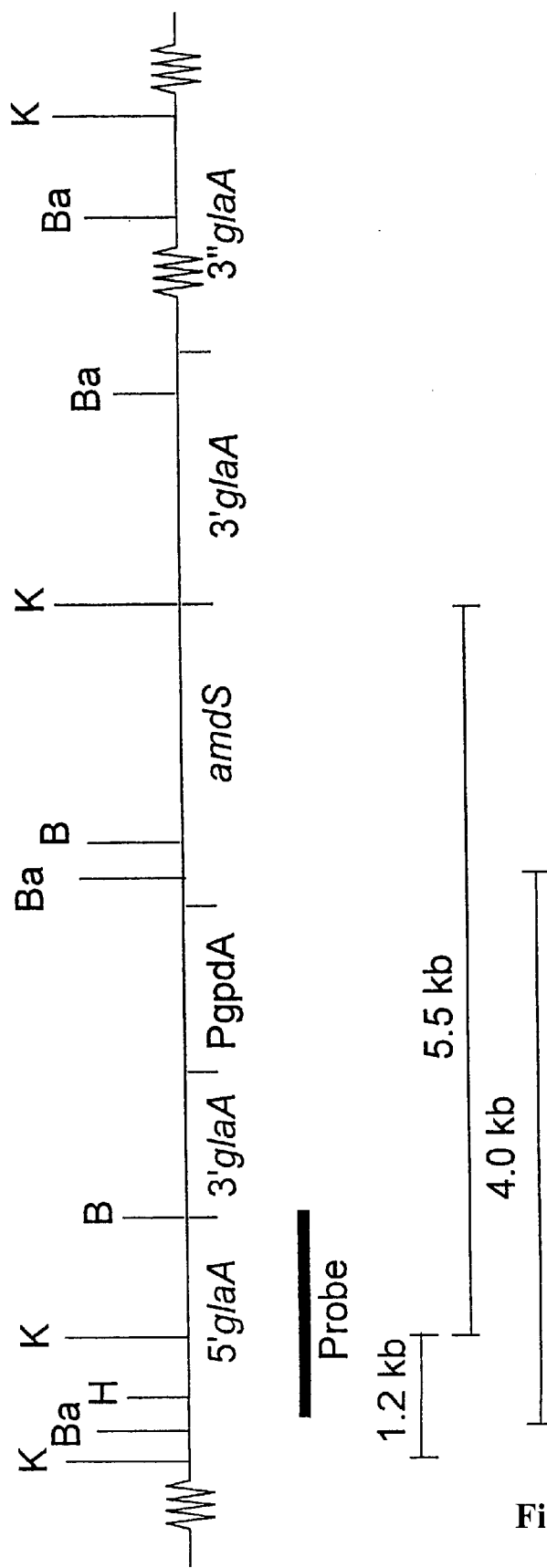
Figure 13:
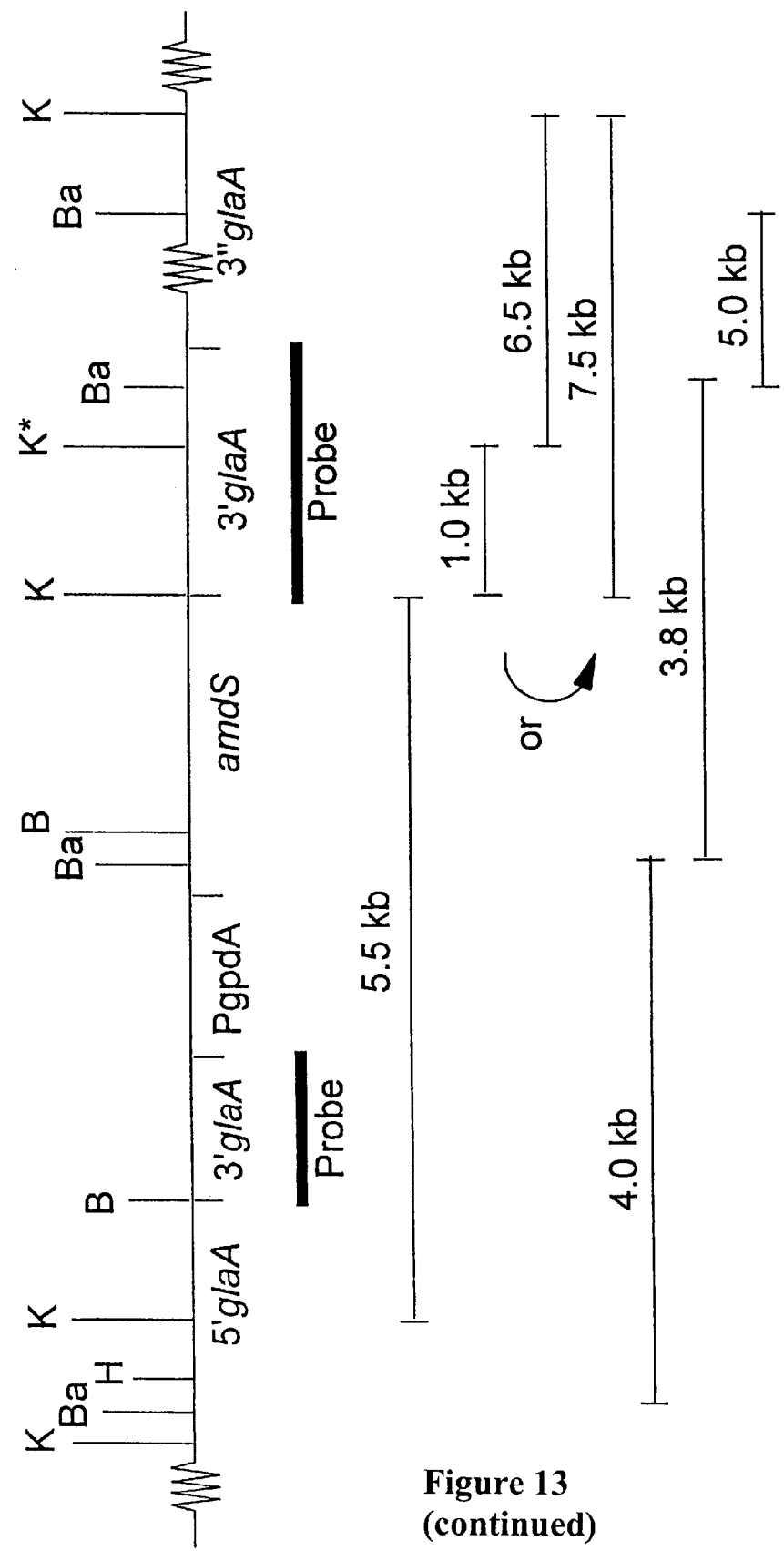

Transformant showing the correct hybridization patterns as indicated in FIG. 13 were subjected to the counter selection procedure to obtains marker-gene free recombinants. Again on average 1–2% of the seeded spores were able to grow on these selective conditions. All of them appeared to have lost the $P_{gpdA}$/amdS marker gene cassette as revealed after applying the amdS cassette PCR-test on mycelium of these colonies.

As second selection criterium the "DNA-flag" test was performed. Only those transformants were subjected to detailed Southern analyses as described above, showing the desired DNA-flag pattern of 3 bands (200, 220 and 300 bp) referring to the presence of the "BamHI" as well as to "SalI" and "BglII" truncated glaA amplicons, respectively. One amdS-negative strain, showing the hybridization patterns (FIG. 14) for all three truncated glaA amplicons, was designated as A. niger ISO-505.

1.3. Description and Construction of pGBAAS-1 and pGBTOPFYT-1 Expression Vectors 1.3.a Rationale.

pGBTOP vectors, comprising the expression cassette for an enzyme, are introduced into the A. niger host strains by co-transformation with an amdS selectable marker-gene containing vector, which is designated as pGBAAS-1. Both vectors comprise two DNA domains homologous to the glaA locus of A. niger host strain to direct targeting of the linearized plasmid to one of the truncated glaA loci of A. niger ISO-505. These domains, each approximately 2 kb in size, are homologous to the downstream non-coding glaA sequence, and are specified as 3'- and 3"-glaA domains. Between these domains a unique restriction site is incorporated (XhoI in pGBAAS-1 and HindIII in pGBTOPFYT-1) to obtain, after removal of the E. coli pTZ18R cloning vector prior to transformation by digestion, DNA enzyme restriction ends which are almost complementary to the glaA target locus of the host.

In pGBAAS-1 the amdS gene is driven by the strong gpdA promoter. By using such a promoter the majority of obtained transformants will possess just a single integrated selection-marker cassette. Having such transformants are crucial for performing the next step: selecting for MARKER-GENE FREE recombinants strains by applying the previously described MARKER-GENE FREE technology. The presence of multiple amdS genes, will certainly affect the frequency to remove them in the "one step counter selection procedure" or will be even impossible.

In pGBTOPFYT-1 phyA is driven by $P_{glaA}$. As indicated above already, the composition of this vector is designed in such a way that linearized expression cassette become integrated at one of the glaA target loci in A. niger ISO-505. To get transformants possessing multiple copies of the expression cassette versus a single copy of the co-vector (necessary to obtain finally MARKER-GENE FREE recombinant strains) in just one transformation round and both targeted to the same glaA target locus of the host genome, the ratio of linearized DNA fragments of both cassettes is crucial.

3.1.b. Construction of the Integration Vector pGBAAS-1.

All details concerning the construction of pGBAAS-1 can be found in one of our previous patent applications EPA 0635574A1. In this patent application the construction of the amdS selection marker-gene vector pGBGLA-50 is described extensively. For nomenclature reasons only, later on this vector is renamed as pGBAAS-1 (Aspergillus AmdS Shuttle). See FIG. 15 for the physical map.

3.1.c. Construction of the Integration Vector PGBTOPFYT-1.

Also the construction of pGBTOPFYT-1 can be found in the same patent applications as mentioned above. In that patent application the construction of the phytase expression vector pGBGLA-53 is described extensively. Again for nomenclature reasons only, this expression vector was later on renamed as pGBTOPFYT-1 (Tool to Over express Proteins). See FIG. 16 for the physical map.

1.4 Development of a MARKER-GENE FREE, Phytase Producing A. niger Strain, Containing one or Multiple Phytase Expression Cassettes all Targeted at One of the Truncated glaA Amplicons of A. niger ISO-505

1.4.a. Rationale.

The aim of this example is to show that expression cassettes (just one or even multiple copies) can be directed perfectly to a predefined target locus in the genome of a host cell by co-transformation with a vector possessing a selectable marker gene. The second part shows how to remove the selectable marker gene cassette by an internal recombination event without loosing the targeted (multiple) enzyme expression cassette(s).

The target locus of choice in this case is the 4 kb glaA sequence located just downstream the glaA stop codon. Integration of both linearized plasmids pGBTOPFYT-1 and pGBAAS-1 occurs via a single cross-over event at one of the truncated and marked glaA loci of the A. niger ISO-505 strain.

To obtain finally selection MARKER-GENE FREE recombinants, only those transformants will be selected for the subsequent fluoroacetamide counter selection procedure, possessing both plasmids targeted in an appropriate way at the same marked glaA locus of the host genome.

1.4.b Co-transformation of A. niger ISO-505 with Linearized pGBAAS-1 and pGBTOPFYT-1 DNA.

Both plasmids, pGBAAS-1 and pGBTOPFYT-1, were linearized by digestion with XhoI and HindIII, respectively. The 2.8 kb E. coli cloning sequence was removed prior to transformation by gel electrophoresis. A ratio of 1 to 5 µg linearized DNA of pGBAAS-1 and pGBTOPFYT-1, respectively, was used to transform A. niger ISO-505 as described in Materials & Methods. Transformants were selected on acetamide plates. Spores of these transformants were isolated by plating the individual colonies on PDA-plates. Approximately 500 transformants were subjected to the cassette PCR-test.

1.4.c Selection for co-transformants.

Transformants possessing the amdS marker gene as well as the phyA expression cassette were identified by the cassette PCR test using phytase specific oligo nucleotides 42/43 as primers. Positive transformants containing one or multiple phyA expression cassettes will show a specific DNA band of 482 bp in size. Co-transformation frequencies varied between 10 to 50%.

1.4.d Selection of Targeted amdS$^+$, phyA$^+$ co-transformants.

On identified co-transformants, targeting PCR tests were performed using two sets of oligo nucleotides 46/47 (primer set 1) and 46/48 (primer set 2). Co-transformants showing a positive result (amplification of a 4.2 kb DNA fragment, see FIG. 17) with one these two primer sets were selected. A negative result indicates that all cassettes are integrated randomly, a positive result with primer set 1 or 2, implies that either the phyA or amdS is located adjacent to the glaA target locus, respectively . Between 5–50% of the co-transformants appeared to be positive. A limited number of identified strains were selected for extensive Southern-analyses.

1.4.e Genetic Analyses of Targeted amdS and phyA Targeted co-transformants by Southern Analyses.

Chromosomal DNA was isolated and Southern analyses performed using BglII digests hybridized with the amdS and the 2.2 kb SalI/XhoI 3"-glaA DNA fragment as probe. Schematic drawings of six mostly observed DNA hybridization patterns are shown in FIGS. 18 to 23. Co-transformants showing the hybridization pattern characteristic for possessing a single amdS copy and one or multiple phyA cassette(s) (FIGS. 20–23). were subjected to fluoroacetamide counter-selection procedure to remove finally the amdS selection marker gene.

1.4.f Selection of amdS Gene Free (amdS$^-$) Phytase Producing Strains.

Recombination over the direct repeats, created by targeted integration of the amdS expression cassette, will result in the loss of the amdS cassette and can be selected on fluoroacetamide medium. Here we describe the selection of amdS free recombinant strains, which still contain the adjacent (multiple) integrated phyA expression cassette(s) by using the Fluoroacetamide counter selection procedure. Spores of selected targeted amdS$^+$/phyA$^+$ co-transformants were plated onto fluoroacetamide plates. Initially, growing colonies were analyzed by several successive PCR-based tests. First, all progenies were tested for the genotype, amdS$^-$. The selection for amdS$^-$ genotypes were done by performing the cassette PCR test on colonies using the amdS specific primers as described in Material & Methods. Surprisingly, however, in the subsequent PCR-based "DNA-flag" test, it appeared that in the majority of the progenies an entire glaA amplicon was lost as well. In addition, in most amdS$^-$ recombinants the targeted phyA cassettes were lost as well, as appeared in the third PCR-test using the phyA specific primer set.

These results can be explained only by the occurrence of one phenomenon, which is known as gene-conversion. In several cases a rather large DNA fragment or even the size of the entire glaA amplicon ($\geq 80$ kb) was replaced by another glaA amplicon. In most progenies (over 90%), however, it appeared that an entire glaA amplicon was deleted. Hence, to cover observed results entirely, terms as amplicon conversion and deletion are more appropriate. Observed phenomenon was used to determine whether all amdS and phyA cassettes in co-transformants are targeted in the same truncated glaA locus and in which one of them. To determine this, just one or two fluoroacetamide resistant colonies of each co-transformant was tested which of them will result in the genotype: amdS$^-$/phyA$^-$/glaA-amplicon$^{2+}$ by performing a mixed PCR-test using phyA and "DNA-flag" oligo nucleotides primer sets. Results showed that co-transformants can be realized possessing amdS and phyA cassettes integrated in one of the three glaA amplicons.

Subsequently, from such identified co-transformants, additional progenies were tested by applying a mixed PCR test with the phyA and "DNA-flag" primer sets. The occurrence of the desired amdS$^-$/phyA$^+$/glaA-amplicon$^{3+}$ genotype varied strongly (1 to 20%) among the progenies of the individual co-transformants. This frequency appeared to be strongly dependent on the genetic composition of the amdS and phyA cassettes within the glaA amplicon of the pre-selected co-transformants.

In case, in a co-transformant multiple cassettes have become targeted at one glaA locus many repeats are created.

The consequence for the fluoroacetamide counter selection procedure is that loss of the amdS cassette can occur differently, resulting in amdS− progenies possessing a different number of phyA cassettes.

For this reason, of each pre-selected co-transformant, several progeny recombinants were selected (all showing the desired amdS−/phyA+/glaA amplicon$^{3+}$ genotype) but containing different number of remaining phyA cassettes.

Pre-selection for such progeny strains could be easily done by comparing the difference in intensity of the amplified phyA specific DNA bands to the DNA bands representing the three glaA amplicons in the above described PCR test.

Figure 24:
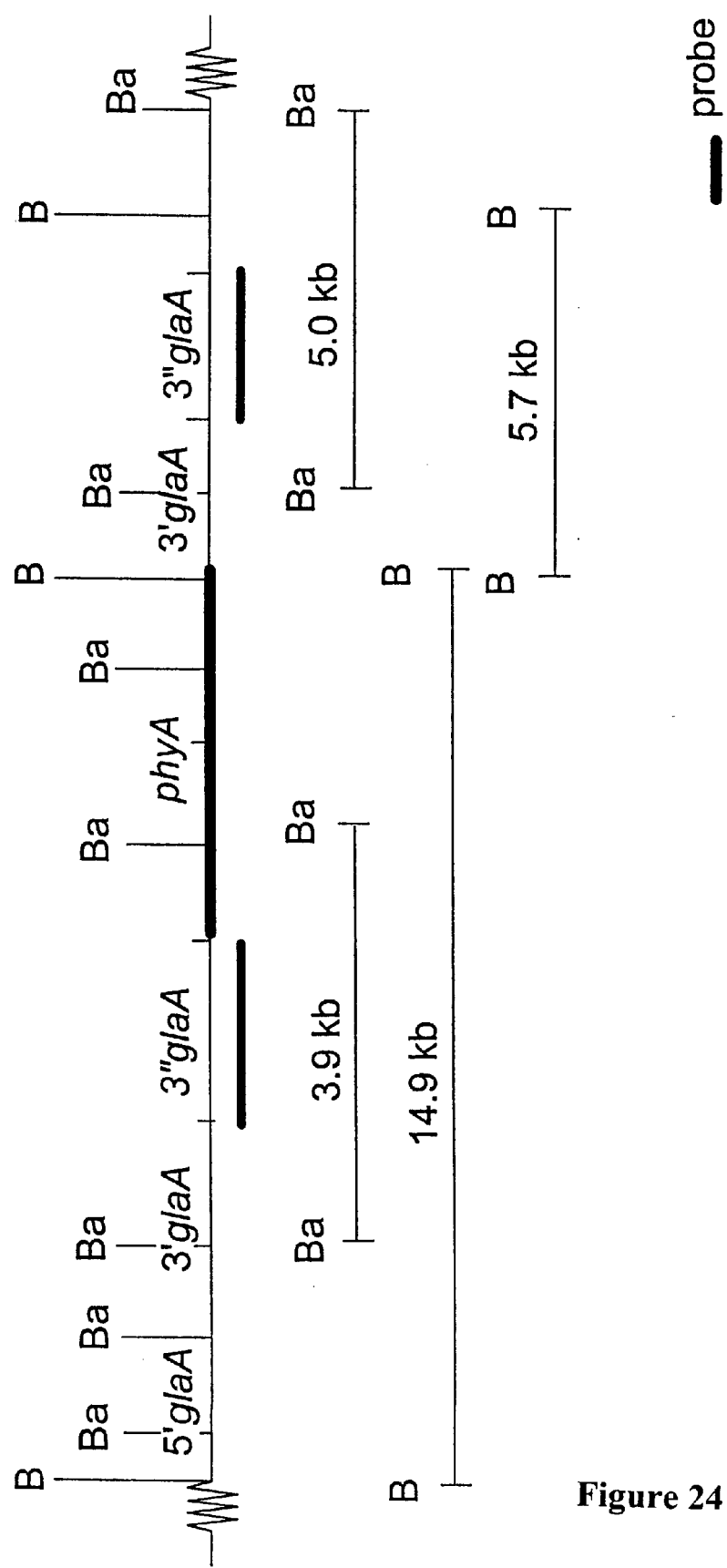
Figure 24:
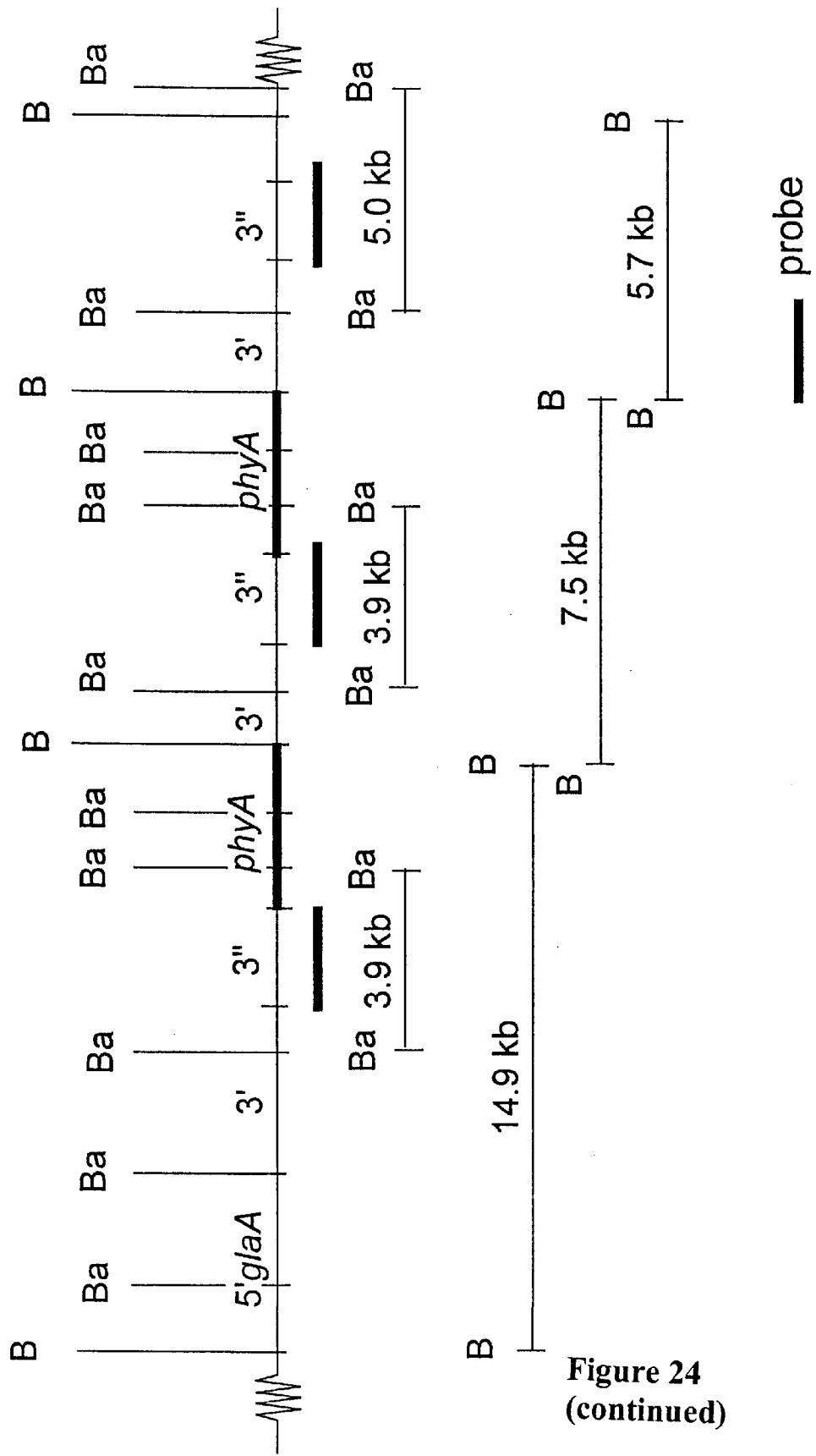
Figure 24:
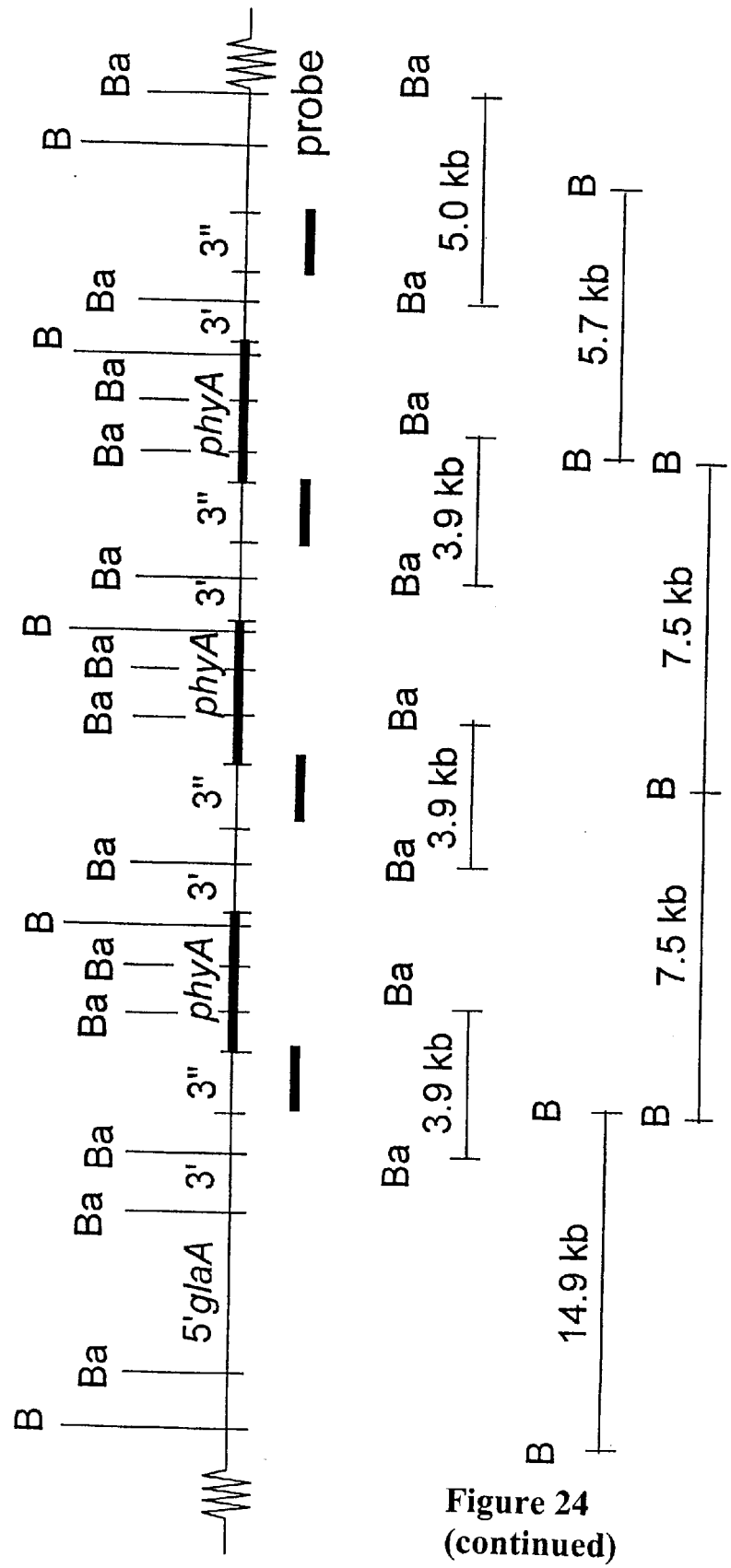

Finally, to confirm the genetic composition of selected amdS progenies, Southern analyses were done on chromosomal DNA digested with BamHI and BglII, hybridized with a 2.2 kb SalI/XhoI 3'-glaA DNA fragment as specific probe. Strains showing the hybridization pattern as indicated in FIG. 24 for having 1, 2 or 3 phyA cassettes targeted in one the BamHI-marked glaA amplicon, were selected and designated as *A. niger* NP505-1, -2 and -3, respectively.

These strains, together with those which possess the phytase cassettes in one of the two other glaA amplicons, were subsequently tested for their ability to produce phytase.

Shake flask fermentations were carried out as indicated in Materials & Methods. Measurement of the phytase activity in the supernatant revealed that all strains produce the same amount of phytase (100 U/ml) par phyA gene copy and appeared to be independent of the glaA amplicon in which the phyA genes are localized.

1.5 Selection of Convertants Comprising an Increase in Phytase Cassette from 1 to 2.

1.5.a Rationale.

The copy-number of an expression cassette targeted at a DNA amplicon can be increased through gene conversion. Consequently, production of the enzyme encoded by the gene can increase. Here we describe the selection and characterization of phyA convertants, showing an enhanced production of phytase.

1.5.b Selection of Putative phya Convertants.

As an example, strain *A. niger* NP505-2 was chosen. Recombinant strains containing less or more phyA cassettes targeted at another glaA amplicon can be used as well. Spores of *A. niger* strain NP505-2, containing two phyA cassettes targeted at the BamHI-marked glaA amplicon were seeded onto plates containing PDA medium and after 2–3 days the DNA-flag PCR test was performed on individual colonies using the phyA DNA-flag specific primers (see Materials & Methods).Using this method a genetic exchange (conversion/amplification or deletion) between the three marked glaA-amplicons can be visualized quite rapidly. Although the frequencies of obtained genotypes vary strongly, on average we observed that over 95% of the tested colonies show no change at all of all three glaA amplicons. 5% of the progenies showed either a deletion of one or two glaA amplicons, or an amplification of one of the glaA-amplicons and the desired convertant was detected as well, as result of a conversion between the "BamHI-marked" glaA locus and one of the other two glaA amplicons (an example of each is presented in FIG. 25).

1.5.c Southern Analyses of phyA Convertants.

To determine whether the copy number of phyA in these convertants are doubled as well, several of such convertants (genotype BamHI$^{2+}$/SalI$^{+}$/BglII$^{-}$ or BamHI$^{2+}$/SalI$^{-}$/BglII$^{+}$) were subjected to extensive Southern analyses using BamHI and BglII digests probed with the glaA specific HindIII/XhoI 5' glaA DNA fragment and the SalI/XhoI 3"-glaA DNA fragment, respectively.

Figure 25:
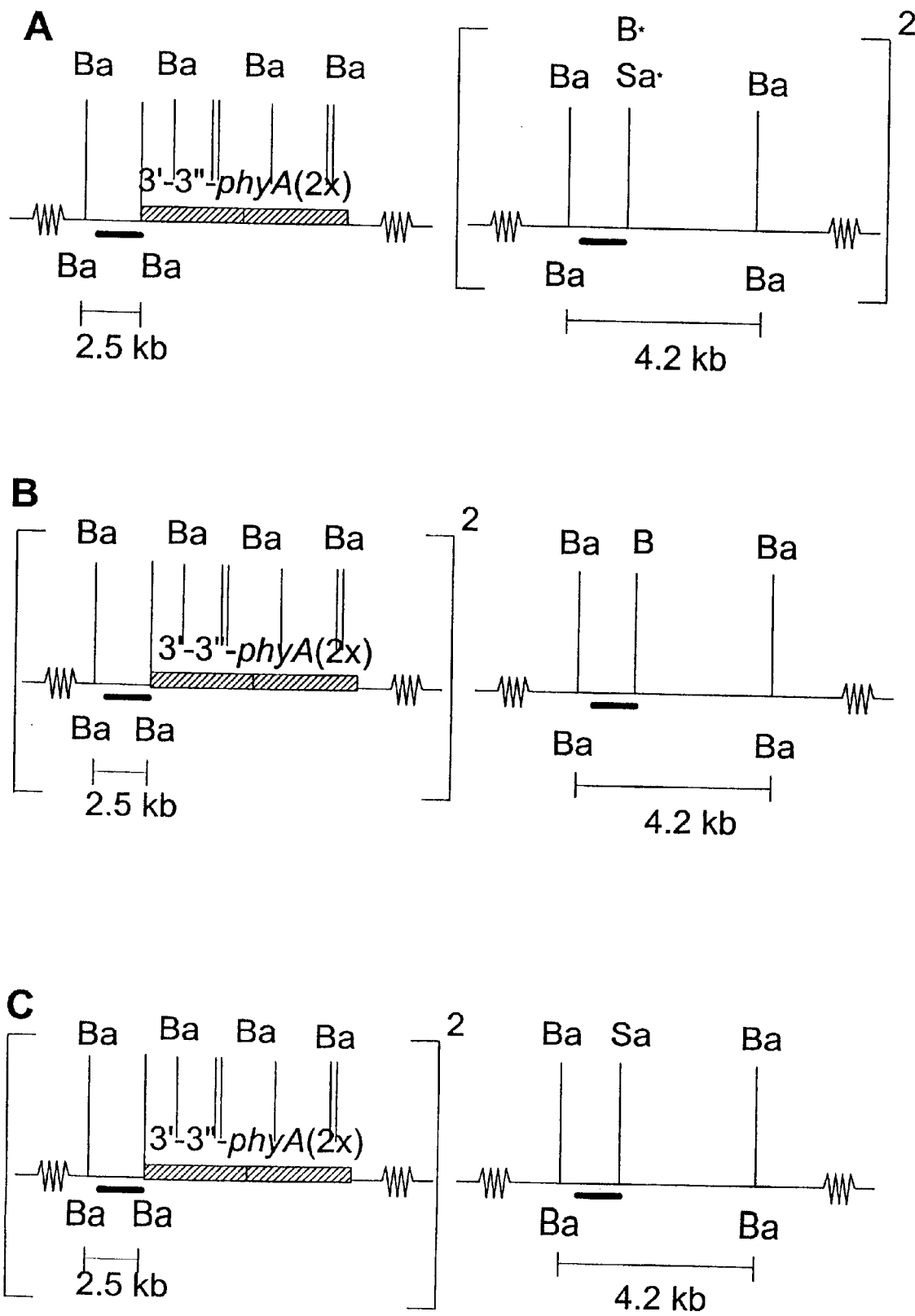
Figure 26:
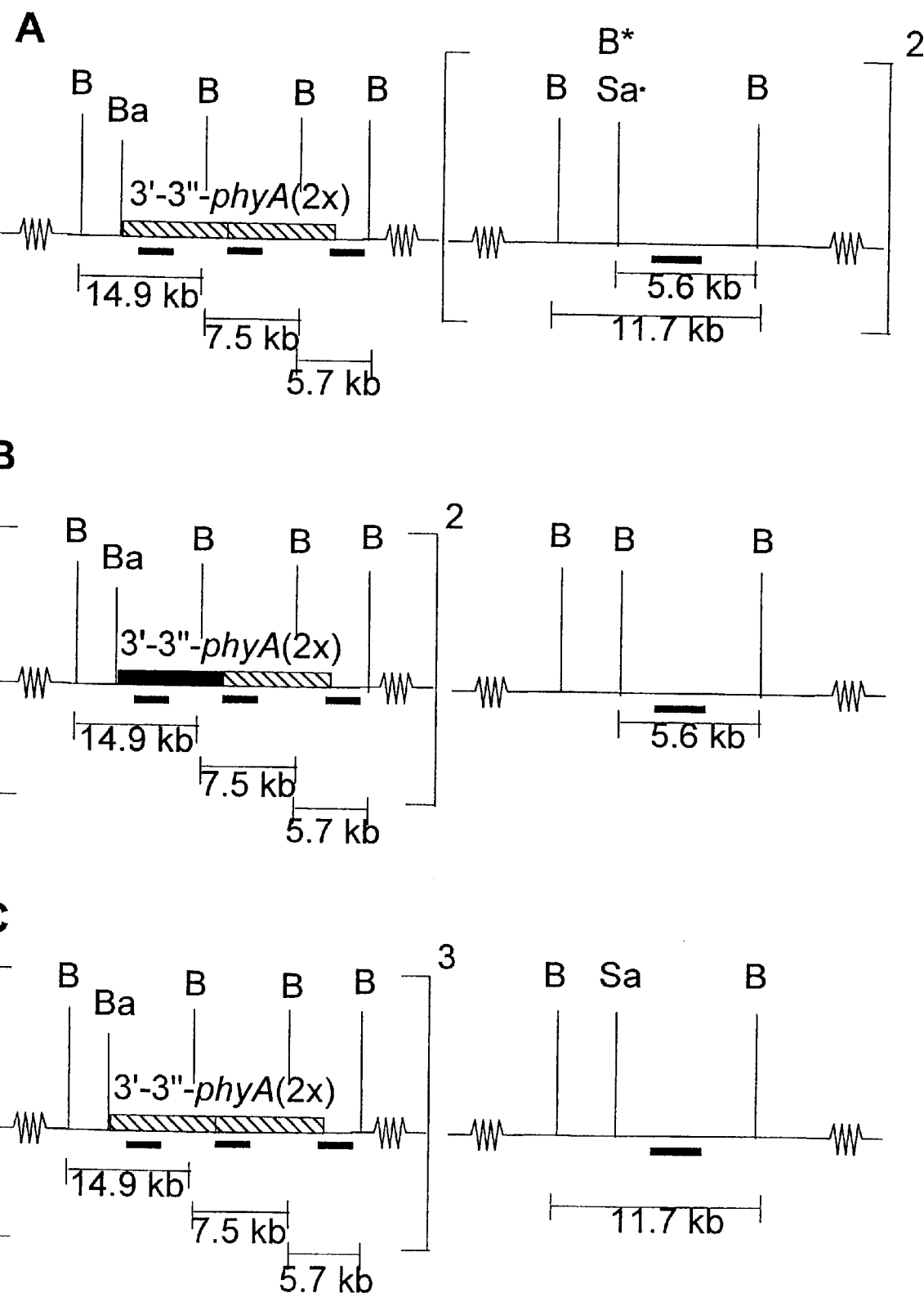

Hybridization patterns of BamHI digests of the parental strain and selected convertants are showed in FIG. 25. As expected, and compared to the parental *A. niger* NP505-2 strain, the PCR identified BamHI$^{2+}$ genotypes showed indeed in BamHI digests reversed intensities for the 2.5 kb and 4.2 kb hybridizing DNA fragments. In the BamHI$^{2+}$ genotype the 2.5 kb fragment represents two BamHI-marked glaA amplicons and the 4.2 kb fragment the remaining SalI or BglII glaA amplicon, depending on the genotype of selected BamHI$^{2+}$ convertants. Observed results clearly indicate that a predefined amplicon can be multiplied by "gene conversion" at the cost of another related amplicon. Hybridization patterns of BglII digests clearly showed that in selected BamHI$^{2+}$ convertants the number of phyA gene copies are doubled as well. As indicated in FIG. 26, a BglII digest of chromosomal DNA of the parental strain show 5 hybridizing DNA fragments using the 3"-glaA fragment as probe. The 5 bands of 14.9, 11.7, 7.5, 5.7 and 5.6 represent, respectively, the 5'-flanking glaA sequence, the SalI-marked amplicon, the phyA—phyA transition, the 3'-flanking glaA sequence and the BglII-marked glaA amplicon. In the parental strain al these bands have more or less the same hybridizing intensity. As shown in FIG. 26 as well, in selected convertants with genotype BamHI$^{2+}$/Sal$^{+}$/BglII$^{-}$ or BamHI$^{2+}$/SalI$^{-}$/BglII$^{+}$, the 5.6 kb or the 11.7 kb DNA fragment, respectively, is absent while the intensity of the 14.9, 7.5 and 5.7 kb hybridizing fragments is doubled.

This result indicates that the 2 phyA cassettes located within the BamHI-marked glaA amplicon of the parental strain are doubled as well by the conversion event in selected BamHI$^{2+}$ convertants.

1.5.d Analyses of phyA Convertants for the Production of Phytase.

To determine whether selected phyA convertants show indeed an increased production of phytase, shake flask fermentations were carried out as described in Materials & Methods.

On average the phytase expression of the parental strain NP505-2 (possessing 2 phyA gene copies) was measured at a level of about 200 U/ml. As predicted for both selected convertants with genotype BamHI$^{2+}$/SalI$^{+}$ or BamHI$^{2+}$/BglII$^{+}$, phytase levels up to 400 U/ml could be detected.

Both strains, designated as *A. niger* NP505-4 and -5, were used in example 1.6 to increase the phyA gene copy number furthermore.

1.6 Selection of Convertants Comprising Multiple Modified DNA Amplicons 1.6.a Rationale.

Expression cassettes targeted in one of the DNA amplicons present in a host strain can be multiplied just by screening progenies of the parental strain and selecting for those recombinant strains in which the desired conversion had occurred. Although to low extent, as described above, conversions among these DNA amplicons occur spontaneously. This process of gene conversion can be used repeatedly, resulting in new convertants which possess an enhanced number of (phyA) modified DNA amplicons. By using this approach, we have identified a convertant possessing finally 6 phyA gene copies, all equally divided over the three modified glaA amplicons of the *A. niger* ISO-505 host.

The degree of "the enrichment of enzyme expression cassette" is dependent on the number of DNA amplicons originally present in the host strain. However, by applying this PCR-based DNA-flag test it appeared to be possible as well, to isolate progenies having a DNA-flag profile which could be explained only by a spontaneous amplification of one of three glaA DNA amplicons. Using this repeatedly, recombinant strains could be selected finally, possessing additional glaA-DNA amplicons compared to the host strain, each containing 2 phyA expression cassettes.

1.6.b. Selection of Putative Convertants Comprising 6 phyA Gene Copies.

Spores of *A. niger* strain NP505-4, described in example 1.5.(d), containing 4 phyA expression cassettes in total (two phyA cassettes in each BamHI-marked glaA amplicon) were seeded onto PDA plates and after 2–3 days the DNA-flag PCR test was performed on the individual progenies using the DNA-flag specific primers. As stated before, again approximately 95% of the tested colonies show no change in glaA amplicon genotype. Approximately 5% of the progenies showed a DNA-flag pattern directing either to a deletion of one of the BamHI- or the SalI-marked amplicons or even to a spontaneous amplification of one of the BamHI-marked glaA-amplicons. Besides these recombinant strains, convertants having the desired DNA-flag pattern, the 200 bp sized BamHI DNA-flag band with a slightly increased intensity, was identified as well. All progeny strains showing the genotype "BamHI$^{3+}$" and "BamHI$^{3+}$/SalI$^+$" were subjected to Southern analyses.

To increase the phyA gene in the "BamHI$^{3+}$/SalI$^+$" convertant up to 8, spores were seeded onto PDA plates and after 2–3 days of growth the DNA-flag PCR test was performed on the individual progenies using the DNA-flag specific primers. At a rather low frequency (1 out of 1000) a "BamHI$^{4+}$" convertant showing a DNA-flag pattern with an increased intensity of the 200 bp sized BamHI-flag DNA fragment and the subsequent loss of the remaining 220 bp sized SalI-flag DNA fragment (FIG. 27). This convertant strain was subjected to Southern analyses as well.

1.6.c Genetic Characterization of Convertants by Southern Analyses.

The phyA gene copy number of above identified convertants (PCR-based genotypes "BamHI$^{3+}$", "BamHI$^{3+}$/SalI$^+$" and "BamHI$^{4+}$" was determined by Southern analyses using BamHI and BglII digests, hybridized respectively with HindIII/XhoI 5'-glaA and SalI/XhoI 3"-glaA specific DNA fragments, as probes. Expected hybridization patterns of the BamHI digests of the parental convertants (genotype BamHI$^{2+}$/SalI$^+$/BglII$^-$ or BamHI$^{2+}$/SalI$^-$/BglII$^+$) and selected convertants thereof are shown in FIGS. 25 and 27. BamHI digests show indeed a sole hybridizing fragment of 2.5 kb for the "BamHI$^{3+}$" convertant. For the "BamHI$^{3+}$/SalI$^+$" an additional band of 4.2 kb was detected, indicating that in this convertant the SalI-marked amplicon is still present as predicted on the result obtained from the DNA-flag pattern. Convertant "BamHI$^{4+}$" shows the same hybridization pattern as the "BamHI$^{3+}$" convertant. For comparison the hybridization patterns of the original parental strain, *A. niger* NP505-2 and the two parental convertant strains BamHI$^{2+}$/SalI$^+$/BglII$^-$ and BamHI$^{2+}$/SalI$^-$/BglII$^+$, see previous figures.

Expected hybridization patterns of a BglII digest on DNA isolated from the above mentioned strains are indicated in FIG. 28. For the "BamHI$^{3+}$" as well as for the "BamHI$^{4+}$" convertant three hybridizing bands (14.5, 7.5 and 5.7) were detectable, all with equal intensities, indicating that besides the 5'- and 3'-flanking sequences the phyA gene copies are increased up to 6 and 8, respectively. For convertant "BamHI$^{3+}$/SalI$^+$" the expected pattern was observed, including the 11.7 kb sized band (characteristic for the presence of the SalI amplicon). The intensity of this band is of course three-fold less.

These results clearly indicate that convertants can be selected, containing three and even four BamHI-marked glaA amplicons, all containing 2 phyA cassettes.

1.6.d Analyses of Phytase Production by Shake Flask Fermentations.

To determine whether selected "BamHI$^{3+}$" and "BamHI$^{4+}$" convertants show indeed an increased production of phytase, shake flask fermentations were carried out as described in Materials & Methods. On average the phytase expression of the parental strain NP505-2 (possessing 2 phyA gene copies) was measured at a level of about 200 U/ml. As predicted for these three selected convertants phytase levels were measured of approximately 600 U for the "BamHI3+/SalI$^+$" and "BamHI$^{3+}$" genotypes and approximately 800 U/ml for the "BamHI$^{4+}$" convertant strain. Later on these strains were designated as *A. niger* NP505-6, -7 and -8, respectively.

1.7 Direct Selection of Recombinants Possessing Enhanced Phytase Production Levels 1.7.a Rationale.

Due to the fact that the glaA DNA amplicons are marked by the so-called DNA-flags, convertants could be selected just by performing the PCR-based DNA-flag test. By applying this genetically-based screening approach we were able to show and to prove that the phyA expression cassettes were multiplied as a consequence of conversions among the phyA modified BamHI-marked glaA amplicon and the other two amplicons.

As stated above we observed a linear relationship between phyA gene copy numbers and phytase production levels, indicating that selection can be based as well on expression. In this example we show the isolation of convertants possessing increased phyA gene copy numbers by screening progenies of an initial BamHI-glaA targeted phyA recombinant strain for enhanced phytase expression levels in micro-well plates.

1.7.b Screening for Enhanced Phytase Expression Levels.

Spores of single colonies of strain *A. niger* NP505-2 were inoculated in a 96-well plates, containing 200 µl *A. niger* fermentation medium as described in Materials & Methods. After 7 days of growth at 34° C., 100% humidity and slightly shaking, the phytase enzyme activity was determined in the supernatant of each well. Enzyme expression levels of approximately thousand progenies were tested. Cells showing an increased phytase activity were harvested, spores collected and applied to an additional micro-titer screening round. Again, cells with increased phytase enzyme activity were found.

In subsequent shake flask fermentations such identified strains show phytase expression levels up to 600 U/ml.

1.7.c Genetic Characterization of Identified Recombinants Strains.

Observed phytase production improvements of above described strains appeared to be the result of an increase of the phyA gene copy number, either by amplification or conversion of the phyA containing BamHI-marked glaA locus. Firstly, the genotype of these selected strains was determined by applying the DNA-flag test and secondly by Southern analyses.

The DNA-flag test clearly indicated that all sorts "DNA-flag" genotypes were amongst the selected strains. These strains showed the same genotypes which have been isolated before already by performing the DNA-flag test as a selection criterium, like:

BamHI$^{2+}$/Sal$^+$/BglII$^-$, BamHI$^{2+}$/Sal$^+$/BglII$^-$,
BamHI$^{3+}$/Sal$^+$/BglII$^-$, BamHI$^{2+}$/Sal$^-$/BglII$^+$,
BamHI$^{3+}$/Sal$^-$/BglII$^-$.

All these genotypes were confirmed by Southern analyses as described in previous examples.

EXAMPLES PENICILLIUM

2.1 Selection and Characterization of the *P. chrysogenum* Host 2.1.a Rationale.

Amplification of inserted genes through gene conversion requires the presence of multiple homologous DNA domains in the genome. Such domains have been described for *P. chrysogenum* (in this report referred to as PEN amplicons: Fierro et al., 1995 Proc. Natl. Acad. Sci. USA 92:6200–6204). The penicillin cluster, a 15 kb domain encompassing the penicillin biosynthetic genes, pcbAB, pcbc and penDE, is located on these PEN amplicons (FIG. 29) (Diez et al., 1990 J. Biol. Chem. 265: 16358–16365; Smith et al., 1990 EMBO J. 9: 741–747). Here we describe the selection and characterization of *P. chrysogenum* host strain CBS 649.97, containing multiple copies of the PEN amplicon.

2.1.b Quantitation of PEN Amplicons.

Figure 30:
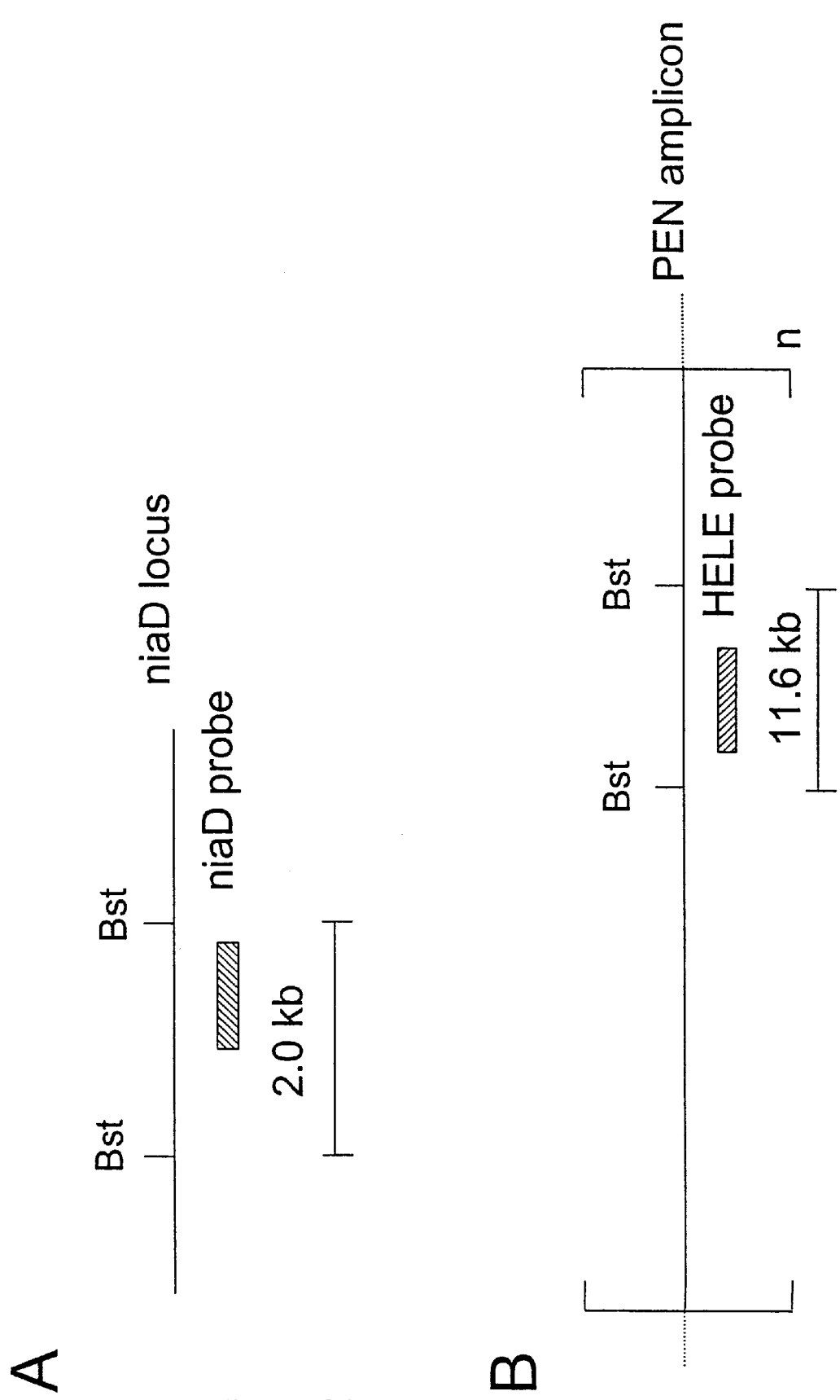

*P. chrysogenum* strain CBS 649.97 was obtained by classical strain improvement from strain Wis54-1255 (ATCC 28089), which contains a single PEN amplicon (Fierro et al., 1995 Proc. Natl. Acad. Sci. USA 92:6200–6204).The number of PEN amplicons in strain CBS 649.97 was determined by Southern analyses. To this end, chromosomal DNA was digested with BstXI and hybridized to HELE and niaD probes. A 7-fold higher HELE/niaD hybridization ratio was detected for CBS 649.97 compared to Wis54-1255 (FIGS. 30, 42). Similarly, NotI-digested DNA separated by CHEF, was hybridized to HELE probe (FIG. 42). A major hybridization signal, approximately 420 kb larger in CBS 649.97 than in Wis54-1544, was detected (FIG. 31). These results indicated the presence of about 7 PEN amplicons in strain CBS 649.97.

2.2 Construction of Expression Vectors 2.2.a Rationale.

Directed insertion (targeting) of rDNA molecules into the genome occurs through homologous recombination. Therefore, rDNA cassettes should be flanked by DNA fragments homologous to the target site in the genome (FIG. 32). Two targeting domains within the penicillin cluster, defined as HELE and HELF, were choosen for directed insertion of the expression cassettes into the PEN amplicons (FIG. 29). Here we describe the design and construction of amdS, cefE and cefF expression vectors used in this report.

2.2.b Basic Design of Expression Vectors.

Linear DNA molecules are crucial for targeted integration into the genome. Furthermore, both 5' and 3' ends (flankings) must consist of DNA homologous to the desired integration site. Transformation fragments, therefore, comprise the expression cassette (the gene of interest regulated by a suitable promoter and terminater) flanked by the 5' and 3' targeting domains. These fragments are cloned into an *E. coli* vector for propagation of the plasmid. The resulting expression vectors are designed such that *E. coli* sequences are removed during linearization and isolation of the transformation fragment (FIG. 32). Hence, recombinant strains will be free of *E. coli* DNA (E.P. 0 635 574 A1).

2.2.c Construction of Expression Vector pHELE-A1.

The 5' HELE targeting domain was PCR-amplified from chromosomal DNA of *P. chrysogenum* strain CBS 649.97, using oligo's 1 and 2. The resulting product was cloned as a NotI-SpHI fragment in pZErO™-1 (Invitrogen, Carlsbad, USA), yielding plasmid pHELE5'. Similarly, the 3' HELE targeting domain was PCR-amplified using oligo's 3 and 4 and cloned as a HindIII-NotI fragment in pHELE5', yielding plasmid pHELE53. The amdS expression cassette, encompasing amdS regulated by $P_{gpdA}$ and $T_{amdS}$, was PCR-amplified from plasmid pGBDEL4L (E.P. 0 635 547 A1), using oligo's 5 and 6. The resulting product was cloned as a NotI fragment in pHELE53, yielding expression vector pHELE-A1 (FIG. 33).

2.2.d Construction of Expression Vector pHELF-A1.

The 5' HELF targeting domain was PCR-amplified from chromosomal DNA of *P. chrysogenum* strain CBS 649.97, using oligo's 7 and 8. The resulting product was cloned as a NotI-XbaI fragment in pZErO™-1 (Invitrogen, Carlsbad, USA), yielding plasmid pHELF5'. Similarly, 3' HELF flanking was PCR-amplified, using oligo's 9 and 10, and cloned as a PstI-NotI fragment in pHELF5', yielding plasmid pHELF53. The amdS expression cassette, encompassing amdS regulated by $P_{gpdA}$ and $T_{amdS}$, was PCR-amplified from plasmid pGBDEL4L (E.P. 0 635 547 A1), using oligo's 5 and 6. The resulting product was cloned as a NotI fragment in pHELF53. yielding expression vector pHELF-A1 (FIG. 34).

2.2.e Construction of Expression Vector pHELE-E1.

The $P_{pcbC}$ was PCR-amplified from genomic DNA of *P. chrysogenum* strain CBS 649.97, using oligo's 11 and 12. The resulting product was cloned as a XhoI-NdeI fragment in pGSEWA (WO 95/04148), yielding pISEWA-N. Finally, the cefE expression cassette, regulated by $P_{pcbC}$ and $T_{penDE}$, was cloned as a NotI fragment from pISEWA-N in pHELE53, yielding expression vector pHELE-E1 (FIG. 35).

2.2.f Construction of Expression Vector pHELF-F1.

The cefF gene was PCR-amplified from genomic DNA of *S. clavuligerus* ATCC 27064, using oligo's 13 and 14, according to the Expand™ Long Template PCR System (Boehringer Mannheim). Cycle conditions: 30×(1 min 98° C., 5 min 70° C.), 1×(7 min 72° C.). The resulting product was cloned as a NdeI-NsiI fragment in pISEWA-N (substituting cefE), yielding pISFWA. Finally, the cefF expression cassette, regulated by $P_{pcbC}$ and $T_{penDE}$, was cloned as a NotI fragment from pISFWA in pHELF53, yielding expression vector pHELF-F1 (FIG. 36).

2.3 Modification of PEN Amplicons with cefE 2.3.a Rationale.

Figure 37:
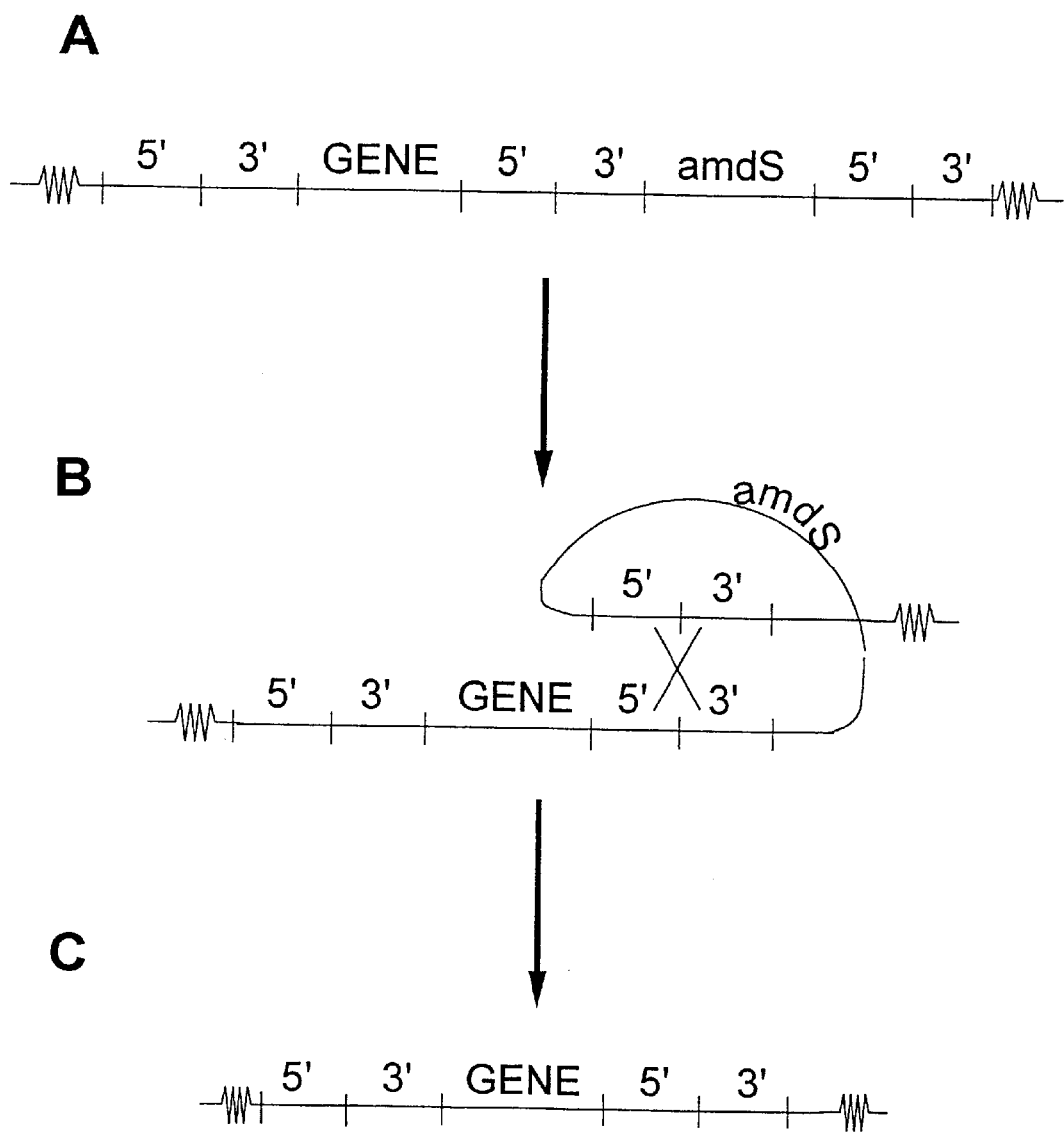

Efficient selection of transformants requires a selectable marker. Co-transformation of fungi is a well known procedure by which the host is transformed simultaneously by two different rDNA molecules; one containing the gene of interest and the other the selection marker. Use of the bi-directional amdS marker allows repeated transformation of the *P. chrysogenum* host (E.P. 0 635 547 A1). Recombination over the direct repeats created by targeted integration, will result in loss of the amdS cassette and can be selected on Fluoroacetamide medium (FIG. 37). Here we describe selection of amdS-free recombinants containing the cefE expression cassette integrated in one of the PEN amplicons.

2.3.b Selection of Targeted amdS, cefE co-transformants.

Figure 40A:
Figure 40B:
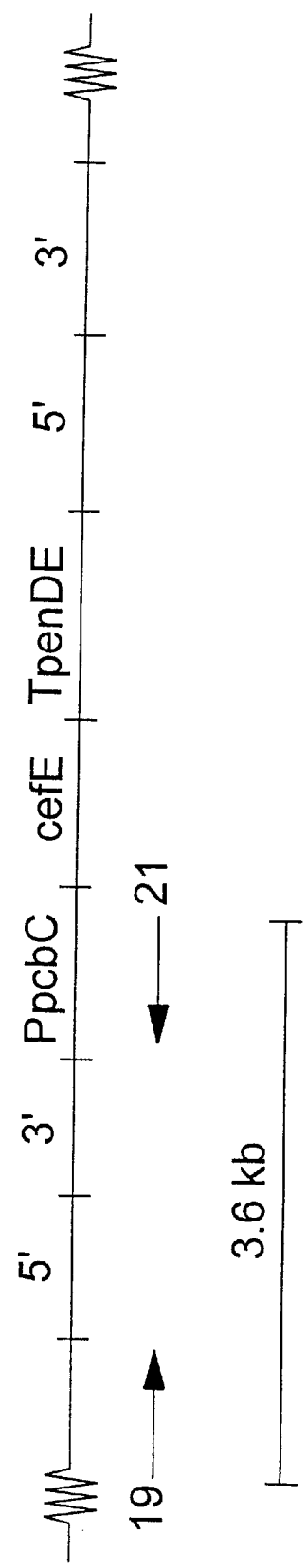

*P. chrysogenum* strain CBS 649.97 was co-transformed with SfiI-linearized HELE-A1 and HELE-E1 fragments (FIGS. 33, 35). Transformants containing amdS were selected on acetamide plates and tested for cefE by cassette PCR, using oligo's 17 and 18 (FIG. 40a). Co-transformants with amdS or cefE integrated in HELE, were identified by targeting PCR, using oligo's 19, 20 and 21 (FIGS. 40.b,c). These strains were used for isolation of amdS⁻ recombinants.

2.3.c Selection of amdS⁻ (marker-free) cefE Recombinants.

Spores of amdS, cefE, co-transformants described in 2.3.b, were plated onto Fluoroacetamide medium. Recombinants retaining cefE were identified by the *E. coli* bioassay. Loss of amdS but presence of at least one cefE copy was confirmed by cassette PCR, using oligo's 15, 16, 17 and 18 (FIGS. 40.*a,d*). These strains were selected for Southern analyses.

2.3.d Southern Analyses of amdS⁻ Recombinants.

Figure 38:
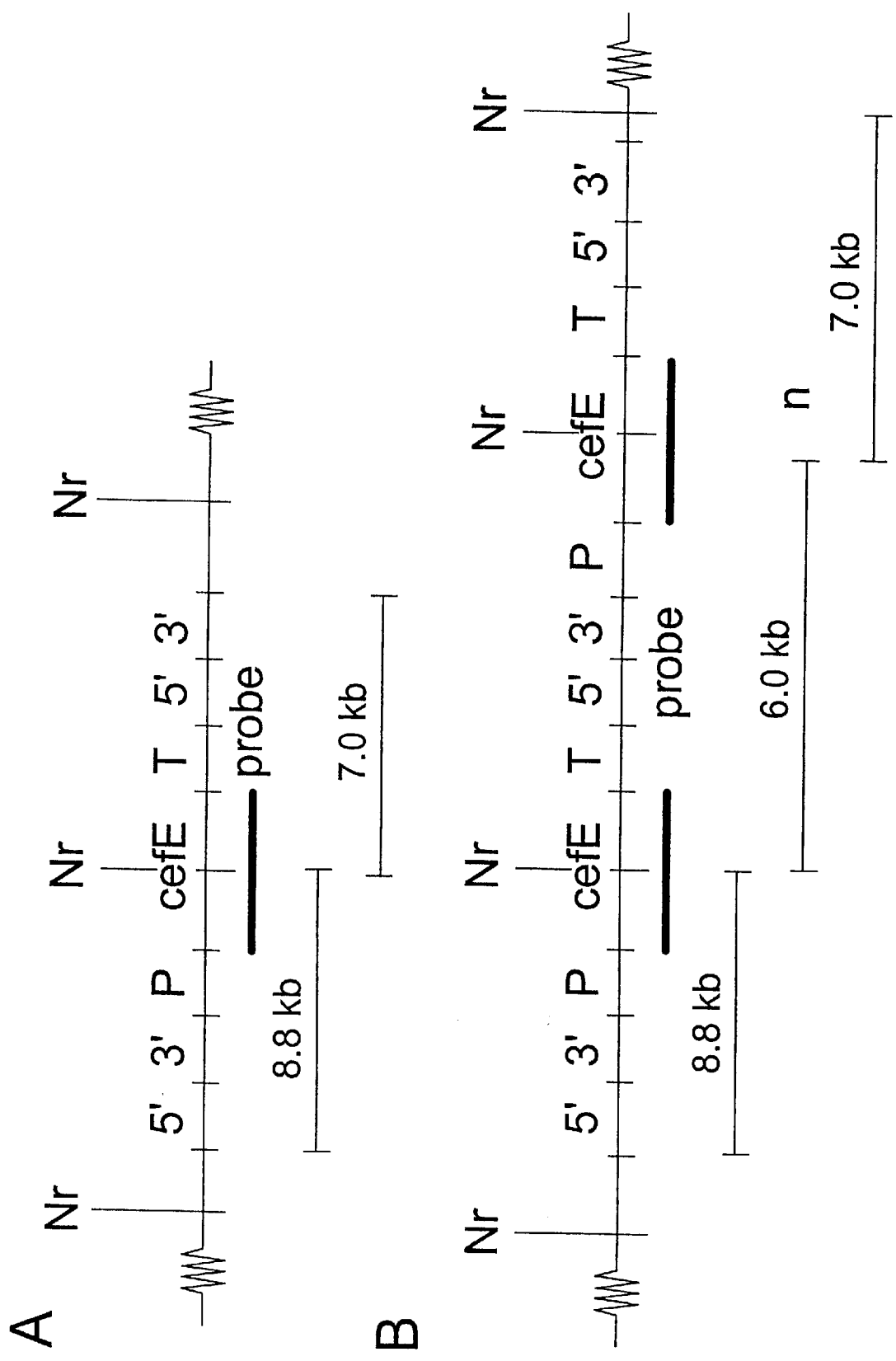

Integration of cefE in HELE and the number of cefE copies in amdS⁻, cefE⁺ recombinants was analyzed by Southerns and TAFE. To this end, chromosomal DNA of recombinants was digested with NruI and hybridized to cefE probe (FIGS. 38, 42). Similar hybridizations were performed with HpaI-digested DNA, separated by TAFE (FIG. 39). Recombinant strains with a hybridization pattern expected for integration of cefE in HELE, were selected for further experiments.

2.4 Modification of a Second Amplicon with amdS 2.4.a Rationale.

Gene conversion essentially substitutes the genetic information from an acceptor DNA strand by a donor DNA strand. Both donor and acceptor strands can be marked to visualize this event. Strains as described in 2.3 already have one amplicon marked by cefE (in this case the donor strand). Here we describe the modification of an acceptor strand by insertion of a single amdS cassette in a different PEN amplicon than cefE (FIG. 43).

2.4.b Targeting of amdS to a Second PEN Amplicon.

Figure 40C:
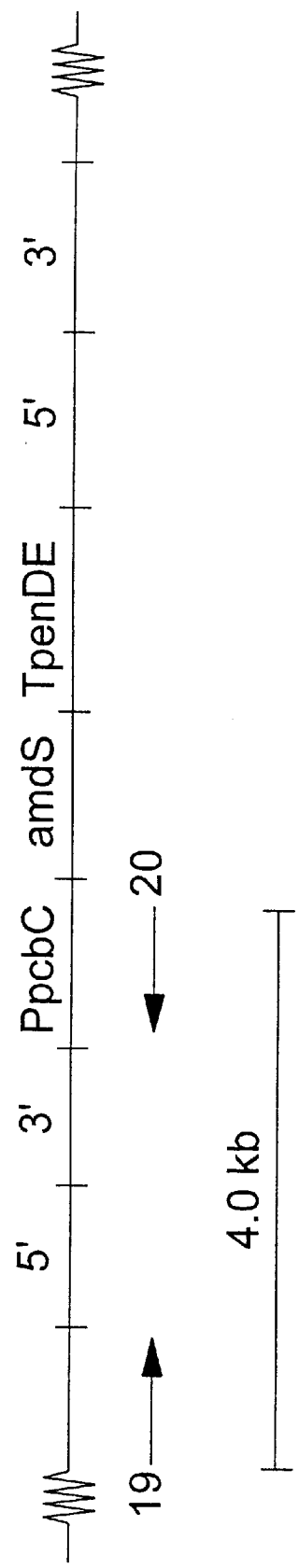
Figure 40D:
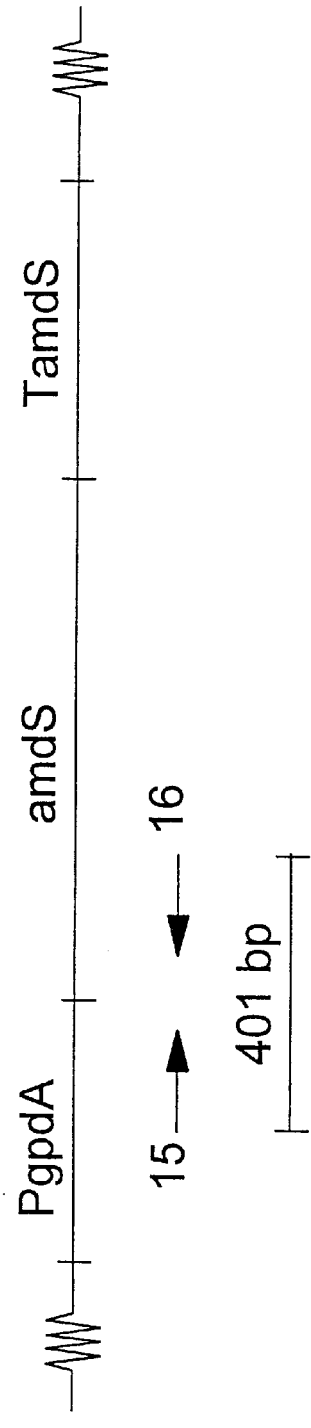
Figure 40E:
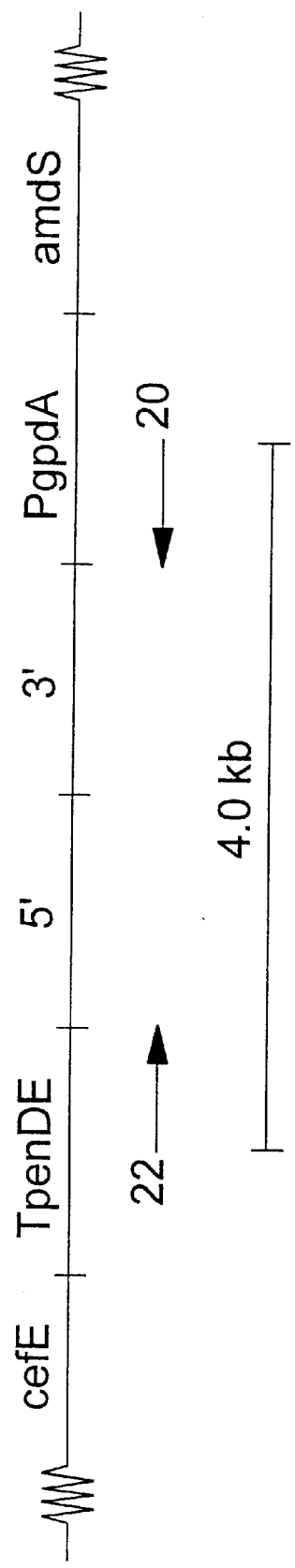
Figure 40F:
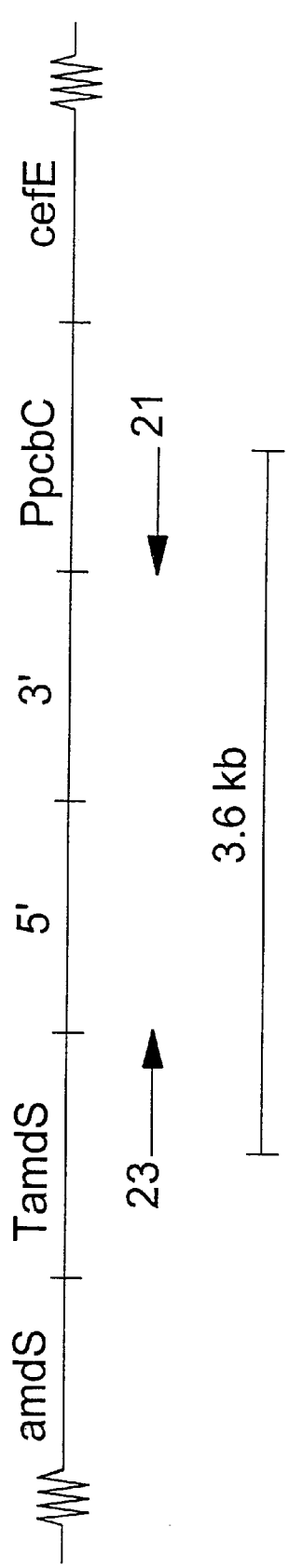
Figure 40G:
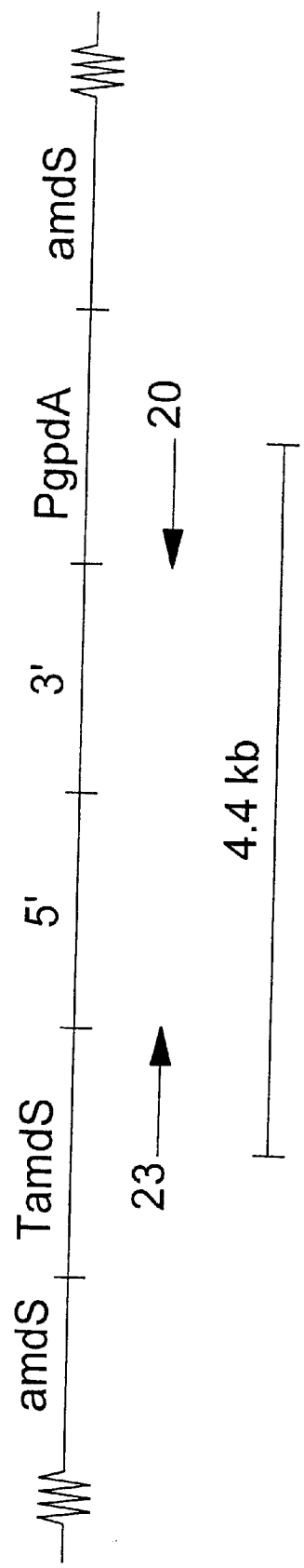
Figure 40H:
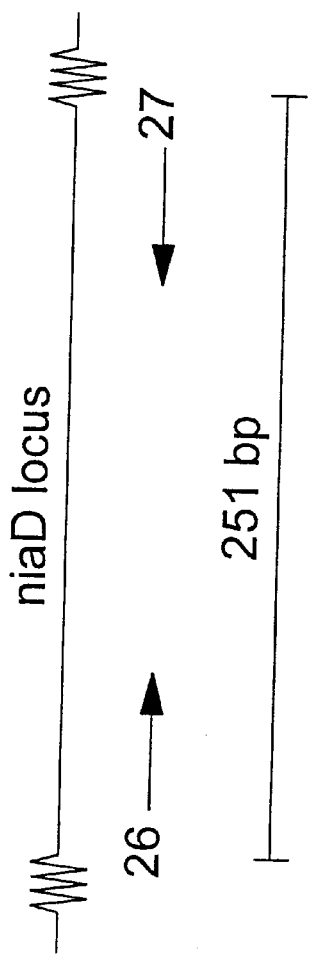
Figure 40I:
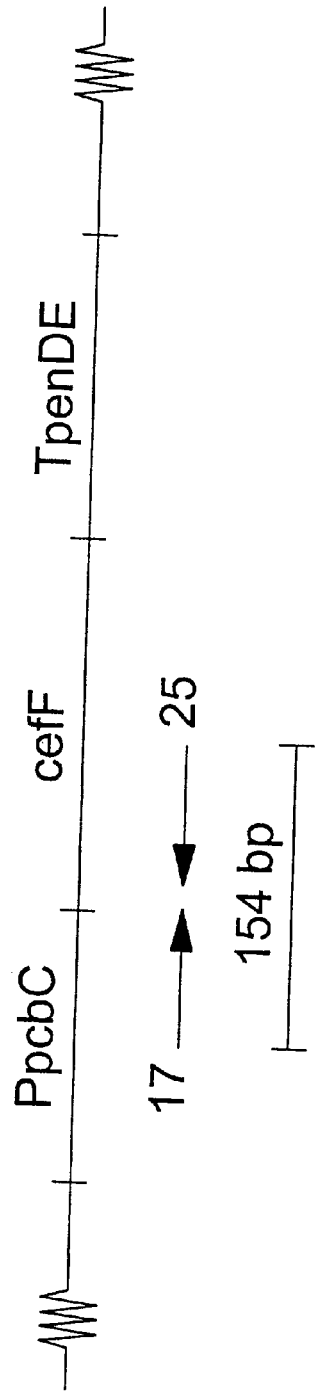

Strains as described in 2.3.d, containing cefE in one amplicon, were transformed with SfiI-linearized HELE-A1 fragment (FIG. 33). Integration of amdS and targeting to HELE was tested by cassette and targeting PCR using oligo's 15, 16 and 19, 20, respectively (FIGS. 40*c,d*). Integrations of amdS adjacent to cefE or multiple amdS copies in a single HELE locus were identified by targeting PCR using oligo's 20, 21, 22 and 23 (FIGS. 40*e,f,g*). The remaining strains, hence, containing a single amdS cassette integrated in a second amplicon, were selected for Southern analyses.

2.4.c Southern Analyses of amdS Transformants.

Chromosomal DNA of transformants described in 2.4.b was digested with HpaI and hybridized to amdS probe (FIGS. 41, 42). Strains with a hybridization pattern expected for correct integration of amdS in HELE, were selected for gene conversion experiments.

2.5 Increase of Production by Gene Conversion 2.5.a Rationale.

The copy number of an integrated gene increases through gene conversion (FIG. 43). Consequently, production of the enzyme encoded by the gene or its catalytic activity can increase. Recombinant *P. chrysogenum* strains expressing cefE, produce adipoyl-7-ADCA when fermented under the proper conditions (Crawford et al., 1995 BIO/Technol. 13:58–62). Here we describe the selection and characterization of cefE gene convertants and the resulting increase of adipoyl-7-ADCA production.

2.5.b Selection of cefE gene Convertants.

Spores of strains described in 2.5.a, containing cefE and amdS in different PEN amplicons, were plated on Fluoroacetamide medium to select amdS⁻ recombinants. The amdS⁻, cefE⁺ genotype of these recombinants was confirmed by cassette PCR using oligo's 15, 16, 17, 18, 26 and 27 (FIGS. 40*a,d,h*). Oligo's 26 and 27 were included to amplify a fragment of the unique niaD locus, which served as an internal reference for relative quantitation of the PCR products. Gene convertants, identified as strains which lost the amdS marker but gained cefE copies, as judged by the increased cefE/niaD ratio compared to the parental strain, were selected for Southern analyses.

2.5.c Southern Analyses of cefE Gene Convertants.

Chromosomal DNA of strains selected in 2.5.b, were digested with NruI and hybridized to cefE and niaD probes. Strains with a hybridization pattern identical to the parental strain, but increased ratio of the cefE/niaD hybridization signals, were selected for adipoyl-7-ADCA fermentations (FIG. 48).

2.5.d Adipoyl-7-ADCA Production of cefE gene Convertants.

Adipoyl-7-ADCA production of gene convertants selected in 2.7.b, was determined by shake flask fermentations. All selected strains produced significantly more adipoyl-7-ADCA than the corresponding parental strains.

2.6 Simultaneous Increase of Different Expression Cassettes by Gene Conversion 2.6.a Rationale.

Domains encompassing large segments of the amplicons, or even extending the borders of the amplicons, can participate in gene conversion. Hence, the copy number of different genes adjacent to each other can increase simultaneously through gene conversion. Recombinant *P. chrysogenum* strains expressing cefE and cefF, produce adipoyl-7-ADAC, when fermented under the proper conditions (Crawford et al., 1995 BIO/Technol. 13:58–62). Here we describe the simultaneous gene conversion of cefE and cefF expression cassettes, targeted to different loci on the same PEN amplicon (cefE+cefF), and the resulting increase of adipoyl-7-ADAC production.

2.6.b Selection of (cefE+cefF) Transformants.

Figure 40J:
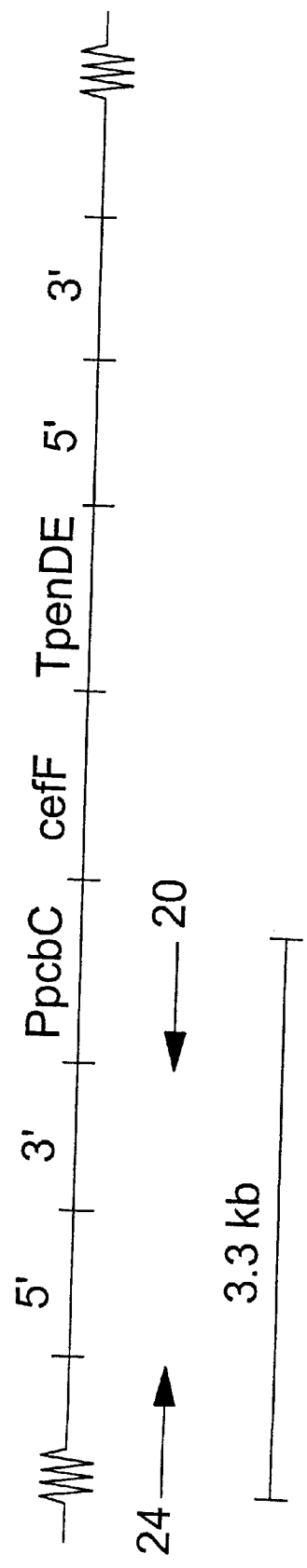
Figure 40K:
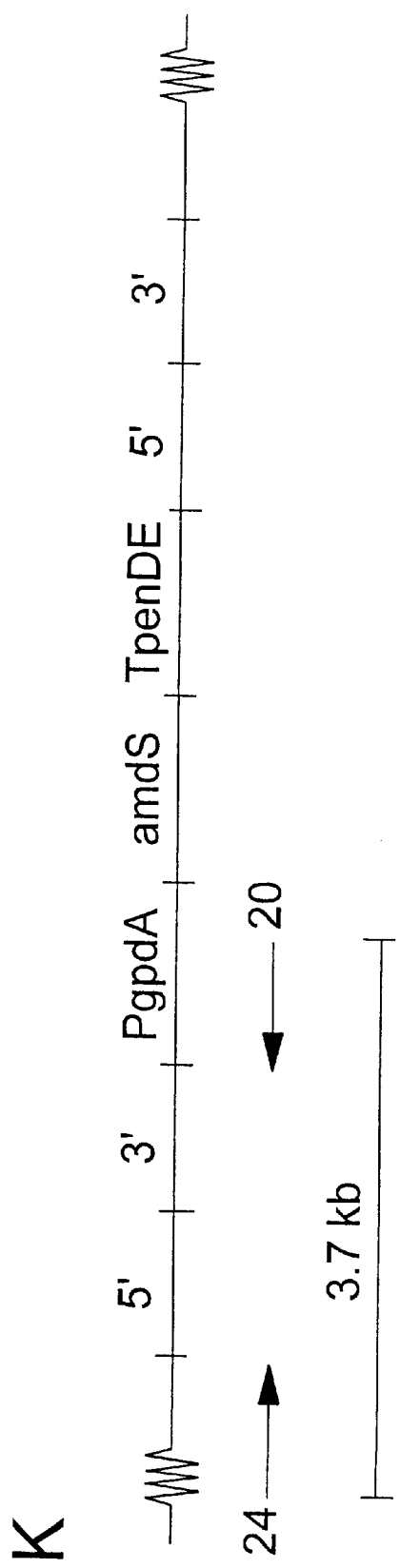

Strains as described in 2.3.d, containing cefE integrated in HELE, were co-transformend with SfiI- linearized HELF-A1 and HELF-F1 fragments (FIGS. 34, 36). Transformants were selected on acetamide plates and tested by cassette PCR for cefF and amdS, using oligo's 15, 16, 17 and 25 (FIGS. 40*d,j*). Integration of amdS or cefE in HELF was determined by targeting PCR using oligo's 20, 21 and 24 (FIGS. 40*j,k*). Chromosomal DNA of these strains was digested with NotI, blotted and hybridized to HELE probe (FIG. 44). Strains with a hybridizing fragment corresponding to integration of cefF or amdS in HELF on the PEN amplicon already containing cefE, were used for selection of marker free (amdS-) recombinants.

2.6.c Selection of MARKER-GENE FREE (cefE+cefF) Recombinants.

Spores of strains described in 2.6.b were plated on Fluoroacetamide medium for selection of amdS⁻ recombinants. Recombinants that lost amdS but retained cefE and cefF, were identified by cassettte PCR, using oligo's 30 15, 16, 17, 18, and 25 (FIGS. 40*a,d,j*). Chromosomal DNA of these strains was digested with NruI and hybridized to cefF probe (FIGS. 42, 45). Strains with correct integration of cefF in HELF were used for selection of gene convertants.

2.6.d Selection of (cefE+cefF) Gene Convertants.

Spores of strains described in 2.6.c were grown to single colonies and analyzed for the amount of cefE, cefF and niaD by cassettte PCR, using oligo's 17, 18, 25, 26 and 27 (FIGS. 40*a,h,i*). Gene convertants were identified by simultaneously increased ratio's of cefE/niaD and cefF/niaD, compared to the parental strains. Increased copy numbers of cefE and cefF was confirmed by Southern analysis. To this end, chromosomal DNA was digested with NruI and hybridized to cefE and niaD probes (FIG. 46). Blots were stripped and subsequently hybridized to cefF and niaD probes (FIG. 47). Strains with increased ratios of both cefE/niaD and cefF/niaD compared to the parental strains, were selected for adipoyl-7-ADAC.

2.6.e Adipoyl-7-ADAC Production of (cefE+cefF) Gene Convertants.

Adipoyl-7-ADAC production of gene convertants selected in 2.6.d, was determined by shake flask fermentations. All selected strains produced increased amounts of adipoyl-7-ADAC compared to the parental strains.

What is claimed is:

1. A filamentous fungus which has integrated a recombinant DNA molecule into at least two substantially homologous DNA domains of its chromosome(s), wherein the DNA domains are not the ribosomal DNA repeats.

2. A filamentous fungus of claim 1, wherein a recombinant DNA molecule is integrated into each of its substantially homologous DNA domains.

3. The filamentous fungus of claim 1, wherein said DNA domains are amplicons.

4. The filamentous fungus of claim 1, wherein said DNA domains are domains which in their native state comprise an endogenous gene capable of high level expression.

5. A filamentous fungus of claim 1, wherein each version of said DNA domains is distinguished from the other versions of the domains by means of a unique sequence tag.

6. The filamentous fungus of claim 1, wherein said recombinant DNA molecule contains an expression cassette for the expression of a desired gene.

7. The filamentous fungus of claim 1, wherein the recombinant DNA molecule lacks a selectable marker gene.

8. The filamentous fungus of claim 1 which belongs to a genus selected from the group consisting of Aspergillus, Trichoderma, Penicillium, Cephalosporium, Acremonium, Fusarium, Mucor, Rhizophus, Phanerochaete, Neurospora, Humicola, Claviceps, Sordaria, Ustilago, Schizophyllum, Blakeslea, Mortierella, Phycomyces, and Tolypocladium.

9. A method for preparing a filamentous fungus as defined in claim 1, wherein said method comprises the steps of:
 (a) transforming a filamentous fungus comprising in one or more of its chromosomes at least two substantially homologous DNA domains suitable for integration of one or more copies of a recombinant DNA molecule and wherein the DNA domains are not the ribosomal DNA repeats, with a recombinant DNA molecule;
 (b) selecting a transformant with at least one recombinant DNA molecule integrated in at least one of the DNA domains;
 (c) propagating the transformant obtained in (b) and selecting from its progeny a strain in which at least two of the DNA domains comprise the integrated recombinant DNA molecule.

10. A method for production of a protein of interest, comprising the steps of:
 (a) culturing a filamentous fungus according to claim 1 under conditions conducive to the expression of the protein of interest; and
 (b) recovering the protein of interest.

11. A method for the production of a metabolite of interest, comprising the steps of:
 (a) culturing a filamentous fungus of claim 1 under conditions conducive to the production of the metabolite of interest; and
 (b) recovering the metabolite of interest.

12. The filamentous fungus of claim 4, wherein said endogenous gene is selected from the group consisting of genes encoding glycolytic enzymes, amylolytic enzymes, cellulolytic enzymes and antibiotic biosynthetic enzymes.

13. The filamentous fungus of claim 4, wherein said endogenous gene is inactivated in each copy of said DNA domain.

14. The filamentous fungus of claim 5, wherein said sequence tag is a restriction site.

15. The filamentous fungus of claim 6, wherein said desired gene encodes a secreted enzyme.

16. The filamentous fungus of claim 6, wherein said desired gene encodes an intracellular enzyme.

17. The filamentous fungus of claim 7, which lacks a selectable marker gene.

18. The filamentous fungus of claim 8, which is selected from the group consisting of members of the *Aspergillus niger* group, *Aspergillus oryzae, Trichoderma reesei* and *Penicillium chrysogenum.*

19. The method of claim 9, comprising in addition to steps (a), (b), and (c), the steps of:
 (d) propagating the strain in which at least two of the DNA domains comprise an integrated DNA molecule and selecting from its progeny a strain in which additional copies of the DNA domains comprise the integrated recombinant DNA molecule;
 (e) repeating step (d) until a strain is obtained in which each of the DNA domains comprises the integrated recombinant DNA molecule.

20. The method of claim 9, wherein the recombinant DNA molecule comprises sequences which are substantially homologous to the DNA domains.

21. The method of claim 9, wherein a bidirectional selectable marker is used for transforming the filamentous fungus in step (a), and wherein, prior to step (c), transformants are selected for the absence of the bidirectional marker.

22. The method of claim 10, wherein the protein of interest is a secreted protein.

23. The method of claim 11, wherein the metabolite of interest is a secondary metabolite.

24. The filamentous fungus of claim 12, wherein said endogenous gene is selected from the group consisting of a glucoamylase gene, a TAKA amylase gene, a cellobiohydrolase gene and penicillium biosynthetic genes.

25. The filamentous fungus of claim 13, wherein said endogenous gene is inactivated by means of an irreversible deletion of at least part thereof.

26. The filamentous fungus of claim 16, wherein one or more recombinant DNA molecules comprising one or more expression cassettes for intracellular enzymes are integrated into said DNA domains and wherein the intracellular enzymes are part of a metabolic pathway which is not native to the filamentous fungus.

27. The method of claim 21, wherein the bidirectional marker is a dominant marker.

28. The filamentous fungus of claim 25, wherein said irreversible deletion comprises at least part of the promoter and upstream activating sequences.

29. The filamentous fungus of claim 26, wherein the intracellular enzymes are selected from the group comprising a deacetoxycephalosporin C synthetase (expandase) and a deacetylcephalosporin C synthetase (hydroxylase).

* * * * *

SEQUENCE LISTING

<160> NUMBER OF SEQ ID NOS: 52

<210> SEQ ID NO 1
<211> LENGTH: 41
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 1
gtagctgcgg ccgcctccgt cttcacttct tcgcccgcac t                          41

<210> SEQ ID NO 2
<211> LENGTH: 48
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 2
caaagggcat gcggccgtat cggccggtga caaacatcat tcaacgcc                   48

<210> SEQ ID NO 3
<211> LENGTH: 42
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 3
atgtttaagc ttggccgata cggccaaaac acctttgatt tc                         42

<210> SEQ ID NO 4
<211> LENGTH: 45
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 4
caagttgcgg ccgctcctca ctaacgagcc agcagatatc gatgg                      45

<210> SEQ ID NO 5
<211> LENGTH: 39
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 5
aagcttatgc ggccgcgaat tcgagctctg tacagtgac                             39

<210> SEQ ID NO 6
<211> LENGTH: 40
<212> TYPE: DNA
<213> ORGANISM: Artificial

```
<220> FEATURE:
<223> OTHER INFORMATION: oligonucleotide
<221> NAME/KEY: misc_feature
<223> OTHER INFORMATION: PCR primer

<400> SEQUENCE: 6
cggtacgtgc ggccgctcgt accatgggtt gagtggtatg                               40

<210> SEQ ID NO 7
<211> LENGTH: 43
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 7
atatgtgcgg ccgctttaca tggtcaatgc aattagatgg tgg                           43

<210> SEQ ID NO 8
<211> LENGTH: 47
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 8
ataactctag aggccctacc ggcctttgca aatatactgt aagaacc                       47

<210> SEQ ID NO 9
<211> LENGTH: 43
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 9
gtatattctg cagggccggt agggccaaca gtttccgcag gtg                           43

<210> SEQ ID NO 10
<211> LENGTH: 43
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 10
gtatgggcgg ccgctttaca actagaatat gggaacctgt ggg                           43

<210> SEQ ID NO 11
<211> LENGTH: 61
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 11
ctcgagtgcg gccgcaaagc tagcttgata tcgaattcct tatactgggc ctgctgcatt         60
``` g    61

<210> SEQ ID NO 12
<211> LENGTH: 45
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 12
gtccatatgg gtgtctagaa aaataatggt gaaaacttga aggcg    45

<210> SEQ ID NO 13
<211> LENGTH: 30
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 13
catatggcgg acacgcccgt accgatcttc    30

<210> SEQ ID NO 14
<211> LENGTH: 54
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 14
atgcattggc tcgtcatgaa gagcctatca tccggcctgc ggctcgttct tcgc    54

<210> SEQ ID NO 15
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 15
cagctacccc gcttgagcag acatc    25

<210> SEQ ID NO 16
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 16
gtcagggaag aacacgaggg cgcag    25

<210> SEQ ID NO 17
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 17
ccctctcttc gtcgttgtcc acgcc                                    25

<210> SEQ ID NO 18
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 18
atgtccttgg ccgacttcag ctcgg                                    25

<210> SEQ ID NO 19
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 19
gacgagccaa tgcatctttt gtatg                                    25

<210> SEQ ID NO 20
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 20
cgggtactcg ctctacctac ttcgg                                    25

<210> SEQ ID NO 21
<211> LENGTH: 27
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 21
gcccagtata aggaattcga tatcaag                                  27

<210> SEQ ID NO 22
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 22
agggtcgaca ctagttctag agcgg                                    25

<210> SEQ ID NO 23

```
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 23
gacgttatcg gacggagact cagtg                                          25

<210> SEQ ID NO 24
<211> LENGTH: 24
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 24
gcctactctg ttctggagag ctgc                                           24

<210> SEQ ID NO 25
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 25
cccccatccc ggtcacgcac tcgcg                                          25

<210> SEQ ID NO 26
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 26
cacagagaat gtgccgtttc tttgg                                          25

<210> SEQ ID NO 27
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 27
tcacatatcc cctactcccg agccg                                          25

<210> SEQ ID NO 28
<211> LENGTH: 15
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 28
```
gtcgcgtatc ccagg                                                          15

<210> SEQ ID NO 29
<211> LENGTH: 18
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 29
gtcaaaggat atgcatac                                                       18

<210> SEQ ID NO 30
<211> LENGTH: 39
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 30
agcttatgcg gccgcgaatt caggtaccgt atctcgaga                                39

<210> SEQ ID NO 31
<211> LENGTH: 39
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 31
aatttctcga gatacggtac ctgaattcgc ggccgcata                                39

<210> SEQ ID NO 32
<211> LENGTH: 30
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 32
gtgcgaggta ccacaatcaa tccatttcgc                                          30

<210> SEQ ID NO 33
<211> LENGTH: 36
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 33
atggttcaag aactcggtag cctttcctt gattct                                    36

<210> SEQ ID NO 34
<211> LENGTH: 36
<212> TYPE: DNA
<213> ORGANISM: Artificial
<220> FEATURE:

```
<223> OTHER INFORMATION: oligonucleotide
<221> NAME/KEY: misc_feature
<223> OTHER INFORMATION: PCR primer

<400> SEQUENCE: 34
agaatcaagg aaaaggctac cgagttcttg aaccat                                36

<210> SEQ ID NO 35
<211> LENGTH: 42
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 35
atcaatcaga agctttctct cgagacgggc atcggagtcc cg                         42

<210> SEQ ID NO 36
<211> LENGTH: 21
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 36
gaccatgatt acgccaagct t                                                21

<210> SEQ ID NO 37
<211> LENGTH: 36
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 37
ggatccttaa ctagttaagt gggggcctgc gcaaag                                36

<210> SEQ ID NO 38
<211> LENGTH: 36
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 38
ttaactagtt aaggatccac aatcaatcca tttcgc                                36

<210> SEQ ID NO 39
<211> LENGTH: 34
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 39
gctctagagc ggccgcgaat tcatccggag atcc                                  34
```

```
<210> SEQ ID NO 40
<211> LENGTH: 18
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 40
ctttgcgcag gcccccac                                               18

<210> SEQ ID NO 41
<211> LENGTH: 18
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 41
tgcagggtaa atcaggga                                               18

<210> SEQ ID NO 42
<211> LENGTH: 19
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 42
tccgctaaag gtggtcgcg                                              19

<210> SEQ ID NO 43
<211> LENGTH: 20
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 43
ccccagcatc attacacctc                                             20

<210> SEQ ID NO 44
<211> LENGTH: 20
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 44
aaaggacccg agatccgtac                                             20

<210> SEQ ID NO 45
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer
```

<400> SEQUENCE: 45
tctcgatacc aaggtcacca cgggc                                              25

<210> SEQ ID NO 46
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 46
gcatccatcg gccaccgtca ttgga                                              25

<210> SEQ ID NO 47
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 47
atccagacca gcacaggcag cttcg                                              25

<210> SEQ ID NO 48
<211> LENGTH: 25
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 48
tccgcatgcc agaaagagtc accgg                                              25

<210> SEQ ID NO 49
<211> LENGTH: 36
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 49
gtcgacttaa ctagttaagg cttcagacgc agcgag                                  36

<210> SEQ ID NO 50
<211> LENGTH: 36
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 50
ttaactagtt aagtcgacac aatcaatcca tttcgc                                  36

<210> SEQ ID NO 51
<211> LENGTH: 36
<212> TYPE: DNA
<213> ORGANISM: Artificial

```
                                          -continued

<220> FEATURE:
<223> OTHER INFORMATION: oligonucleotide
<221> NAME/KEY: misc_feature
<223> OTHER INFORMATION: PCR primer

<400> SEQUENCE: 51
agatctttaa ctagttaagt ggcctgaaca gtgccg                                   36

<210> SEQ ID NO 52
<211> LENGTH: 36
<212> TYPE: DNA
<213> ORGANISM: Artificial
<220> FEATURE:
<223> OTHER INFORMATION: oligonucleotide
<221> NAME/KEY: misc_feature
<223> OTHER INFORMATION: PCR primer

<400> SEQUENCE: 52
ttaactagtt aaagatctac aatcaatcca tttcgc                                   36
```